United States Patent
Lokey

(10) Patent No.: US 11,001,609 B2
(45) Date of Patent: May 11, 2021

(54) CELL PERMEABLE CYCLIC PEPTIDE SCAFFOLDS

(71) Applicant: The Regents of the University of California, Oakland, CA (US)

(72) Inventor: Scott Lokey, Santa Cruz, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 16/604,482

(22) PCT Filed: Apr. 23, 2018

(86) PCT No.: PCT/US2018/028832
§ 371 (c)(1),
(2) Date: Oct. 10, 2019

(87) PCT Pub. No.: WO2018/200368
PCT Pub. Date: Nov. 1, 2018

(65) Prior Publication Data
US 2020/0157149 A1 May 21, 2020

Related U.S. Application Data

(60) Provisional application No. 62/489,337, filed on Apr. 24, 2017.

(51) Int. Cl.
*C07K 7/56* (2006.01)
*A61K 38/08* (2019.01)
*C07K 7/06* (2006.01)

(52) U.S. Cl.
CPC ............... *C07K 7/56* (2013.01); *A61K 38/08* (2013.01); *C07K 7/06* (2013.01)

(58) Field of Classification Search
CPC ... C07K 7/56; C07K 7/06; C07K 7/54; C07K 7/00; A61K 38/08; A61K 38/00
See application file for complete search history.

(56) References Cited

U.S. PATENT DOCUMENTS 5,866,540 A 2/1999 Jonczyk et al.
2011/0256567 A1 10/2011 Berthelot et al.

OTHER PUBLICATIONS

Siemion et al (Polish Journal of Chemistry, 1993, 67(5), 877-83) (Year: 1993).*
Wang et al (European Journal of Medicinal Chemistry, 2015, 97, 202-213) (Year: 2015).*
Blaschuk et al (US20050203025A1_STN) (Year: 2005).*
Pubchem, Substance Record for SID 85759687, Available Date: Dec. 15, 2009 [retrieved on Jun. 22, 2018]. Retrieved from the Internet: <URL:https://pubchem.ncbi.nlm.nih.gov/substance/85759687>.
Ahlbach et al. (2015) "Beyond cyclosporine A: conformation-dependent passive membrane permeabilities of cyclic peptide natural products" Future Med Chem, 7(16):2121-2130.
Chu et al. (2015) "Towards understanding cell penetration by stapled peptides" Med Chem Comm, 6(1)111-119.
Darnell (2002) "Transcription factors as targets for cancer therapy" Nat Rev Cancer, 2(10):740-749.
Di (2015) "Strategic approaches to optimizing peptide ADME properties" AAPS J, 17(1):134-143.
Dinca et al. (2016) "Intracellular Delivery of Proteins with Cell-Penetrating Peptides for Therapeutic Uses in Human Disease" Int J Mol Sci, 17(2):263.
Driggers et al. (2008) "The exploration of macrocycles for drug discovery—an underexploited structural class" Nat Rev Drug Discov, 7(7):608-624.
Gao and Kodadek (2015) "Direct comparison of linear and macrocyclic compound libraries as a source of protein igands" ACS Comb Sci, 17(3):190-195.
Hewitt et al. (2015) "Cell-permeable cyclic peptides from synthetic libraries inspired by natural products" J Am Chem Soc, 137(2):715-721.
Hopkins and Groom (2002) "The druggable genome" Nat Rev Drug Discov, 1(9):727-730.
Iyer (2016) "A Review of Stapled Peptides and Small Molecules to Inhibit Protein-Protein Interactions in Cancer" Curr Med Chem, 23(27)3025-3043.
Kubinyi (2003) "Drug research: myths, hype and reality" Nat Rev Drug Discov, 2(8):665-668.
Matsui and Corey (2016) "Non-coding RNAs as drug targets" Nat Rev Drug Discov, 16(3):167-179.
Bask-Andersen et al. (2014) "The druggable genome: Evaluation of drug targets in clinical trials suggests major shifts in molecular class and indication" Annu Rev Pharmacol Toxicol, 54:9-26.
Seigal et al. (2015) "The discovery of macrocyclic XIAP antagonists from a DNA programmed chemistry library, and their optimization to give lead compounds with in vivo antitumor activity" J Med Chem, 58(6):2855-2861.
Sia et al. (2002) "Short constrained peptides that inhibit HIV-I entry" Proc Natl Acad Sci USA, 99(23):14664-14669.
Yamagisni et al. (2011) "Natural product-like macrocyclic N-methyl-peptide inhibitors against a ubiquitin ligase uncovered from a ribosome-expressed de novo library" Chem Biol, 18(12):1562-1570.

* cited by examiner

*Primary Examiner* — Sudhakar Katakam
(74) *Attorney, Agent, or Firm* — Khin K. Chin; Bozicevic, Field & Francis LLP

(57) ABSTRACT

Aspects of the present disclosure include cell permeable cyclic peptide scaffolds that include a hexapeptide composed of naturally or non-naturally occurring amino acids. Pharmaceutical compositions having one or more of the cell permeable cyclic peptide scaffolds and pharmaceutically acceptable excipient are also provided. Methods for using the subject cell permeable cyclic peptide scaffolds are also described.

12 Claims, No Drawings

CELL PERMEABLE CYCLIC PEPTIDE SCAFFOLDS

CROSS-REFERENCE TO RELATED APPLICATION

Pursuant to 35 U.S.C. § 119(e), this application claims priority to the filing date of U.S. Provisional Patent Application Ser. No. 62/489,337 filed on Apr. 24, 2017, the disclosure of which application is incorporated herein by reference.

INTRODUCTION

Certain undruggable targets lack well defined binding pockets. Inhibitors of these undruggable targets may be larger and more complex than typical small molecule drugs. The targets of existing small molecule drugs make up only a small fraction of the protein encoding genome, and it is estimated that the total "druggable" genome (accessible to inhibition by classic small molecules) represents a small fraction of the total number of potential targets. The number of therapeutic targets that have been unexploited due to poor druggability, such as transcription factors and non-coding RNAs, therefore represent a vast opportunity to make therapeutic advances in virtually every disease category.

Macrocylic compounds, such as cyclic peptides exhibit therapeutic potential due to protein-protein interactions (PPIs). Cyclization can often improve potency in peptides as well as proteolytic stability. In addition, the synthesis of cyclic peptides is much more modular and straightforward than the synthesis of organic molecules of similar size and complexity. Large combinatorial libraries of cyclic peptides, derived from methods such as DNA-encoded synthesis, phage display and mRNA-display, have yielded potent inhibitors against a variety of undruggable or challenging targets, such as XIAP10 and E6AP11.

SUMMARY

The present disclosure provides cell permeable cyclic peptide scaffolds, pharmaceutical compositions, and their methods of use, where the cell permeable cyclic peptide scaffolds include a hexapeptide composed of naturally or non-naturally occurring amino acids. In embodiments, the cyclic peptide scaffold is a compound of Formula I:

Cyclo [Z—Y—X-Pro-Y-Phe]   Formula I wherein:
Pro is L-proline or D-proline;
Phe is L-phenylalanine or D-phenylalanine;
X is

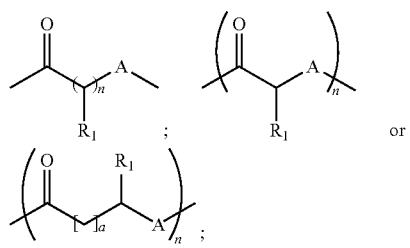

Y is

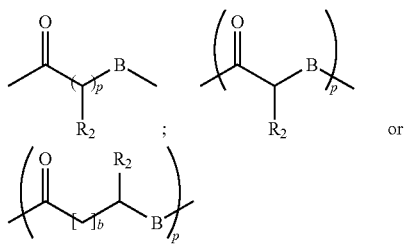

Z is

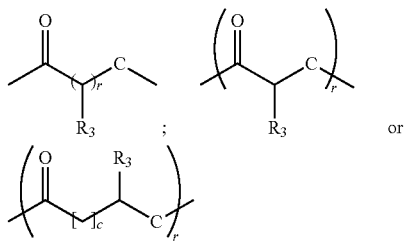

each $R_1$ is independently selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl, or optionally, $R^1$ together with the atoms to which it is bonded form a cycloheteroalkyl or substituted cycloheteroalkyl ring;

each $R_2$ is independently selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl, or optionally, $R^1$ together with the atoms to which it is bonded form a cycloheteroalkyl or substituted cycloheteroalkyl ring;

each $R_3$ is independently selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl, or optionally, $R^1$ together with the atoms to which it is bonded form a cycloheteroalkyl or substituted cycloheteroalkyl ring;

A is selected from —$NR_a$—, —O— or —S—;
B is selected from —$NR_b$—, —O— or —S—;
C is selected from —$NR_c$—, —O— or —S—;
each $R_a$, $R_b$, $R_c$ is independently selected from hydrogen, alkyl, substituted alkyl, aryl and substituted aryl, or
  $R_1$ and $R_a$ together with the atoms to which they are bonded form a cycloheteroalkyl or substituted cycloheteroalkyl ring;
  $R_2$ and $R_b$ together with the atoms to which they are bonded form a cycloheteroalkyl or substituted cycloheteroalkyl ring;
  $R_3$ and $R_c$ together with the atoms to which they are bonded form a cycloheteroalkyl or substituted cycloheteroalkyl ring;
n is an integer from one to 5 and a is an integer from one to 5;
p is an integer from one to 5 and b is an integer from one to 5; and
r is an integer from one to 5 and c is an integer from one to 5;

or a pharmaceutical acceptable salt, solvate or hydrate thereof.

Compositions containing one or more of the subject cell permeable cyclic peptide scaffolds are also provided. In some embodiments, compositions include one or more of the cell permeable cyclic peptide scaffolds described herein, or pharmaceutically acceptable salt, solvate or hydrate thereof and a pharmaceutically acceptable vehicle. Dose units containing one or more of the subject compositions are also provided. A library having a plurality of the cell permeable cyclic peptide scaffolds are also described. For example, the library may include 50 or more of the subject cyclic peptides, each cyclic peptide independently being a compound of Formula I.

DEFINITION OF CERTAIN CHEMICAL TERMINOLOGY

The following terms have the following meaning unless otherwise indicated. Any undefined terms have their art recognized meanings.

As used herein, the term "alkyl" by itself or as part of another substituent refers to a saturated branched or straight-chain monovalent hydrocarbon radical derived by the removal of one hydrogen atom from a single carbon atom of a parent alkane. Typical alkyl groups include, but are not limited to, methyl; ethyl, propyls such as propan-1-yl or propan-2-yl; and butyls such as butan-1-yl, butan-2-yl, 2-methyl-propan-1-yl or 2-methyl-propan-2-yl. In some embodiments, an alkyl group comprises from 1 to 20 carbon atoms. In other embodiments, an alkyl group comprises from 1 to 10 carbon atoms. In still other embodiments, an alkyl group comprises from 1 to 6 carbon atoms, such as from 1 to 4 carbon atoms.

"Alkanyl" by itself or as part of another substituent refers to a saturated branched, straight-chain or cyclic alkyl radical derived by the removal of one hydrogen atom from a single carbon atom of an alkane. Typical alkanyl groups include, but are not limited to, methanyl; ethanyl; propanyls such as propan-1-yl, propan-2-yl (isopropyl), cyclopropan-1-yl, etc.; butanyls such as butan-1-yl, butan-2-yl (sec-butyl), 2-methyl-propan-1-yl (isobutyl), 2-methyl-propan-2-yl (t-butyl), cyclobutan-1-yl, etc.; and the like.

"Alkylene" refers to a branched or unbranched saturated hydrocarbon chain, usually having from 1 to 40 carbon atoms, more usually 1 to 10 carbon atoms and even more usually 1 to 6 carbon atoms. This term is exemplified by groups such as methylene (—$CH_2$—), ethylene (—$CH_2CH_2$—), the propylene isomers (e.g., —$CH_2CH_2CH_2$— and —$CH(CH_3)CH_2$—) and the like.

"Alkenyl" by itself or as part of another substituent refers to an unsaturated branched, straight-chain or cyclic alkyl radical having at least one carbon-carbon double bond derived by the removal of one hydrogen atom from a single carbon atom of an alkene. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like.

"Alkynyl" by itself or as part of another substituent refers to an unsaturated branched, straight-chain or cyclic alkyl radical having at least one carbon-carbon triple bond derived by the removal of one hydrogen atom from a single carbon atom of an alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like.

"Acyl" by itself or as part of another substituent refers to a radical —$C(O)R^{30}$, where $R^{30}$ is hydrogen, alkyl, cycloalkyl, cycloheteroalkyl, aryl, arylalkyl, heteroalkyl, heteroaryl, heteroarylalkyl as defined herein and substituted versions thereof. Representative examples include, but are not limited to formyl, acetyl, cyclohexylcarbonyl, cyclohexylmethylcarbonyl, benzoyl, benzylcarbonyl, piperonyl, succinyl, and malonyl, and the like.

The term "aminoacyl" refers to the group —$C(O)NR^{21}R^{22}$, wherein $R^{21}$ and $R^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{21}$ and $R^{22}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Alkoxy" by itself or as part of another substituent refers to a radical —$OR^{31}$ where $R^{31}$ represents an alkyl or cycloalkyl group as defined herein. Representative examples include, but are not limited to, methoxy, ethoxy, propoxy, butoxy, cyclohexyloxy and the like.

"Alkoxycarbonyl" by itself or as part of another substituent refers to a radical —$C(O)OR^{31}$ where $R^{31}$ represents an alkyl or cycloalkyl group as defined herein. Representative examples include, but are not limited to, methoxycarbonyl, ethoxycarbonyl, propoxycarbonyl, butoxycarbonyl, cyclohexyloxycarbonyl and the like.

"Aryl" by itself or as part of another substituent refers to a monovalent aromatic hydrocarbon radical derived by the removal of one hydrogen atom from a single carbon atom of an aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. In certain embodiments, an aryl group comprises from 6 to 20 carbon atoms. In certain embodiments, an aryl group comprises from 6 to 12 carbon atoms. Examples of an aryl group are phenyl and naphthyl.

"Arylalkyl" by itself or as part of another substituent refers to an acyclic alkyl radical in which one of the hydrogen atoms bonded to a carbon atom, typically a terminal or $sp^3$ carbon atom, is replaced with an aryl group. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylalkenyl and/or arylalkynyl is used.

In certain embodiments, an arylalkyl group is ($C_7$-$C_{30}$) arylalkyl, e.g., the alkanyl, alkenyl or alkynyl moiety of the arylalkyl group is ($C_1$-$C_{10}$) and the aryl moiety is ($C_6$-$C_{20}$). In certain embodiments, an arylalkyl group is ($C_7$-$C_{20}$) arylalkyl, e.g., the alkanyl, alkenyl or alkynyl moiety of the arylalkyl group is ($C_1$-$C_8$) and the aryl moiety is ($C_6$-$C_{12}$).

"Arylaryl" by itself or as part of another substituent, refers to a monovalent hydrocarbon group derived by the removal of one hydrogen atom from a single carbon atom of a ring system in which two or more identical or non-identical aromatic ring systems are joined directly together by a single bond, where the number of such direct ring junctions is one less than the number of aromatic ring systems involved. Typical arylaryl groups include, but are not limited to, biphenyl, triphenyl, phenyl-napthyl, binaphthyl, biphenyl-napthyl, and the like. When the number of carbon atoms in an arylaryl group are specified, the numbers refer to the carbon atoms comprising each aromatic ring. For example, ($C_5$-$C_{14}$) arylaryl is an arylaryl group in which each aromatic ring comprises from 5 to 14 carbons, e.g., biphenyl, triphenyl, binaphthyl, phenylnapthyl, etc. In certain embodiments, each aromatic ring system of an arylaryl group is independently a ($C_5$-$C_{14}$) aromatic. In certain embodiments, each aromatic ring system of an arylaryl group is independently a ($C_5$-$C_{10}$) aromatic. In certain embodiments, each aromatic ring system is identical, e.g., biphenyl, triphenyl, binaphthyl, trinaphthyl, etc.

"Cycloalkyl" by itself or as part of another substituent refers to a saturated or unsaturated cyclic alkyl radical. Where a specific level of saturation is intended, the nomenclature "cycloalkanyl" or "cycloalkenyl" is used. Typical cycloalkyl groups include, but are not limited to, groups derived from cyclopropane, cyclobutane, cyclopentane, cyclohexane and the like. In certain embodiments, the cycloalkyl group is ($C_3$-$C_{10}$) cycloalkyl. In certain embodiments, the cycloalkyl group is ($C_3$-$C_7$) cycloalkyl.

"Cycloheteroalkyl" or "heterocyclyl" by itself or as part of another substituent, refers to a saturated or unsaturated cyclic alkyl radical in which one or more carbon atoms (and any associated hydrogen atoms) are independently replaced with the same or different heteroatom. Typical heteroatoms to replace the carbon atom(s) include, but are not limited to, N, P, O, S, Si, etc. Where a specific level of saturation is intended, the nomenclature "cycloheteroalkanyl" or "cycloheteroalkenyl" is used. Typical cycloheteroalkyl groups include, but are not limited to, groups derived from epoxides, azirines, thiiranes, imidazolidine, morpholine, piperazine, piperidine, pyrazolidine, pyrrolidine, quinuclidine and the like.

"Heteroalkyl, Heteroalkanyl, Heteroalkenyl and Heteroalkynyl" by themselves or as part of another substituent refer to alkyl, alkanyl, alkenyl and alkynyl groups, respectively, in which one or more of the carbon atoms (and any associated hydrogen atoms) are independently replaced with the same or different heteroatomic groups. Typical heteroatomic groups which can be included in these groups include, but are not limited to, —O—, —S—, —S—S—, —O—S—, —NR$^{37}$R$^{38}$—, =N—N=, —N=N—, —N=N—NR$^{39}$R$^{40}$, —PR$^{41}$, —P(O)$_2$—, —POR$^{42}$—, —O—P(O)$_2$—, —S—O—, —S—(O)—, —SO$_2$—, —SnR$^{43}$R$^{44}$— and the like, where R$^{37}$, R$^{38}$, R$^{39}$, R$^{40}$, R$^{41}$, R$^{42}$, R$^{43}$ and R$^{44}$ are independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl or substituted heteroarylalkyl.

"Heteroaryl" by itself or as part of another substituent, refers to a monovalent heteroaromatic radical derived by the removal of one hydrogen atom from a single atom of a heteroaromatic ring system. Typical heteroaryl groups include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, benzodioxole and the like. In certain embodiments, the heteroaryl group is from 5-20 membered heteroaryl. In certain embodiments, the heteroaryl group is from 5-10 membered heteroaryl. In certain embodiments, heteroaryl groups are those derived from thiophene, pyrrole, benzothiophene, benzofuran, indole, pyridine, quinoline, imidazole, oxazole and pyrazine.

"Heteroarylalkyl" by itself or as part of another substituent, refers to an acyclic alkyl radical in which one of the hydrogen atoms bonded to a carbon atom, typically a terminal or sp$^3$ carbon atom, is replaced with a heteroaryl group. Where specific alkyl moieties are intended, the nomenclature heteroarylalkanyl, heteroarylalkenyl and/or heterorylalkynyl is used. In certain embodiments, the heteroarylalkyl group is a 6-30 membered heteroarylalkyl, e.g., the alkanyl, alkenyl or alkynyl moiety of the heteroarylalkyl is 1-10 membered and the heteroaryl moiety is a 5-20-membered heteroaryl. In certain embodiments, the heteroarylalkyl group is 6-20 membered heteroarylalkyl, e.g., the alkanyl, alkenyl or alkynyl moiety of the heteroarylalkyl is 1-8 membered and the heteroaryl moiety is a 5-12-membered heteroaryl.

"Aromatic Ring System" by itself or as part of another substituent, refers to an unsaturated cyclic or polycyclic ring system having a conjugated 7E electron system. Specifically included within the definition of "aromatic ring system" are fused ring systems in which one or more of the rings are aromatic and one or more of the rings are saturated or unsaturated, such as, for example, fluorene, indane, indene, phenalene, etc. Typical aromatic ring systems include, but are not limited to, aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like.

"Heteroaromatic Ring System" by itself or as part of another substituent, refers to an aromatic ring system in which one or more carbon atoms (and any associated hydrogen atoms) are independently replaced with the same or different heteroatom. Typical heteroatoms to replace the carbon atoms include, but are not limited to, N, P, O, S, Si, etc. Specifically included within the definition of "heteroaromatic ring systems" are fused ring systems in which one or more of the rings are aromatic and one or more of the rings are saturated or unsaturated, such as, for example, arsindole, benzodioxan, benzofuran, chromane, chromene, indole, indoline, xanthene, etc. Typical heteroaromatic ring systems include, but are not limited to, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene and the like.

"Substituted" refers to a group in which one or more hydrogen atoms are independently replaced with the same or different substituent(s). Typical substituents include, but are not limited to, alkylenedioxy (such as methylenedioxy), -M, —$R^{60}$, —$O^-$, =O, —$OR^{60}$, —$SR^{60}$, —$S^-$, =S, —$NR^{60}R^{61}$, =$NR^{60}$, —$CF_3$, —CN, —OCN, —SCN, —NO, —$NO_2$, =$N_2$, —$N_3$, —$S(O)_2O^-$, —$S(O)_2OH$, —$S(O)_2R^{60}$, —$OS(O)_2O^-$, —$OS(O)_2R^{60}$, —$P(O)(O^-)_2$, —$P(O)(OR^{60})(O^-)$, —$OP(O)(OR^{60})(OR^{61})$, —$C(O)R^{60}$, —$C(S)R^{60}$, —$C(O)OR^{60}$, —$C(O)NR^{60}R^{61}$, —$C(O)O^-$, —$C(S)OR^{60}$, —$NR^{62}C(O)NR^{60}R^{61}$, —$NR^{62}C(S)NR^{60}R^{61}$, —$NR^{62}C(NR^{63})NR^{60}R^{61}$ and —$C(NR^{62})NR^{60}R^{61}$ where M is halogen; $R^{60}$, $R^{61}$, $R^{62}$ and $R^{63}$ are independently hydrogen, alkyl, substituted alkyl, alkoxy, substituted alkoxy, cycloalkyl, substituted cycloalkyl, cycloheteroalkyl, substituted cycloheteroalkyl, aryl, substituted aryl, heteroaryl or substituted heteroaryl, or optionally $R^{60}$ and $R^{61}$ together with the nitrogen atom to which they are bonded form a cycloheteroalkyl or substituted cycloheteroalkyl ring; and $R^{64}$ and $R^{65}$ are independently hydrogen, alkyl, substituted alkyl, aryl, cycloalkyl, substituted cycloalkyl, cycloheteroalkyl, substituted cycloheteroalkyl, aryl, substituted aryl, heteroaryl or substituted heteroaryl, or optionally $R^{64}$ and $R^{65}$ together with the nitrogen atom to which they are bonded form a cycloheteroalkyl or substituted cycloheteroalkyl ring. In certain embodiments, substituents include -M, —$R^{60}$, =O, $OR^{60}$, —$SR^{60}$, —$S^-$, =S, —$NR^{60}R^{61}$, =$NR^{60}$, —$CF_3$, —CN, —OCN, —SCN, —NO, —$NO_2$, =$N_2$, —$N_3$, —$S(O)_2R^{60}$, —$OS(O)_2O^-$, —$OS(O)_2R^{60}$, —$P(O)(O^-)_2$, —$P(O)(OR^{60})(O^-)$, —$OP(O)(OR^{60})(OR^{61})$, —$C(O)R^{60}$, —$C(S)R^{60}$, —$C(O)OR^{60}$, —$C(O)NR^{60}R^{61}$, —$C(O)O^-$, —$NR^{62}C(O)NR^{60}R^{61}$. In certain embodiments, substituents include -M, —$R^{60}$, =O, —$OR^{60}$, —$SR^{60}$, —$NR^{60}R^{61}$, —$CF_3$, —CN, —$NO_2$, —$S(O)_2R^{60}$, —$P(O)(OR^{60})(O^-)$, —$OP(O)(OR^{60})(OR^{61})$, —$C(O)R^{60}$, —$C(O)OR^{60}$, —$C(O)NR^{60}R^{61}$, —$C(O)O^-$. In certain embodiments, substituents include -M, —$R^{60}$, =O, —$OR^{60}$, —$SR^{60}$, —$NR^{60}R^{61}$, —$CF_3$, —CN, —$NO_2$, —$S(O)_2R^{60}$, —$OP(O)(OR^{60})(OR^{61})$, —$C(O)R^{60}$, —$C(O)OR^{60}$, —$C(O)O^-$, where $R^{60}$, $R^{61}$ and $R^{62}$ are as defined above. For example, a substituted group may bear a methylenedioxy substituent or one, two, or three substituents selected from a halogen atom, a (1-4C)alkyl group and a (1-4C)alkoxy group.

"PK profile" refers to a profile of drug concentration in blood or plasma. Such a profile can be a relationship of drug concentration over time (i.e., a "concentration-time PK profile") or a relationship of drug concentration versus number of doses ingested (i.e., a "concentration-dose PK profile"). A PK profile is characterized by PK parameters.

"PK parameter" refers to a measure of drug concentration in blood or plasma, such as: 1) "drug Cmax", the maximum concentration of drug achieved in blood or plasma; 2) "drug Tmax", the time elapsed following ingestion to achieve Cmax; and 3) "drug exposure", the total concentration of drug present in blood or plasma over a selected period of time, which can be measured using the area under the curve (AUC) of a time course of drug release over a selected period of time (t). Modification of one or more PK parameters provides for a modified PK profile.

"Pharmacodynamic (PD) profile" refers to a profile of the efficacy of a drug in a patient (or subject or user), which is characterized by PD parameters. "PD parameters" include "drug Emax" (the maximum drug efficacy), "drug EC50" (the concentration of drug at 50% of the Emax) and side effects.

"Pharmaceutical composition" refers to at least one compound and can further comprise a pharmaceutically acceptable carrier, with which the compound is administered to a patient.

"Pharmaceutically acceptable salt" refers to a salt of a compound, which possesses the desired pharmacological activity of the compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the compound is replaced by a metal ion, e.g., an alkali metal ion, an alkaline earth ion, or an aluminum ion; or coordinates with an organic base such as ethanolamine, diethanolamine, triethanolamine, N-methylglucamine and the like.

The term "solvate" as used herein refers to a complex or aggregate formed by one or more molecules of a solute, e.g. a prodrug or a pharmaceutically-acceptable salt thereof, and one or more molecules of a solvent. Such solvates are typically crystalline solids having a substantially fixed molar ratio of solute and solvent. Representative solvents include by way of example, water, methanol, ethanol, isopropanol, acetic acid, and the like. When the solvent is water, the solvate formed is a hydrate.

"Pharmaceutically acceptable carrier" refers to a diluent, adjuvant, excipient or vehicle with, or in which a compound is administered.

"Preventing" or "prevention" or "prophylaxis" refers to a reduction in risk of occurrence of a condition, such as pain.

"Prodrug" refers to a derivative of an active agent that requires a transformation within the body to release the active agent. In certain embodiments, the transformation is an enzymatic transformation. Prodrugs are frequently, although not necessarily, pharmacologically inactive until converted to the active agent.

"Promoiety" refers to a form of protecting group that when used to mask a functional group within an active agent converts the active agent into a prodrug. Typically, the promoiety will be attached to the drug via bond(s) that are cleaved by enzymatic or non-enzymatic means in vivo.

"Treating" or "treatment" of any condition, such as pain, refers, in certain embodiments, to ameliorating the condition (i.e., arresting or reducing the development of the condition). In certain embodiments "treating" or "treatment" refers to ameliorating at least one physical parameter, which may not be discernible by the patient. In certain embodiments, "treating" or "treatment" refers to inhibiting the condition, either physically, (e.g., stabilization of a discernible symptom), physiologically, (e.g., stabilization of a physical parameter), or both. In certain embodiments, "treating" or "treatment" refers to delaying the onset of the condition.

"Therapeutically effective amount" means the amount of a compound that, when administered to a patient for preventing or treating a condition such as pain, is sufficient to effect such treatment. The "therapeutically effective amount" will vary depending on the compound, the condition and its severity and the age, weight, etc., of the patient.

DETAILED DESCRIPTION

Before exemplary embodiments of the present invention are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and exemplary methods and materials may now be described. Any and all publications mentioned herein are incorporated herein by reference to disclose and describe the methods and/or materials in connection with which the publications are cited. It is understood that the present disclosure supersedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a membrane anchored polynucleotide" includes a plurality of such membrane-anchored polynucleotides and reference to "the polynucleotide" includes reference to one or more polynucleotides, and so forth.

It is further noted that the claims may be drafted to exclude any element which may be optional. As such, this statement is intended to serve as antecedent basis for use of such exclusive terminology as "solely", "only" and the like in connection with the recitation of claim elements, or the use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed. To the extent such publications may set out definitions of a term that conflicts with the explicit or implicit definition of the present disclosure, the definition of the present disclosure controls.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Cell Permeable Cyclic Peptide Scaffolds

As summarized above, aspects of the present disclosure include cell permeable cyclic peptide scaffolds where the cell permeable cyclic peptide scaffolds include a hexapeptide composed of naturally or non-naturally occurring amino acids. Cell permeable cyclic peptide scaffolds according to some embodiments are permeable into cells. In certain embodiments, the cell permeable cyclic peptide scaffolds described herein are permeable into the nucleus of the cells. In embodiments of the present disclosure, cells permeable to the subject cyclic peptide scaffolds include eukaryotic cells (e.g., mammalian cells) and/or prokaryotic cells (e.g., bacterial cells or archaeal cells). Cells permeable to the subject cyclic peptide scaffolds may be obtained from an in vitro source (e.g., a suspension of cells from laboratory cells grown in culture) or from an in vivo source (e.g., a mammalian subject, a human subject, etc.). In some embodiments, the cells permeable to the subject cyclic peptide scaffolds are obtained from an in vitro source. In vitro sources include, but are not limited to, prokaryotic (e.g., bacterial, archaeal) cell cultures, environmental samples that contain prokaryotic and/or eukaryotic (e.g., mammalian, protest, fungal, etc.) cells, eukaryotic cell cultures (e.g., cultures of established cell lines, cultures of known or purchased cell lines, cultures of immortalized cell lines, cultures of primary cells, cultures of laboratory yeast, etc.), tissue cultures, and the like.

In some embodiments, cells permeable to the subject cyclic peptide scaffolds are obtained from an in vivo source and can include samples obtained from tissues (e.g., cell suspension from a tissue biopsy, cell suspension from a tissue sample, etc.) and/or body fluids (e.g., whole blood, fractionated blood, plasma, serum, saliva, lymphatic fluid, interstitial fluid, etc.). In some cases, cells, fluids, or tissues derived from a subject are cultured, stored, or manipulated prior to evaluation. In vivo sources include living multicellular organisms and can yield non-diagnostic or diagnostic cellular samples.

In certain embodiments the source of the cells is a "mammal" or "mammalian", where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In some instances, the subjects are humans. The methods may be applied to samples obtained from human subjects of both genders and at any stage of development (i.e., neonates, infant, juvenile, adolescent, adult), where in certain embodiments the human subject is a juvenile, adolescent or adult. While the present invention may be applied to samples from a human subject, it is to be understood that the methods may also be carried-out on samples from other animal subjects (that is, in "non-human subjects") such as, but not limited to, birds, mice, rats, dogs, cats, livestock and horses.

In embodiments, the cyclic peptide scaffold is a compound of Formula I:

Cyclo [Z—Y—X-Pro-Y-Phe]   Formula I wherein:
Pro is L-proline or D-proline;
Phe is L-phenylalanine or D-phenylalanine;
X is

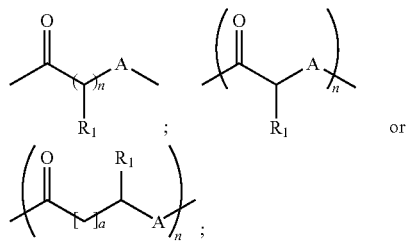

Y is

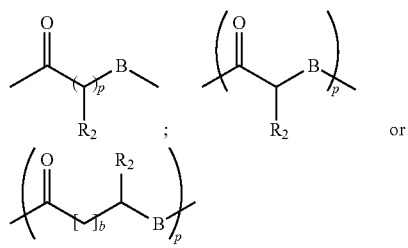

Z is

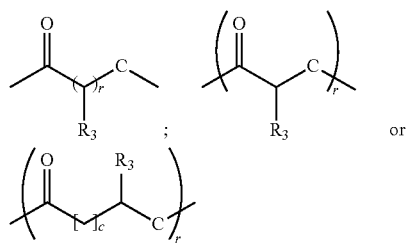

each $R_1$ is independently selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl, or optionally, $R^1$ together with the atoms to which it is bonded form a cycloheteroalkyl or substituted cycloheteroalkyl ring;
each $R_2$ is independently selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl, or optionally, $R^1$ together with the atoms to which it is bonded form a cycloheteroalkyl or substituted cycloheteroalkyl ring;
each $R_3$ is independently selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl, or optionally, $R^1$ together with the atoms to which it is bonded form a cycloheteroalkyl or substituted cycloheteroalkyl ring;
A is selected from $-NR_a-$, $-O-$ or $-S-$;
B is selected from $-NR_b-$, $-O-$ or $-S-$;
C is selected from $-NR_c-$, $-O-$ or $-S-$;
each $R_a$, $R_b$, $R_c$ is independently selected from hydrogen, alkyl, substituted alkyl, aryl and substituted aryl, or
$R_1$ and $R_a$ together with the atoms to which they are bonded form a cycloheteroalkyl or substituted cycloheteroalkyl ring;
$R_2$ and $R_b$ together with the atoms to which they are bonded form a cycloheteroalkyl or substituted cycloheteroalkyl ring;
$R_3$ and $R_c$ together with the atoms to which they are bonded form a cycloheteroalkyl or substituted cycloheteroalkyl ring;
n is an integer from one to 5 and a is an integer from one to 5;
p is an integer from one to 5 and b is an integer from one to 5; and
r is an integer from one to 5 and c is an integer from one to 5;
or a pharmaceutical acceptable salt, solvate or hydrate thereof.

In some embodiments in the compounds of Formula I, each $R_1$ is independently selected from a side chain of an amino acid selected from the group consisting of alanine, arginine, asparagine, aspartic acid, cysteine, glycine, glutamine, glutamic acid, histidine, isoleucine, leucine, lysine, methionine, phenylalanine, proline, serine, threonine, tryptophan, tyrosine and valine. In some instances, each $R_1$ is independently selected from a side chain of glycine, leucine or phenylalanine. In one example, $R_1$ is a side chain of glycine. In another example, $R_1$ is a side chain of leucine. In yet another example, $R_1$ is a side chain of phenylalanine.

In some embodiments in the compounds of Formula I, each $R_2$ is independently selected from a side chain of an amino acid selected from the group consisting of alanine, arginine, asparagine, aspartic acid, cysteine, glycine, glutamine, glutamic acid, histidine, isoleucine, leucine, lysine, methionine, phenylalanine, proline, serine, threonine, tryptophan, tyrosine and valine. In some instances, $R_2$ is selected from a side chain of leucine or glycine. In one example, $R_2$ is a side chain of leucine. In another example, $R_2$ is a side chain of glycine.

In some embodiments in the compounds of Formula I, each $R_3$ is independently selected from a side chain of an amino acid selected from the group consisting of alanine, arginine, asparagine, aspartic acid, cysteine, glycine, glutamine, glutamic acid, histidine, isoleucine, leucine, lysine, methionine, phenylalanine, proline, serine, threonine, tryptophan, tyrosine and valine. In some instances, $R_3$ is independently selected from a side chain of glycine, alanine or phenylalanine. In one example, $R_3$ is a side chain of glycine. In another example, $R_3$ is a side chain of alanine. In yet another example, $R_3$ is a side chain of phenylalanine.

In embodiments, n ranges from 1 to 10, such as where n is 1, such as where n is 2, such as where n is 3, such as where n is 4, such as where n is 5, such as where n is 6, such as where n is 7, such as where n is 8, such as where n is 9 and including where n is 10. In certain embodiments, n ranges from 1 to 5. In one example, n is 1. In this example where n is 1, X may be a naturally occurring amino acid, as described below. In another example, n is 2. In this example where n is 2, X may be a non-naturally occurring amino acid, such as a non-naturally occurring glycine or phenylalanine residue.

In embodiments, p ranges from 1 to 10, such as where p is 1, such as where p is 2, such as where p is 3, such as where p is 4, such as where p is 5, such as where p is 6, such as where p is 7, such as where p is 8, such as where p is 9 and including where p is 10. In certain embodiments, p ranges from 1 to 5. In one example, p is 1. In this example where p is 1, Y may be a naturally occurring amino acid, such as a glycine or leucine residue. In another example, p is 2. In this example where p is 2, Y may be a non-naturally occurring amino acid.

In embodiments, r ranges from 1 to 10, such as where r is 1, such as where r is 2, such as where r is 3, such as where r is 4, such as where r is 5, such as where r is 6, such as where r is 7, such as where r is 8, such as where r is 9 and including where r is 10. In certain embodiments, r ranges from 1 to 5. In one example, r is 1. In this example where r is 1, Z may be a naturally occurring amino acid, as described below. In another example, r is 2. In this example where r is 2, Z may be a non-naturally occurring amino acid, such as a non-naturally occurring glycine or phenylalanine residue.

In certain embodiments, n is 2 and each $R_1$ is selected from a side chain of glycine or phenylalanine. In other embodiments, r is 2 and each $R_3$ is selected from a side chain of glycine or phenylalanine. In still other embodiments, p is 1 and $R_2$ is glycine or leucine.

A may be —$NR_a$—, —O— or —S—. In some instances, A is O. In other instances, A is S. In certain instances, A is $NR_a$ where $R_a$ is hydrogen, alkyl or aryl. In certain embodiments, $R_a$ is hydrogen. In other embodiments, $R_a$ is aryl, such as benzyl. In yet other instances, $R_a$ is alkyl, such as methyl or propyl.

B may be —$NR_b$—, —O— or —S—. In some instances, B is O. In other instances, B is S. In certain instances, B is $NR_b$ where $R_b$ is hydrogen, alkyl or aryl. In certain embodiments, $R_b$ is hydrogen. In other embodiments, $R_b$ is aryl, such as benzyl. In yet other instances, $R_b$ is alkyl, such as methyl or propyl.

C may be —$NR_b$—, —O— or —S—. In some instances, C is O. In other instances, C is S. In certain instances, C is $NR_c$ where $R_c$ is hydrogen, alkyl or aryl. In certain embodiments, $R_c$ is hydrogen. In other embodiments, $R_c$ is aryl, such as benzyl. In yet other instances, $R_c$ is alkyl, such as methyl or propyl.

In some embodiments, X is a residue of a D-amino acid or L-amino acid selected from alanine, arginine, asparagine, aspartic acid, cysteine, glycine, glutamine, glutamic acid, histidine, isoleucine, leucine, lysine, methionine, phenylalanine, β-homophenylalanine, proline, serine, threonine, tryptophan, tyrosine and valine or an N-alkyl derivative thereof. In some instances, X is a D-amino acid selected from alanine, arginine, asparagine, aspartic acid, cysteine, glycine, glutamine, glutamic acid, histidine, isoleucine, leucine, lysine, methionine, phenylalanine, β-homophenylalanine, proline, serine, threonine, tryptophan, tyrosine and valine or an N-alkyl derivative thereof. For example, X may be D-leucine or an N-alkyl derivative thereof, such as N-methyl D-leucine. In other instances, X is an L-amino acid selected from alanine, arginine, asparagine, aspartic acid, cysteine, glycine, glutamine, glutamic acid, histidine, isoleucine, leucine, lysine, methionine, phenylalanine, β-homophenylalanine, proline, serine, threonine, tryptophan, tyrosine and valine or an N-alkyl derivative thereof. For example, X may be L-leucine or an N-alkyl derivative thereof, such as N-methyl L-leucine. In other instances, X is L-β-homophenylalanine or an alkyl derivative thereof. In yet other instances, X is glycine or an N-alkyl derivative thereof, such as N-benzyl glycine.

In some embodiments, Y is a residue of a D-amino acid or L-amino acid selected from alanine, arginine, asparagine, aspartic acid, cysteine, glycine, glutamine, glutamic acid, histidine, isoleucine, leucine, lysine, methionine, phenylalanine, β-homophenylalanine, proline, serine, threonine, tryptophan, tyrosine and valine or an N-alkyl derivative thereof. In some instances, Y is a D-amino acid selected from alanine, arginine, asparagine, aspartic acid, cysteine, glycine, glutamine, glutamic acid, histidine, isoleucine, leucine, lysine, methionine, phenylalanine, β-homophenylalanine, proline, serine, threonine, tryptophan, tyrosine and valine or an N-alkyl derivative thereof. For example, Y may be D-leucine or an N-alkyl derivative thereof, such as N-methyl D-leucine. In other instances, Y is an L-amino acid selected from alanine, arginine, asparagine, aspartic acid, cysteine, glycine, glutamine, glutamic acid, histidine, isoleucine, leucine, lysine, methionine, phenylalanine, β-homophenylalanine, proline, serine, threonine, tryptophan, tyrosine and valine or an N-alkyl derivative thereof. For example, Y may be L-leucine or an N-alkyl derivative thereof, such as N-methyl L-leucine. In yet other instances, Y is glycine or an N-alkyl derivative thereof, such as N-benzyl glycine.

In some embodiments, Z is a residue of a D-amino acid or L-amino acid selected from alanine, arginine, asparagine, aspartic acid, cysteine, glycine, glutamine, glutamic acid, histidine, isoleucine, leucine, lysine, methionine, phenylalanine, β-homophenylalanine, proline, serine, threonine, tryptophan, tyrosine and valine or an N-alkyl derivative thereof. In some instances, Z is a D-amino acid selected from alanine, arginine, asparagine, aspartic acid, cysteine, glycine, glutamine, glutamic acid, histidine, isoleucine, leucine, lysine, methionine, phenylalanine, β-homophenylalanine, proline, serine, threonine, tryptophan, tyrosine and valine or an N-alkyl derivative thereof. For example, Z may be D-alanine or an N-alkyl derivative thereof, such as N-methyl D-leucine. In other instances, Z is an L-amino acid selected from alanine, arginine, asparagine, aspartic acid, cysteine, glycine, glutamine, glutamic acid, histidine, isoleucine, leucine, lysine, methionine, phenylalanine, β-homophenylalanine, proline, serine, threonine, tryptophan, tyrosine and valine or an N-alkyl derivative thereof. For Example, Z may be L-alanine or an N-alkyl derivative thereof, such as N-methyl L-alanine. In yet other instances, Z is L-β-homophenylalanine or an alkyl derivative thereof. In still other instances, Z is glycine or an N-alkyl derivative thereof, such as N-propyl glycine.

In certain embodiments, a cell permeable cyclic peptide scaffold of interest includes a compound of Formula 1:

Formula 1

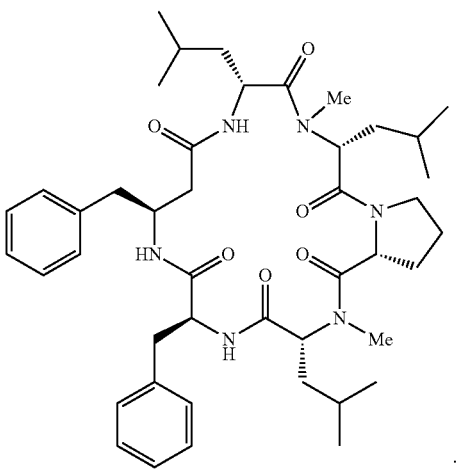

or a pharmaceutical acceptable salt, solvate or hydrate thereof.

In other embodiments, a cell permeable cyclic peptide scaffold of interest includes a compound of Formula 2:

Formula 2

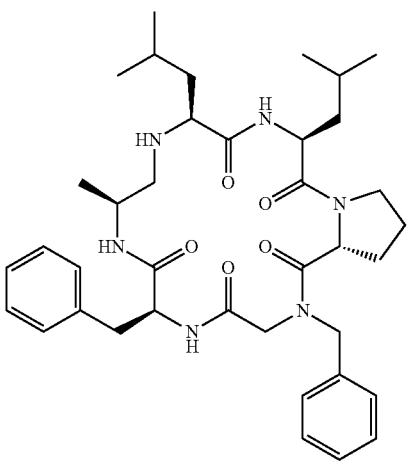

or a pharmaceutical acceptable salt, solvate or hydrate thereof.

In certain embodiments, cell permeable cyclic peptide scaffolds of interest include the compounds as set forth in Table 1, wherein each compound has a cyclic hexapeptide structure, (i.e., cyclo[A-B—C—X—Y—Z]) having a sequence of amino acids as set forth in Table 1, wherein:

LA02=Pro-peptoid

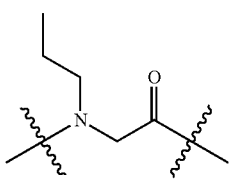 [SMILES: *C(=O)CN(*)CCC]

=Pr-Peptoid (propyl-peptoid)
MA=N-methyl L-alanine
Ma=N-methyl D-alanine
A=L-alanine
a=D-alanine
BHF=L-β-Homophenylalanine

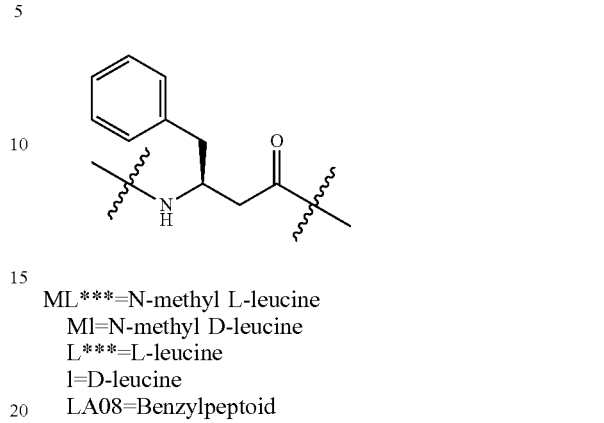

ML***=N-methyl L-leucine
Ml=N-methyl D-leucine
L***=L-leucine
l=D-leucine
LA08=Benzylpeptoid

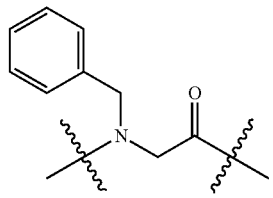 [SMILES: *C(=O)CN(*)Cc1ccccc1]

P=L-proline
p=D-proline
F=L-Phenylalanine.

TABLE 1

| Compound No. | Cyclic Peptide Sequence |
|---|---|
| 1 | BHF, L***, BHF, p, L***, F |
| 2 | BHF, 1, M1, p, M1, F |
| 3 | A, L***, L***, p, LA08, F |
| 4 | BHF, 1, M1, p, 1, F |
| 5 | BHF, L***, 1, P, L***, F |
| 6 | Ma, M1, L***, P, 1, F |
| 7 | A, L***, 1, p, 1, F |
| 8 | A, M1, BHF, P, 1, F |
| 9 | A, M1, 1, p, ML***, F |
| 10 | a, M1, 1, P, M1, F |
| 11 | MA, M1, M1, P, M1, F |
| 12 | A, 1, BHF, p, 1, F |
| 13 | BHF, 1, M1, P, M1, F |
| 14 | MA, M1, M1, P, ML***, F |
| 15 | MA, LA08, M1, P, 1, F |
| 16 | MA, M1, L***, P, M1, F |
| 17 | BHF, 1, ML***, P, ML***, F |
| 18 | BHF, L***, BHF, p, 1, F |
| 19 | MA, LA08, L***, P, M1, F |
| 20 | BHF, M1, M1, P, M1, F |
| 21 | LA02, 1, M1, P, M1, F |
| 22 | a, M1, ML***, p, 1, F |
| 23 | a, L***, L***, p, M1, F |
| 24 | BHF, M1, M1, p, M1, F |
| 25 | BHF, M1, M1, P, M1, F |
| 26 | Ma, L***, ML***, P, M1, F |
| 27 | MA, ML***, LA08, P, LA08, F |
| 28 | MA, M1, M1, P, M1, F |
| 29 | BHF, M1, M1, p, 1, F |
| 30 | a, ML***, L***, p, 1, F |
| 31 | Ma, M1, L***, P, ML***, F |
| 32 | A, M1, M1, p, 1, F |
| 33 | A, M1, L***, p, M1, F |
| 34 | A, LA08, M1, p, L***, F |

TABLE 1-continued

| Compound No. | Cyclic Peptide Sequence |
|---|---|
| 35 | A, M1, L***, P, M1, F |
| 36 | a, M1, BHF, p, M1, F |
| 37 | Ma, ML***, 1, P, ML***, F |
| 38 | A, M1, M1, P, ML***, F |
| 39 | MA, 1, M1, P, ML***, F |
| 40 | A, M1, M1, p, LA08, F |
| 41 | MA, M1, ML***, P, M1, F |
| 42 | BHF, M1, M1, P, M1, F |
| 43 | Ma, M1, 1, P, M1, F |
| 44 | Ma, M1, 1, P, M1, F |
| 45 | LA02, M1, LA08, P, M1, F |
| 46 | LA02, M1, LA08, P, M1, F |
| 47 | A, L***, BHF, p, 1, F |
| 48 | MA, M1, M1, P, L***, F |
| 49 | Ma, M1, M1, P, M1, F |
| 50 | Ma, ML***, M1, P, M1, F |
| 51 | MA, 1, M1, P, 1, F |
| 52 | A, M1, ML***, P, M1, F |
| 53 | A, L***, M1, p, ML***, F |
| 54 | MA, L***, M1, P, M1, F |
| 55 | A, 1, LA08, p, 1, F |
| 56 | Ma, M1, ML***, P, M1, F |
| 57 | MA, M1, LA08, P, ML***, F |
| 58 | A, M1, BHF, P, M1, F |
| 59 | BHF, 1, 1, p, M1, F |
| 60 | a, L***, BHF, p, 1, F |
| 61 | a, L***, LA08, P, L***, F |
| 62 | BHF, L***, 1, p, M1, F |
| 63 | a, M1, L***, p, M1, F |
| 64 | MA, ML***, M1, P, M1, F |
| 65 | Ma, 1, ML***, P, ML***, F |
| 66 | BHF, M1, M1, p, M1, F |
| 67 | MA, ML***, L***, p, M1, F |
| 68 | a, ML***, M1, P, 1, F |
| 69 | A, M1, M1, p, M1, F |
| 70 | A, ML***, BHF, P, L***, F |
| 71 | A, L***, L***, p, 1, F |
| 72 | Ma, ML***, M1, P, L***, F |
| 73 | A, 1, ML***, p, 1, F |
| 74 | A, M1, BHF, p, M1, F |
| 75 | MA, 1, M1, P, LA08, F |
| 76 | A, M1, BHF, p, M1, F |
| 77 | LA02, M1, BHF, P, L***, F |
| 78 | A, M1, 1, p, LA08, F |
| 79 | A, M1, 1, p, M1, F |
| 80 | A, M1, L***, p, ML***, F |
| 81 | Ma, M1, L***, P, LA08, F |
| 82 | A, 1, M1, p, M1, F |
| 83 | a, M1, L***, P, M1, F |
| 84 | MA, M1, M1, P, M1, F |
| 85 | A, L***, LA08, p, M1, F |
| 86 | MA, L***, M1, P, M1, F |
| 87 | MA, M1, M1, P, LA08, F |
| 88 | LA02, M1, L***, P, 1, F |
| 89 | Ma, L***, M1, P, ML***, F |
| 90 | Ma, ML***, L***, P, M1, F |
| 91 | A, M1, BHF, P, M1, F |
| 92 | Ma, M1, M1, P, M1, F |
| 93 | a, M1, BHF, p, M1, F |
| 94 | BHF, M1, M1, P, M1, F |
| 95 | a, M1, L***, P, ML***, F |
| 96 | BHF, L***, LA08, P, L***, F |
| 97 | A, M1, L***, p, 1, F |
| 98 | LA02, M1, BHF, P, M1, F |
| 99 | A, M1, L***, P, ML***, F |
| 100 | MA, ML***, 1, P, M1, F |
| 101 | Ma, M1, M1, P, M1, F |
| 102 | a, M1, BHF, p, M1, F |
| 103 | LA02, M1, M1, P, M1, F |
| 104 | MA, M1, ML***, P, LA08, F |
| 105 | LA02, L***, 1, P, L***, F |
| 106 | MA, 1, L***, p, ML***, F |
| 107 | Ma, L***, M1, p, ML***, F |
| 108 | MA, M1, 1, P, ML***, F |
| 109 | MA, L***, M1, P, ML***, F |
| 110 | BHF, L***, M1, P, L***, F |
| 111 | Ma, ML***, M1, P, LA08, F |
| 112 | a, LA08, M1, p, L***, F |
| 113 | LA02, 1, M1, P, M1, F |
| 114 | A, L***, LA08, p, 1, F |
| 115 | a, ML***, M1, P, LA08, F |
| 116 | a, 1, LA08, p, 1, F |
| 117 | a, M1, LA08, p, 1, F |
| 118 | A, 1, L***, P, L***, F |
| 119 | LA02, M1, M1, p, M1, F |
| 120 | A, 1, L***, p, L***, F |
| 121 | LA02, M1, 1, P, 1, F |
| 122 | a, M1, BHF, P, M1, F |
| 123 | A, L***, LA08, p, LA08, F |
| 124 | A, 1, L***, p, M1, F |
| 125 | a, M1, L***, p, 1, F |
| 126 | Ma, M1, BHF, P, M1, F |
| 127 | Ma, M1, 1, P, LA08, F |
| 128 | MA, 1, ML***, P, ML***, F |
| 129 | BHF, M1, M1, p, M1, F |
| 130 | Ma, M1, 1, P, 1, F |
| 131 | Ma, LA08, M1, P, L***, F |
| 132 | Ma, L***, M1, P, L***, F |
| 133 | a, M1, 1, P, ML***, F |
| 134 | BHF, 1, M1, P, 1, F |
| 135 | BHF, 1, L***, p, ML***, F |
| 136 | a, M1, LA08, p, ML***, F |
| 137 | MA, 1, M1, P, M1, F |
| 138 | MA, M1, 1, P, M1, F |
| 139 | BHF, M1, M1, P, M1, F |
| 140 | A, L***, M1, P, L***, F |
| 141 | a, M1, L***, P, ML***, F |
| 142 | MA, L***, M1, P, 1, F |
| 143 | LA02, M1, 1, P, M1, F |
| 144 | Ma, LA08, 1, P, M1, F |
| 145 | MA, M1, BHF, P, M1, F |
| 146 | BHF, 1, 1, P, ML***, F |
| 147 | Ma, L***, 1, P, ML***, F |
| 148 | Ma, L***, 1, P, L***, F |
| 149 | MA, 1, LA08, P, ML***, F |
| 150 | BHF, M1, M1, p, M1, F |
| 151 | MA, M1, 1, P, M1, F |
| 152 | MA, M1, 1, P, M1, F |
| 153 | LA02, L***, L***, P, M1, F |
| 154 | a, LA08, M1, P, M1, F |
| 155 | MA, M1, M1, P, 1, F |
| 156 | MA, M1, M1, P, 1, F |
| 157 | Ma, 1, M1, P, M1, F |
| 158 | LA02, 1, L***, p, M1, F |
| 159 | Ma, LA08, M1, P, M1, F |
| 160 | LA02, 1, L***, P, ML***, F |
| 161 | A, 1, ML***, p, M1, F |
| 162 | Ma, M1, BHF, P, M1, F |
| 163 | a, LA08, ML***, P, M1, F |
| 164 | LA02, L***, 1, P, M1, F |
| 165 | Ma, M1, BHF, P, M1, F |
| 166 | A, M1, M1, p, M1, F |
| 167 | a, ML***, L***, p, ML***, F |
| 168 | LA02, M1, M1, P, M1, F |
| 169 | A, M1, ML***, p, L***, F |
| 170 | MA, 1, 1, P, LA08, F |
| 171 | a, M1, L***, P, LA08, F |
| 172 | A, L***, ML***, p, M1, F |
| 173 | BHF, 1, M1, p, L***, F |
| 174 | a, LA08, M1, p, ML***, F |
| 175 | MA, ML***, LA08, P, LA08, F |
| 176 | BHF, ML***, LA08, p, ML***, F |
| 177 | BHF, L***, M1, p, 1, F |
| 178 | LA02, 1, ML***, P, M1, F |
| 179 | Ma, ML***, L***, p, M1, F |
| 180 | MA, 1, ML***, P, LA08, F |
| 181 | A, ML***, M1, P, M1, F |
| 182 | Ma, 1, ML***, P, 1, F |
| 183 | BHF, L***, 1, p, LA08, F |
| 184 | LA02, L***, 1, p, ML***, F |
| 185 | LA02, ML***, 1, p, ML***, F |
| 186 | Ma, 1, ML***, p, ML***, F |
| 187 | MA, M1, L***, p, ML***, F |
| 188 | LA02, M1, BHF, P, M1, F |

TABLE 1-continued

| Compound No. | Cyclic Peptide Sequence |
|---|---|
| 189 | LA02, ML***, 1, p, LA08, F |
| 190 | MA, 1, LA08, p, ML***, F |
| 191 | Ma, L***, M1, P, LA08, F |
| 192 | Ma, M1, M1, P, 1, F |
| 193 | A, L***, BHF, P, ML***, F |
| 194 | a, M1, 1, p, ML***, F |
| 195 | A, M1, M1, P, L***, F |
| 196 | a, M1, M1, P, 1, F |
| 197 | A, M1, ML***, p, 1, F |
| 198 | Ma, L***, M1, P, 1, F |
| 199 | A, L***, L***, p, M1, F |
| 200 | A, 1, L***, P, LA08, F |
| 201 | A, ML***, M1, P, ML***, F |
| 202 | LA02, M1, M1, P, 1, F |
| 203 | BHF, M1, M1, p, M1, F |
| 204 | LA02, M1, M1, p, M1, F |
| 205 | LA02, M1, M1, P, M1, F |
| 206 | LA02, 1, L***, P, 1, F |
| 207 | a, M1, M1, p, M1, F |
| 208 | a, LA08, ML***, P, ML***, F |
| 209 | MA, 1, ML***, p, 1, F |
| 210 | a, L***, LA08, p, 1, F |
| 211 | Ma, ML***, M1, p, M1, F |
| 212 | A, M1, M1, p, M1, F |
| 213 | A, LA08, L***, P, M1, F |
| 214 | LA02, 1, L***, p, ML***, F |
| 215 | Ma, ML***, L***, P, 1, F |
| 216 | BHF, L***, M1, p, L***, F |
| 217 | LA02, L***, M1, P, M1, F |
| 218 | LA02, 1, 1, P, L***, F |
| 219 | a, M1, BHF, P, M1, F |
| 220 | BHF, 1, ML***, P, 1, F |
| 221 | BHF, L***, 1, p, 1, F |
| 222 | A, 1, M1, P, LA08, F |
| 223 | A, M1, 1, P, LA08, F |
| 224 | BHF, 1, M1, P, M1, F |
| 225 | MA, L***, M1, P, LA08, F |
| 226 | LA02, M1, 1, p, ML***, F |
| 227 | a, ML***, L***, P, M1, F |
| 228 | A, M1, BHF, P, M1, F |
| 229 | Ma, LA08, 1, P, 1, F |
| 230 | LA02, ML***, ML***, p, M1, F |
| 231 | a, 1, 1, P, L***, F |
| 232 | A, ML***, 1, P, LA08, F |
| 233 | LA02, M1, ML***, P, M1, F |
| 234 | Ma, M1, BHF, P, M1, F |
| 235 | BHF, 1, L***, P, ML***, F |
| 236 | A, 1, ML***, P, ML***, F |
| 237 | LA02, M1, M1, p, M1, F |
| 238 | Ma, M1, M1, p, M1, F |
| 239 | BHF, L***, 1, P, 1, F |
| 240 | a, M1, M1, P, M1, F |
| 241 | A, 1, LA08, p, LA08, F |
| 242 | A, L***, 1, p, LA08, F |
| 243 | A, 1, ML***, P, M1, F |
| 244 | A, ML***, LA08, P, M1, F |
| 245 | BHF, M1, 1, p, 1, F |
| 246 | BHF, 1, L***, P, L***, F |
| 247 | LA02, M1, L***, P, M1, F |
| 248 | BHF, L***, 1, P, ML***, F |
| 249 | LA02, ML***, L***, P, 1, F |
| 250 | A, 1, ML***, P, LA08, F |
| 251 | A, M1, ML***, P, LA08, F |
| 252 | Ma, LA08, 1, P, M1, F |
| 253 | Ma, L***, LA08, P, ML***, F |
| 254 | LA02, M1, ML***, P, ML***, F |
| 255 | MA, 1, L***, p, M1, F |
| 256 | a, L***, M1, p, ML***, F |
| 257 | A, M1, LA08, p, ML***, F |
| 258 | MA, 1, M1, p, 1, F |
| 259 | LA02, L***, 1, p, M1, F |
| 260 | Ma, 1, L***, p, M1, F |
| 261 | BHF, 1, ML***, p, 1, F |
| 262 | MA, L***, 1, P, ML***, F |
| 263 | A, M1, 1, P, M1, F |
| 264 | A, L***, M1, P, LA08, F |
| 265 | a, M1, 1, P, LA08, F |
| 266 | LA02, M1, M1, P, M1, F |
| 267 | Ma, L***, LA08, P, M1, F |
| 268 | LA02, M1, LA08, P, LA08, F |
| 269 | A, 1, ML***, p, ML***, F |
| 270 | a, 1, L***, p, M1, F |
| 271 | LA02, M1, BHF, p, M1, F |
| 272 | BHF, M1, M1, P, M1, F |
| 273 | MA, M1, M1, P, M1, F |
| 274 | A, ML***, LA08, p, LA08, F |
| 275 | MA, 1, M1, P, L***, F |
| 276 | LA02, 1, BHF, P, L***, F |
| 277 | MA, M1, M1, P, M1, F |
| 278 | BHF, 1, 1, p, 1, F |
| 279 | BHF, 1, 1, p, 1, F |
| 280 | Ma, 1, BHF, P, LF |
| 281 | A, ML***, 1, p, LA08, F |
| 282 | MA, 1, ML***, p, ML***, F |
| 283 | a, ML***, LA08, P, ML***, F |
| 284 | BHF, L***, L***, p, M1, F |
| 285 | A, M1, M1, P, M1, F |
| 286 | A, M1, M1, P, M1, F |
| 287 | A, LA08, BHF, p, 1, F |
| 288 | a, LA08, M1, P, L***, F |
| 289 | a, 1, ML***, p, M1, F |
| 290 | BHF, 1, 1, p, LA08, F |
| 291 | LA02, 1, LA08, P, M1, F |
| 292 | a, LA08, M1, P, L***, F |
| 293 | LA02, M1, ML***, p, 1, F |
| 294 | MA, M1, ML***, p, M1, F |
| 295 | BHF, M1, L***, P, 1, F |
| 296 | BHF, M1, 1, P, 1, F |
| 297 | MA, LA08, ML***, p, 1, F |
| 298 | a, M1, L***, p, L***, F |
| 299 | A, M1, LA08, P, L***, F |
| 300 | A, 1, LA08, P, L***, F |
| 301 | BHF, LA08, 1, P, M1, F |
| 302 | Ma, ML***, M1, P, LA08, F |
| 303 | BHF, LA08, L***, P, L***, F |
| 304 | LA02, M1, BHF, p, M1, F |
| 305 | A, M1, M1, P, M1, F |
| 306 | BHF, 1, LA08, p, 1, F |
| 307 | A, M1, ML***, P, ML***, F |
| 308 | MA, ML***, LA08, p, M1, F |
| 309 | A, M1, M1, p, M1, F |
| 310 | BHF, 1, 1, P, M1, F |
| 311 | MA, M1, BHF, p, M1, F |
| 312 | BHF, L***, P, 1, F |
| 313 | MA, 1, L***, p, LF |
| 314 | BHF, 1, BHF, p, M1, F |
| 315 | a, M1, 1, P, M1, F |
| 316 | BHF, LBHF, p, LF |
| 317 | A, M1, LA08, P, ML***, F |
| 318 | a, 1, L***, p, LA08, F |
| 319 | LA02, ML***, M1, P, 1, F |
| 320 | BHF, 1, LA08, P, 1, F |
| 321 | A, ML***, L***, p, 1, F |
| 322 | MA, 1, L***, p, LA08, F |
| 323 | BHF, M1, L***, p, L***, F |
| 324 | A, LA08, L***, P, M1, F |
| 325 | A, M1, LA08, p, M1, F |
| 326 | LA02, M1, M1, p, M1, F |
| 327 | A, M1, L***, p, LA08, F |
| 328 | LA02, M1, L***, p, 1, F |
| 329 | Ma, L***, 1, P, M1, F |
| 330 | A, LA08, 1, P, LA08, F |
| 331 | LA02, M1, 1, p, M1, F |
| 332 | A, M1, BHF, p, M1, F |
| 333 | A, 1, BHF, p, ML***, F |
| 334 | LA02, ML***, M1, p, M1, F |
| 335 | LA02, 1, L***, p, 1, F |
| 336 | MA, M1, LA08, p, ML***, F |
| 337 | LA02, ML***, M1, P, M1, F |
| 338 | LA02, M1, BHF, P, M1, F |
| 339 | LA02, LA08, M1, P, 1, F |
| 340 | LA02, M1, M1, P, LA08, F |
| 341 | LA02, ML***, LA08, p, M1, F |
| 342 | Ma, LA08, M1, p, 1, F |

TABLE 1-continued

| Compound No. | Cyclic Peptide Sequence |
|---|---|
| 343 | Ma, ML***, LA08, P, LA08, F |
| 344 | A, 1, LA08, P, M1, F |
| 345 | a, ML***, M1, P, LA08, F |
| 346 | LA02, ML***, 1, P, 1, F |
| 347 | MA, M1, LA08, P, LA08, F |
| 348 | BHF, 1, L***, P, ML***, F |
| 349 | A, L***, M1, P, ML***, F |
| 350 | Ma, M1, M1, p, M1, F |
| 351 | Ma, M1, L***, p, L***, F |
| 352 | a, LA08, M1, p, M1, F |
| 353 | a, ML***, LA08, p, MLF |
| 354 | A, M1, M1, P, LA08, F |
| 355 | Ma, LA08, 1, p, ML***, F |
| 356 | BHF, 1, L***, p, M1, F |
| 357 | a, LA08, ML***, p, ML***, F |
| 358 | A, M1, ML***, p, LA08, F |
| 359 | BHF, 1, L***, P, LA08, F |
| 360 | BHF, M1, BHF, P, L***, F |
| 361 | MA, M1, M1, P, M1, F |
| 362 | A, M1, 1, P, L***, F |
| 363 | BHF, 1, ML***, P, 1, F |
| 364 | Ma, M1, ML***, p, M1, F |
| 365 | MA, 1, ML***, P, 1, F |
| 366 | LA02, L***, M1, p, 1, F |
| 367 | LA02, ML***, 1, p, LA08, F |
| 368 | A, LA08, L***, P, LA08, F |
| 369 | a, ML***, 1, p, LF |
| 370 | LA02, ML***, 1, p, M1, F |
| 371 | BHF, M1, BHF, P, 1, F |
| 372 | a, LA08, LA08, P, ML***, F |
| 373 | MA, M1, M1, P, M1, F |
| 374 | A, LA08, 1, p, 1, F |
| 375 | MA, 1, BHF, p, M1, F |
| 376 | MA, M1, 1, P, 1, F |
| 377 | Ma, M1, BHF, P, L***, F |
| 378 | A, M1, M1, P, M1, F |
| 379 | A, MLBHF, p, LF |
| 380 | LA02, 1, LA08, p, M1, F |
| 381 | MA, 1, ML***, P, M1, F |
| 382 | BHF, L***, 1, P, M1, F |
| 383 | LA02, L***, LA08, P, M1, F |
| 384 | a, M1, 1, p, M1, F |
| 385 | Ma, 1, LA08, p, M1, F |
| 386 | MA, 1, L***, P, ML***, F |
| 387 | a, ML***, LA08, p, ML***, F |
| 388 | BHF, ML***, LA08, P, M1, F |
| 389 | A, ML***, 1, P, M1, F |
| 390 | Ma, ML***, 1, P, LA08, F |
| 391 | a, 1, BHF, p, ML***, F |
| 392 | A, LA08, ML***, P, LA08, F |
| 393 | a, 1, ML***, p, LA08, F |
| 394 | Ma, 1, LA08, P, LA08, F |
| 395 | Ma, M1, L***, p, ML***, F |
| 396 | Ma, M1, M1, P, M1, F |
| 397 | A, LA08, M1, P, LA08, F |
| 398 | BHF, 1, 1, P, 1, F |
| 399 | MA, 1, LA08, p, ML***, F |
| 400 | Ma, L***, LA08, P, LA08, F |
| 401 | LA02, L***, L***, p, M1, F |
| 402 | A, LA08, LA08, p, L***, F |
| 403 | LA02, 1, 1, P, M1, F |
| 404 | Ma, M1, LA08, p, ML***, F |
| 405 | Ma, ML***, L***, p, LA08, F |
| 406 | BHF, LA08, M1, p, M1, F |
| 407 | BHF, 1, L***, p, ML***, F |
| 408 | MA, L***, BHF, p, L***, F |
| 409 | LA02, M1, M1, p, M1, F |
| 410 | A, L***, 1, P, LA08, F |
| 411 | LA02, 1, BHF, P, M1, F |
| 412 | a, ML***, ML***, P, LA08, F |
| 413 | A, LL***, P, MLF |
| 414 | MA, ML***, LA08, p, LA08, F |
| 415 | MA, 1, M1, p, LA08, F |
| 416 | A, 1, LA08, p, ML***, F |
| 417 | Ma, 1, ML***, p, 1, F |
| 418 | Ma, LA08, L***, p, M1, F |
| 419 | A, 1, M1, P, M1, F |
| 420 | A, M1, M1, p, M1, F |
| 421 | a, ML***, 1, P, ML***, F |
| 422 | LA02, L***, L***, P, LA08, F |
| 423 | MA, L***, L***, P, M1, F |
| 424 | LA02, 1, ML***, p, L***, F |
| 425 | a, MLBHF, P, L***, F |
| 426 | LA02, M1, LA08, p, M1, F |
| 427 | BHF, LA08, 1, P, L***, F |
| 428 | A, L***, LA08, P, LA08, F |
| 429 | A, M1, LA08, p, M1, F |
| 430 | BHF, M1, M1, p, M1, F |
| 431 | MA, 1, LA08, P, M1, F |
| 432 | MA, LA08, L***, p, ML***, F |
| 433 | a, L***, M1, P, L***, F |
| 434 | Ma, M1, M1, P, M1, F |
| 435 | a, LA08, L***, P, L***, F |
| 436 | A, ML***, 1, P, L***, F |
| 437 | MA, L***, 1, P, MLF |
| 438 | LA02, 1, ML***, P, LA08, F |
| 439 | A, M1, M1, P, 1, F |
| 440 | MA, M1, ML***, p, LA08, F |
| 441 | MA, M1, L***, p, LA08, F |
| 442 | A, 1, LA08, P, ML***, F |
| 443 | a, LA08, 1, P, L***, F |
| 444 | LA02, LA08, ML***, P, M1, F |
| 445 | MA, ML***, L***, P, LA08, F |
| 446 | LA02, M1, ML***, P, 1, F |
| 447 | LA02, 1, ML***, p, 1, F |
| 448 | A, M1, LA08, p, L***, F |
| 449 | Ma, 1, ML***, p, LA08, F |
| 450 | MA, 1, 1, p, 1, F |
| 451 | A, MLL***, p, L***, F |
| 452 | Ma, 1, L***, P, ML***, F |
| 453 | a, LA08, L***, P, LA08, F |
| 454 | BHF, ML***, ML***, P, LA08, F |
| 455 | LA02, LA08, 1, p, L***, F |
| 456 | LA02, LA08, M1, P, LA08, F |
| 457 | A, M1, M1, P, M1, F |
| 458 | a, M1, LA08, P, M1, F |
| 459 | Ma, L***, LA08, p, M1, F |
| 460 | a, 1, ML***, p, ML***, F |
| 461 | A, L***, LA08, p, L***, F |
| 462 | LA02, M1, LA08, p, M1, F |
| 463 | Ma, LA08, 1, p, ML***, F |
| 464 | a, M1, M1, P, M1, F |
| 465 | A, ML***, 1, P, ML***, F |
| 466 | MA, M1, 1, p, M1, F |
| 467 | Ma, 1, L***, p, MLF |
| 468 | MA, LA08, ML***, p, ML***, F |
| 469 | LA02, 1, BHF, P, L***, F |
| 470 | BHF, MLBHF, p, LF |
| 471 | MA, 1, L***, P, M1, F |
| 472 | LA02, L***, ML***, p, M1, F |
| 473 | LA02, M1, L***, p, M1, F |
| 474 | LA02, 1, L***, p, LA08, F |
| 475 | Ma, LA08, L***, p, ML***, F |
| 476 | Ma, M1, LA08, p, 1, F |
| 477 | LA02, M1, LA08, p, LA08, F |
| 478 | MA, LA08, L***, p, L***, F |
| 479 | LA02, LA08, L***, p, L***, F |
| 480 | BHF, 1, ML***, P, ML***, F |
| 481 | Ma, 1, LA08, P, M1, F |
| 482 | a, M1, LA08, P, ML***, F |
| 483 | BHF, LA08, 1, p, 1, F |
| 484 | A, LA08, 1, P, L***, F |
| 485 | LA02, M1, L***, P, LA08, F |
| 486 | A, L***, LA08, P, M1, F |
| 487 | A, 1, 1, p, 1, F |
| 488 | LA02, M1, LA08, p, M1, F |
| 489 | LA02, M1, BHF, p, 1, F |
| 490 | BHF, 1, ML***, P, L***, F |
| 491 | BHF, M1, BHF, P, M1, F |
| 492 | BHF, ML***, LA08, P, 1, F |
| 493 | BHF, L***, BHF, P, L***, F |
| 494 | a, LA08, BHF, P, 1, F |
| 495 | MA, M1, LA08, p, M1, F |
| 496 | BHF, 1, LA08, P, L***, F |

TABLE 1-continued

| Compound No. | Cyclic Peptide Sequence |
|---|---|
| 497 | A, MLBHF, p, MLF |
| 498 | BHF, LML***, p, 1, F |
| 499 | MA, LA08, 1, P, 1, F |
| 500 | LA02, ML***, 1, p, 1, F |
| 501 | A, 1, L***, P, ML***, F |
| 502 | Ma, M1, M1, P, M1, F |
| 503 | MA, M1, LA08, p, ML***, F |
| 504 | BHF, M1, BHF, p, M1, F |
| 505 | LA02, LA08, L***, P, ML***, F |
| 506 | a, ML***, LA08, P, LF |
| 507 | LA02, M1, LA08, p, 1, F |
| 508 | A, ML***, BHF, p, LF |
| 509 | LA02, ML***, ML***, p, 1, F |
| 510 | A, 1, ML***, p, L***, F |
| 511 | A, 1, L***, p, ML***, F |
| 512 | a, ML***, L***, p, M1, F |
| 513 | Ma, ML***, LA08, p, LA08, F |
| 514 | A, ML***, M1, P, 1, F |
| 515 | LA02, M1, ML***, P, LA08, F |
| 516 | LA02, LA08, 1, P, 1, F |
| 517 | LA02, 1, M1, P, 1, F |
| 518 | LA02, 1, M1, p, 1, F |
| 519 | BHF, M1, BHF, P, 1, F |
| 520 | LA02, M1, LA08, p, LA08, F |
| 521 | LA02, ML***, M1, p, 1, F |
| 522 | LA02, 1, LA08, p, ML***, F |
| 523 | MA, M1, L***, P, ML***, F |
| 524 | A, 1, LA08, P, 1, F |
| 525 | A, LA08, M1, P, M1, F |
| 526 | a, MLL***, P, LF |
| 527 | a, M1, ML***, p, LA08, F |
| 528 | LA02, 1, 1, p, ML***, F |
| 529 | A, 1, 1, P, LA08, F |
| 530 | Ma, 1, L***, p, LA08, F |
| 531 | LA02, LA08, M1, P, 1, F |
| 532 | A, M1, ML***, p, L***, F |
| 533 | Ma, 1, L***, p, 1, F |
| 534 | MA, M1, ML***, P, L***, F |
| 535 | LA02, 1, ML***, p, ML***, F |
| 536 | LA02, M1, M1, p, M1, F |
| 537 | LA02, L***, LA08, P, LA08, F |
| 538 | MA, M1, M1, p, M1, F |
| 539 | LA02, M1, LA08, P, ML***, F |
| 540 | LA02, LA08, 1, p, 1, F |
| 541 | LA02, LA08, 1, p, M1, F |
| 542 | a, ML***, L***, P, 1, F |
| 543 | Ma, L***, M1, p, LA08, F |
| 544 | Ma, L***, L***, P, M1, F |
| 545 | MA, 1, LA08, P, M1, F |
| 546 | BHF, LA08, M1, p, 1, F |
| 547 | A, LA08, LA08, P, LA08, F |
| 548 | a, LA08, BHF, P, L***, F |
| 549 | LA02, M1, L***, p, LA08, F |
| 550 | A, LA08, ML***, P, LA08, F |
| 551 | Ma, M1, LA08, P, LA08, F |
| 552 | a, LA08, M1, P, LA08, F |
| 553 | BHF, LA08, M1, P, L***, F |
| 554 | a, M1, 1, p, LA08, F |
| 555 | Ma, M1, ML***, p, LA08, F |
| 556 | A, LA08, M1, P, 1, F |
| 557 | A, L***, L***, P, LA08, F |
| 558 | LA02, ML***, BHF, p, 1, F |
| 559 | a, M1, BHF, P, ML***, F |
| 560 | BHF, 1, BHF, p, LA08, F |
| 561 | MA, 1, 1, P, 1, F |
| 562 | BHF, M1, L***, P, ML***, F |
| 563 | BHF, 1, BHF, p, ML***, F |
| 564 | A, LA08, BHF, P, L***, F |
| 565 | a, ML***, M1, p, LA08, F |
| 566 | LA02, ML***, L***, p, M1, F |
| 567 | Ma, L***, ML***, P, 1, F |
| 568 | LA02, ML***, 1, p, L***, F |
| 569 | A, LA08, LA08, p, LA08, F |
| 570 | BHF, L***, M1, P, 1, F |
| 571 | MA, M1, M1, p, M1, F |
| 572 | BHF, ML***, 1, p, M1, F |
| 573 | MA, 1, ML***, p, L***, F |
| 574 | A, ML***, LA08, p, LA08, F |
| 575 | A, L***, L***, P, MLF |
| 576 | MA, 1, 1, P, M1, F |
| 577 | MA, 1, BHF, p, 1, F |
| 578 | a, LA08, M1, P, 1, F |
| 579 | MA, 1, L***, P, LA08, F |
| 580 | a, M1, L***, p, LA08, F |
| 581 | BHF, M1, L***, P, L***, F |
| 582 | LA02, M1, BHF, P, M1, F |
| 583 | LA02, 1, LA08, p, L***, F |
| 584 | a, L***, M1, P, ML***, F |
| 585 | BHF, LA08, L***, p, 1, F |
| 586 | Ma, M1, LA08, P, LA08, F |
| 587 | BHF, L***, L***, P, M1, F |
| 588 | BHF, 1, LA08, p, M1, F |
| 589 | BHF, 1, L***, p, LA08, F |
| 590 | A, 1, ML***, P, 1, F |
| 591 | BHF, 1, L***, p, LA08, F |
| 592 | A, LA08, L***, P, LA08, F |
| 593 | LA02, LA08, M1, p, LA08, F |
| 594 | a, M1, BHF, p, ML***, F |
| 595 | LA02, L***, L***, p, LA08, F |
| 596 | Ma, M1, L***, p, LA08, F |
| 597 | BHF, LL***, p, 1, F |
| 598 | MA, LA08, M1, p, 1, F |
| 599 | LA02, M1, LA08, p, ML***, F |
| 600 | A, 1, M1, p, ML***, F |
| 601 | BHF, MLL***, P, MLF |
| 602 | A, LA08, M1, P, LA08, F |
| 603 | a, LA08, 1, p, ML***, F |
| 604 | Ma, 1, 1, P, 1, F |
| 605 | Ma, M1, M1, p, M1, F |
| 606 | Ma, LBHF, P, ML***, F |
| 607 | Ma, 1, L***, P, LF |
| 608 | MA, ML***, L***, p, LF |
| 609 | A, LA08, 1, p, L***, F |
| 610 | a, L***, M1, P, LA08, F |
| 611 | LA02, LA08, BHF, P, M1, F |
| 612 | a, ML***, 1, p, LA08, F |
| 613 | LA02, LA08, M1, p, M1, F |
| 614 | MA, 1, LA08, p, M1, F |
| 615 | LA02, M1, BHF, P, M1, F |
| 616 | LA02, M1, L***, P, LA08, F |
| 617 | a, MLBHF, p, LF |
| 618 | LA02, LA08, BHF, P, 1, F |
| 619 | LA02, M1, M1, p, M1, F |
| 620 | BHF, 1, BHF, P, ML***, F |
| 621 | MA, LA08, L***, p, 1, F |
| 622 | Ma, LA08, L***, P, 1, F |
| 623 | a, LA08, L***, P, LA08, F |
| 624 | A, L***, M1, p, M1, F |
| 625 | LA02, ML***, LA08, p, LA08, F |
| 626 | A, 1, LA08, P, LA08, F |
| 627 | LA02, LA08, ML***, P, 1, F |
| 628 | BHF, M1, BHF, p, M1, F |
| 629 | LA02, ML***, L***, p, 1, F |
| 630 | Ma, L***, M1, p, 1, F |
| 631 | LA02, M1, LA08, p, ML***, F |
| 632 | MA, M1, M1, p, M1, F |
| 633 | a, ML***, 1, p, M1, F |
| 634 | A, ML***, L***, P, 1, F |
| 635 | Ma, 1, 1, p, 1, F |
| 636 | BHF, M1, M1, P, M1, F |
| 637 | LA02, LA08, LA08, p, 1, F |
| 638 | a, ML***, 1, P, M1, F |
| 639 | a, M1, BHF, P, 1, F |
| 640 | a, LA08, LA08, P, LA08, F |
| 641 | LA02, 1, LA08, P, LA08, F |
| 642 | LA02, 1, 1, P, LA08, F |
| 643 | LA02, M1, M1, p, LA08, F |
| 644 | LA02, M1, LA08, p, LA08, F |
| 645 | MA, 1, LA08, P, LA08, F |
| 646 | A, 1, LA08, p, M1, F |
| 647 | A, L***, M1, P, M1, F |
| 648 | Ma, ML***, BHF, p, LA08, F |
| 649 | MA, ML***, BHF, p, LA08, F |
| 650 | MA, L***, ML***, p, LA08, F |

TABLE 1-continued

| Compound No. | Cyclic Peptide Sequence |
|---|---|
| 651 | a, M1, M1, P, M1, F |
| 652 | Ma, M1, M1, p, M1, F |
| 653 | a, L***, M1, P, 1, F |
| 654 | A, M1, LA08, p, M1, F |
| 655 | Ma, L***, 1, P, LA08, F |
| 656 | Ma, 1, 1, P, L***, F |
| 657 | Ma, 1, 1, p, LA08, F |
| 658 | MA, M1, LA08, p, LA08, F |
| 659 | BHF, M1, 1, p, M1, F |
| 660 | LA02, LA08, 1, P, LA08, F |
| 661 | LA02, 1, BHF, p, L***, F |
| 662 | LA02, LA08, LA08, p, 1, F |
| 663 | LA02, 1, M1, p, M1, F |
| 664 | LA02, M1, ML***, p, ML***, F |
| 665 | A, LA08, ML***, P, M1, F |
| 666 | a, M1, ML***, p, L***, F |
| 667 | a, LA08, LA08, p, 1, F |
| 668 | BHF, ML***, LA08, P, 1, F |
| 669 | BHF, L***, ML***, p, LA08, F |
| 670 | BHF, 1, BHF, P, 1, F |
| 671 | MA, L***, LA08, p, LA08, F |
| 672 | A, 1, LA08, p, L***, F |
| 673 | BHF, 1, 1, P, LA08, F |
| 674 | a, L***, LA08, P, LA08, F |
| 675 | LA02, LA08, LA08, P, LA08, F |
| 676 | LA02, LA08, LA08, P, L***, F |
| 677 | LA02, L***, L***, p, LA08, F |
| 678 | a, L***, 1, P, M1, F |
| 679 | BHF, LA08, 1, P, 1, F |
| 680 | A, L***, 1, P, M1, F |
| 681 | a, M1, 1, P, 1, F |
| 682 | LA02, ML***, LA08, P, LA08, F |
| 683 | Ma, ML***, 1, P, 1, F |
| 684 | a, M1, LA08, p, LA08, F |
| 685 | A, L***, 1, p, M1, F |
| 686 | Ma, LA08, L***, P, 1, F |
| 687 | LA02, ML***, LA08, P, LA08, F |
| 688 | BHF, L***, BHF, p, MLF |
| 689 | a, ML***, 1, P, L***, F |
| 690 | Ma, L***, M1, p, L***, F |
| 691 | LA02, 1, BHF, p, M1, F |
| 692 | Ma, 1, BHF, p, LA08, F |
| 693 | A, L***, LA08, P, 1, F |
| 694 | Ma, L***, LA08, P, LA08, F |
| 695 | a, L***, 1, P, ML***, F |
| 696 | A, LA08, 1, P, LA08, F |
| 697 | BHF, L***, M1, P, ML***, F |
| 698 | LA02, ML***, BHF, P, L***, F |
| 699 | BHF, L***, ML***, P, 1, F |
| 700 | LA02, M1, L***, p, ML***, F |
| 701 | LA02, M1, ML***, p, M1, F |
| 702 | BHF, L***, LA08, P, LF |
| 703 | MA, 1, BHF, p, LA08, F |
| 704 | A, L***, LA08, p, 1, F |
| 705 | LA02, L***, BHF, P, L***, F |
| 706 | MA, M1, 1, P, LA08, F |
| 707 | LA02, 1, M1, p, M1, F |
| 708 | a, LBHF, p, 1, F |
| 709 | BHF, L***, L***, P, LA08, F |
| 710 | LA02, LA08, BHF, P, L***, F |
| 711 | a, LA08, 1, P, LA08, F |
| 712 | a, M1, 1, P, L***, F |
| 713 | BHF, 1, BHF, P, LA08, F |
| 714 | LA02, L***, 1, P, 1, F |
| 715 | BHF, LA08, BHF, P, L***, F |
| 716 | A, LA08, ML***, P, ML***, F |
| 717 | a, 1, LA08, P, LA08, F |
| 718 | LA02, 1, L***, p, L***, F |
| 719 | BHF, M1, BHF, P, 1, F |
| 720 | a, 1BHF, p, M1, F |
| 721 | BHF, LA08, 1, P, M1, F |
| 722 | A, ML***, LA08, p, M1, F |
| 723 | MA, L***, L***, p, MLF |
| 724 | A, M1, BHF, P, L***, F |
| 725 | BHF, L***, ML***, P, LA08, F |
| 726 | BHF, LA08, M1, p, M1, F |
| 727 | LA02, L***, BHF, p, 1, F |
| 728 | a, LA08, ML***, p, ML***, F |
| 729 | A, LA08, ML***, P, 1, F |
| 730 | A, M1, M1, p, M1, F |
| 731 | LA02, LA08, L***, p, LA08, F |
| 732 | BHF, 1, ML***, p, LA08, F |
| 733 | Ma, L***, L***, p, M1, F |
| 734 | LA02, M1, M1, P, M1, F |
| 735 | BHF, M1, 1, P, ML***, F |
| 736 | Ma, M1, L***, p, 1, F |
| 737 | BHF, LA08, ML***, P, L***, F |
| 738 | BHF, ML***, M1, p, M1, F |
| 739 | a, 1, LA08, p, ML***, F |
| 740 | a, M1, LA08, P, L***, F |
| 741 | LA02, LA08, 1, p, L***, F |
| 742 | BHF, 1, L***, p, ML***, F |
| 743 | LA02, L***, p, L***, F |
| 744 | A, 1, 1, p, LA08, F |
| 745 | LA02, L***, M1, p, LA08, F |
| 746 | MA, ML***, BHF, p, LA08, F |
| 747 | a, L***, L***, P, LA08, F |
| 748 | BHF, L***, 1, P, LA08, F |
| 749 | LA02, M1, 1, p, LA08, F |
| 750 | MA, M1, L***, p, 1, F |
| 751 | a, LA08, 1, p, M1, F |
| 752 | LA02, L***, 1, p, 1, F |
| 753 | Ma, M1, BHF, P, 1, F |
| 754 | MA, LA08, ML***, P, M1, F |
| 755 | MA, LA08, 1, p, LA08, F |
| 756 | Ma, M1, BHF, p, 1, F |
| 757 | BHF, M1, L***, P, LA08, F |
| 758 | LA02, M1, BHF, p, M1, F |
| 759 | BHF, 1, 1, p, L***, F |
| 760 | a, LA08, BHF, p, ML***, F |
| 761 | a, M1, M1, P, M1, F |
| 762 | BHF, MLL***, p, 1, F |
| 763 | a, LA08, 1, P, LA08, F |
| 764 | Ma, L***, 1, p, LA08, F |
| 765 | LA02, ML***, M1, P, LA08, F |
| 766 | BHF, LA08, BHF, p, 1, F |
| 767 | A, L***, M1, P, 1, F |
| 768 | A, M1, 1, P, 1, F |
| 769 | Ma, ML***, LA08, p, M1, F |
| 770 | A, ML***, LA08, p, 1, F |
| 771 | a, LA08, LA08, p, 1, F |
| 772 | BHF, L***, LA08, p, M1, F |
| 773 | Ma, 1, BHF, P, MLF |
| 774 | A, 1, BHF, P, 1, F |
| 775 | a, ML***, BHF, P, LA08, F |
| 776 | A, M1, LA08, p, M1, F |
| 777 | BHF, M1, LA08, P, M1, F |
| 778 | LA02, 1, M1, P, M1, F |
| 779 | Ma, LA08, ML***, P, 1, F |
| 780 | LA02, M1, 1, p, 1, F |
| 781 | BHF, ML***, LA08, p, LA08, F |
| 782 | MA, 1, LA08, p, LA08, F |
| 783 | Ma, ML***, BHF, p, 1, F |
| 784 | Ma, LA08, BHF, P, L***, F |
| 785 | LA02, 1, 1, p, LA08, F |
| 786 | a, L***, 1, p, M1, F |
| 787 | Ma, 1, L***, P, LA08, F |
| 788 | LA02, ML***, 1, P, L***, F |
| 789 | LA02, 1, BHF, p, L***, F |
| 790 | BHF, LA08, L***, p, M1, F |
| 791 | LA02, M1, LA08, p, ML***, F |
| 792 | MA, M1, M1, P, M1, F |
| 793 | BHF, LA08, LA08, p, 1, F |
| 794 | A, 1, 1, P, M1, F |
| 795 | a, L***, 1, p, LA08, F |
| 796 | a, M1, BHF, P, LA08, F |
| 797 | MA, L***, 1, P, L***, F |
| 798 | BHF, M1, 1, P, M1, F |
| 799 | a, LA08, M1, p, 1, F |
| 800 | A, 1, BHF, P, ML***, F |
| 801 | A, LA08, M1, p, L***, F |
| 802 | MA, M1, LA08, p, L***, F |
| 803 | MA, M1, BHF, P, M1, F |
| 804 | A, LA08, 1, P, 1, F |

TABLE 1-continued

| Compound No. | Cyclic Peptide Sequence |
|---|---|
| 805 | A, 1, L***, P, L***, F |
| 806 | BHF, M1, ML***, P, ML***, F |
| 807 | MA, M1, M1, P, M1, F |
| 808 | MA, ML***, BHF, p, LF |
| 809 | A, 1, BHF, P, LA08, F |
| 810 | a, 1, BHF, P, ML***, F |
| 811 | a, LA08, M1, P, LA08, F |
| 812 | BHF, M1, 1, p, ML***, F |
| 813 | a, L***, M1, p, 1, F |
| 814 | a, 1, BHF, P, LA08, F |
| 815 | a, LA08, L***, p, L***, F |
| 816 | LA02, 1, 1, P, M1, F |
| 817 | A, 1, BHF, p, M1, F |
| 818 | BHF, L***, LA08, p, LA08, F |
| 819 | LA02, 1, LA08, p, LA08, F |
| 820 | MA, L***, L***, p, LA08, F |
| 821 | BHF, L***, M1, p, ML***, F |
| 822 | A, 1, 1, P, L***, F |
| 823 | MA, L***, BHF, p, LA08, F |
| 824 | BHF, M1, L***, p, ML***, F |
| 825 | BHF, L***, L***, P, 1, F |
| 826 | a, M1, M1, P, M1, F |
| 827 | MA, 1, M1, P, 1, F |
| 828 | Ma, L***, 1, p, M1, F |
| 829 | LA02, LA08, LA08, p, LA08, F |
| 830 | LA02, L***, L***, P, 1, F |
| 831 | LA02, 1, 1, p, L***, F |
| 832 | A, L***, 1, P, 1, F |
| 833 | MA, 1, LA08, P, L***, F |
| 834 | a, 1, L***, P, LA08, F |
| 835 | Ma, 1, LA08, P, LA08, F |
| 836 | LA02, L***, LA08, p, L***, F |
| 837 | a, LA08, 1, P, 1, F |
| 838 | Ma, 1, ML***, p, L***, F |
| 839 | BHF, M1, M1, P, 1, F |
| 840 | a, ML***, BHF, P, 1, F |
| 841 | BHF, M1, 1, p, ML***, F |
| 842 | LA02, LA08, LA08, P, L***, F |
| 843 | Ma, 1, LA08, p, LA08, F |
| 844 | MA, LA08, LA08, P, LA08, F |
| 845 | a, 1, LA08, P, M1, F |
| 846 | BHF, L***, M1, P, LA08, F |
| 847 | A, 1, 1, p, ML***, F |
| 848 | MA, L***, L***, P, MLF |
| 849 | Ma, LA08, BHF, p, ML***, F |
| 850 | LA02, M1, BHF, p, M1, F |
| 851 | A, M1, BHF, P, 1F |
| 852 | A, ML***, 1, p, L***, F |
| 853 | A, ML***, 1, p, M1, F |
| 854 | A, 1, ML***, P, 1, F |
| 855 | a, M1, BHF, p, M1, F |
| 856 | MA, 1, BHF, P, ML***, F |
| 857 | MA, M1, M1, P, M1, F |
| 858 | BHF, M1, M1, P, M1, F |
| 859 | MA, M1, 1, p, L***, F |
| 860 | a, LA08, LA08, p, LA08, F |
| 861 | BHF, L***, BHF, P, ML***, F |
| 862 | Ma, 1, 1, P, M1, F |
| 863 | BHF, ML***, LA08, p, M1, F |
| 864 | a, L***, L***, P, M1, F |
| 865 | a, 1, LA08, p, M1, F |
| 866 | a, L***, 1, p, 1, F |
| 867 | Ma, L***, LA08, p, LA08, F |
| 868 | LA02, 1, BHF, P, LA08, F |
| 869 | LA02, 1, 1, p, M1, F |
| 870 | A, L***, L***, P, M1, F |
| 871 | MA, 1, 1, P, 1, F |
| 872 | BHF, ML***, LA08, p, 1, F |
| 873 | A, ML***, 1, P, 1, F |
| 874 | BHF, M1, M1, P, 1, F |
| 875 | MA, ML***, L***, P, 1, F |
| 876 | a, LA08, ML***, p, LA08, F |
| 877 | LA02, ML***, L***, p, LA08, F |
| 878 | a, M1, LA08, P, 1, F |
| 879 | MA, M1, BHF, p, 1, F |
| 880 | LA02, LA08, L***, p, ML***, F |
| 881 | A, M1, 1, p, L***, F |
| 882 | Ma, M1, LA08, p, LA08, F |
| 883 | LA02, ML***, LA08, p, L***, F |
| 884 | a, M1, 1, p, 1, F |
| 885 | MA, M1, L***, P, 1, F |
| 886 | LA02, M1, 1, P, LA08, F |
| 887 | Ma, 1, BHF, P, L***, F |
| 888 | A, L***, 1, P, 1, F |
| 889 | BHF, 1, LA08, P, LA08, F |
| 890 | Ma, 1, BHF, p, M1, F |
| 891 | Ma, 1, BHF, P, LA08, F |
| 892 | A, 1, BHF, P, L***, F |
| 893 | BHF, M1, 1, P, LA08, F |
| 894 | a, L***, M1, p, L***, F |
| 895 | MA, M1, 1, p, 1, F |
| 896 | BHF, M1, LA08, P, ML***, F |
| 897 | a, M1, BHF, P, M1, F |
| 898 | a, M1, BHF, P, LA08, F |
| 899 | BHF, ML***, LA08, p, M1, F |
| 900 | a, L***, 1, P, LA08, F |
| 901 | a, M1, LA08, p, L***, F |
| 902 | LA02, L***, ML***, p, LA08, F |
| 903 | MA, LA08, BHF, p, 1, F |
| 904 | BHF, LA08, LA08, P, 1, F |
| 905 | BHF, M1, L***, P, M1, F |
| 906 | Ma, LA08, BHF, p, 1, F |
| 907 | Ma, M1, M1, p, M1, F |
| 908 | BHF, LA08, M1, P, LA08, F |
| 909 | LA02, M1, M1, p, 1, F |
| 910 | MA, ML***, 1, p, LA08, F |
| 911 | A, LA08, LA08, p, L***, F |
| 912 | a, L***, 1, P, 1, F |
| 913 | BHF, LA08, BHF, P, 1, F |
| 914 | a, M1, M1, p, M1, F |
| 915 | Ma, LA08, 1, p, L***, F |
| 916 | BHF, M1, ML***, P, M1, F |
| 917 | A, 1, 1, P, 1, F |
| 918 | a, ML***, 1, P, 1, F |
| 919 | MA, 1, M1, p, L***, F |
| 920 | Ma, LA08, LA08, P, LA08, F |
| 921 | a, 1, M1, p, 1, F |
| 922 | Ma, 1, 1, P, LA08, F |
| 923 | LA02, M1, BHF, p, M1, F |
| 924 | Ma, L***, ML***, p, 1, F |
| 925 | MA, M1, M1, P, M1, F |
| 926 | A, M1, 1, p, 1, F |
| 927 | Ma, LA08, 1, p, L***, F |
| 928 | Ma, M1, M1, P, M1, F |
| 929 | a, 1, LA08, P, 1, F |
| 930 | LA02, ML***, BHF, p, M1, F |
| 931 | a, L***, LA08, P, 1, F |
| 932 | MA, ML***, BHF, P, 1, F |
| 933 | MA, L***, 1, P, LA08, F |
| 934 | a, M1, M1, p, 1, F |
| 935 | LA02, ML***, BHF, p, LA08, F |
| 936 | LA02, L***, L***, p, 1, F |
| 937 | BHF, M1, LA08, P, ML***, F |
| 938 | Ma, M1, BHF, P, M1, F |
| 939 | a, 1, L***, P, ML***, F |
| 940 | BHF, ML***, LA08, P, LA08, F |
| 941 | A, 1, 1, p, 1, F |
| 942 | MA, 1, LA08, p, L***, F |
| 943 | a, 1, M1, P, M1, F |
| 944 | MA, M1, L***, P, L***, F |
| 945 | Ma, 1, 1, p, ML***, F |
| 946 | Ma, 1, BHF, p, M1, F |
| 947 | Ma, LA08, BHF, p, M1, F |
| 948 | MA, M1, M1, p, 1, F |
| 949 | A, 1, 1, p, M1, F |
| 950 | a, M1, LA08, p, M1, F |
| 951 | MA, 1, ML***, P, L***, F |
| 952 | a, L***, BHF, p, 1, F |
| 953 | BHF, ML***, M1, P, LA08, F |
| 954 | a, 1, 1, P, LA08, F |
| 955 | MA, 1, 1, P, M1, F |
| 956 | BHF, ML***, LA08, P, LA08, F |
| 957 | MA, LA08, BHF, P, 1, F |
| 958 | BHF, LA08, LA08, p, M1, F |

TABLE 1-continued

| Compound No. | Cyclic Peptide Sequence |
|---|---|
| 959 | A, 1, BHF, P, M1, F |
| 960 | a, L***, M1, p, M1, F |
| 961 | MA, 1, BHF, P, L***, F |
| 962 | BHF, L***, LA08, P, LA08, F |
| 963 | MA, L***, LA08, P, 1, F |
| 964 | BHF, M1, LA08, p, 1, F |
| 965 | a, 1, M1, p, ML***, F |
| 966 | Ma, M1, BHF, p, LA08, F |
| 967 | BHF, ML***, LA08, p, ML***, F |
| 968 | BHF, 1, LA08, p, LA08, F |
| 969 | MA, 1, 1, P, L***, F |
| 970 | MA, M1, BHF, P, M1, F |
| 971 | MA, M1, LA08, P, 1, F |
| 972 | a, LA08, 1, p, 1, F |
| 973 | MA, 1, BHF, P, M1, F |
| 974 | MA, 1, BHF, P, M1, F |
| 975 | a, ML***, 1, p, ML***, F |
| 976 | Ma, LA08, LA08, p, LA08, F |
| 977 | a, 1, LA08, p, L***, F |
| 978 | a, L***, L***, p, LF |
| 979 | MA, LA08, LA08, p, LA08, F |
| 980 | BHF, ML***, LA08, P, MLF |
| 981 | BHF, ML***, M1, P, M1, F |
| 982 | MA, 1, BHF, p, L***, F |
| 983 | MA, 1, L***, p, L***, F |
| 984 | BHF, LA08, L***, P, LA08, F |
| 985 | BHF, 1, LA08, P, LA08, F |
| 986 | BHF, ML***, ML***, P, LA08, F |
| 987 | Ma, L***, BHF, P, L***, F |
| 988 | BHF, LA08, BHF, P, M1, F |
| 989 | MA, M1, BHF, P, 1, F |
| 990 | Ma, 1, 1, p, M1, F |
| 991 | a, L***, 1, p, 1, F |
| 992 | BHF, M1, BHF, p, M1, F |
| 993 | BHF, ML***, LA08, p, LA08, F |
| 994 | MA, 1, 1, p, LA08, F |
| 995 | MA, LA08, L***, P, 1, F |
| 996 | Ma, LA08, 1, p, 1, F |
| 997 | BHF, LA08, LA08, p, L***, F |
| 998 | Ma, L***, 1, P, 1, F |
| 999 | MA, M1, M1, p, 1, F |
| 1000 | BHF, M1, 1, p, LA08, F |
| 1001 | Ma, M1, M1, P, 1, F |
| 1002 | a, 1, BHF, P, M1, F |
| 1003 | Ma, L***, 1, P, LA08, F |
| 1004 | MA, L***, 1, p, LA08, F |
| 1005 | BHF, ML***, ML***, P, M1, F |
| 1006 | MA, LA08, L***, p, LA08, F |
| 1007 | BHF, ML***, LA08, p, M1, F |
| 1008 | MA, L***, BHF, p, 1, F |
| 1009 | a, 1, 1, p, 1, F |
| 1010 | MA, L***, L***, p, 1, F |
| 1011 | Ma, M1, M1, p, 1, F |
| 1012 | MA, 1, 1, p, L***, F |
| 1013 | LA02, M1, ML***, p, L***, F |
| 1014 | BHF, M1, L***, p, M1, F |
| 1015 | Ma, L***, 1, p, 1, F |
| 1016 | a, 1, 1, P, M1, F |
| 1017 | BHF, LA08, LA08, p, M1, F |
| 1018 | Ma, M1, M1, p, 1, F |
| 1019 | MA, 1, L***, P, L***, F |
| 1020 | Ma, L***, L***, P, 1, F |
| 1021 | a, 1, 1, p, LA08, F |
| 1022 | Ma, 1, 1, p, LA08, F |
| 1023 | a, 1, LA08, p, L***, F |
| 1024 | a, 1, M1, p, M1, F |
| 1025 | a, 1, 1, P, 1, F |
| 1026 | LA02, LA08, BHF, p, M1, F |
| 1027 | BHF, LA08, BHF, P, LA08, F |
| 1028 | BHF, ML***, BHF, P, LA08, F |
| 1029 | Ma, 1, L***, p, L***, F |
| 1030 | BHF, M1, ML***, p, M1, F |
| 1031 | MA, M1, BHF, P, L***, F |
| 1032 | a, LA08, LA08, p, L***, F |
| 1033 | BHF, M1, BHF, P, LA08, F |
| 1034 | a, L***, 1, P, 1, F |
| 1035 | MA, 1, 1, P, LA08, F |
| 1036 | BHF, M1, LA08, P, LA08, F |
| 1037 | BHF, ML***, LA08, p, ML***, F |
| 1038 | BHF, LA08, LA08, P, LA08, F |
| 1039 | BHF, LA08, L***, p, ML***, F |
| 1040 | a, 1, 1, P, 1, F |
| 1041 | a, 1, 1, p, M1, F |
| 1042 | BHF, M1, BHF, P, ML***, F |
| 1043 | Ma, M1, M1, p, 1, F |
| 1044 | Ma, L***, 1, p, L***, F |
| 1045 | a, 1, L***, p, L***, F |
| 1046 | BHF, LA08, BHF, p, M1, F |
| 1047 | Ma, L***, L***, p, LF |
| 1048 | a, L***, 1, p, L***, F |
| 1049 | MA, L***, L***, P, 1, F |
| 1050 | BHF, LA08, LA08, p, LA08, F |
| 1051 | MA, LA08, M1, p, LA08, F |
| 1052 | Ma, MLBHF, p, M1, F |
| 1053 | Ma, 1, 1, P, 1, F |
| 1054 | MA, 1, 1, P, 1, F |
| 1055 | MA, 1, 1, p, 1, F |
| 1056 | LA02, L***, L***, p, L***, F |
| 1057 | BHF, LA08, BHF, p, LA08, F |
| 1058 | a, M1, BHF, p, M1, F |
| 1059 | LA02, M1, BHF, P, M1, F |
| 1060 | BHF, ML***, BHF, p, ML***, F |
| 1061 | BHF, M1, BHF, P, M1, F |
| 1062 | a, M1, BHF, p, M1, F |
| 1063 | BHF, M1, BHF, p, M1, F |
| 1064 | BHF, M1, BHF, p, M1, F |
| 1065 | A, M1, M1, p, M1, F |
| 1066 | a, M1, M1, p, M1, F |
| 1067 | A, M1, M1, P, M1, F |
| 1068 | a, M1, M1, P, M1, F |
| 1069 | MA, M1, M1, P, M1, F |
| 1070 | Ma, M1, M1, P, M1, F |
| 1071 | Ma, 1, 1, p, 1, F |
| 1072 | MA, 1, 1, p, 1, F |
| 1073 | MA, 1, 1, p, 1, F |
| 1074 | Ma, M1, BHF, P, M1, F |
| 1075 | a, 1, 1, p, 1, F |
| 1076 | MA, LA08, LA08, P, LA08, F |
| 1077 | A, M1, BHF, p, M1, F |
| 1078 | MA, M1, BHF, P, MLF |
| 1079 | a, M1, M1, p, M1, F |
| 1080 | BHF, 1, 1, P, M1, F |
| 1081 | LA02, M1, BHF, P, ML***, F |
| 1082 | Ma, M1, M1, P, ML***, F |
| 1083 | LA02, ML***, BHF, p, M1, F |
| 1084 | Ma, ML***, ML***, P, 1, F |
| 1085 | MA, L***, LA08, P, LA08, F |
| 1086 | Ma, L***, L***, p, ML***, F |
| 1087 | MA, M1, M1, P, ML***, F |
| 1088 | MA, M1, M1, P, ML***, F |
| 1089 | Ma, L***, ML***, p, M1, F |
| 1090 | MA, 1, 1, p, M1, F |
| 1091 | Ma, L***, L***, p, ML***, F |
| 1092 | a, 1, ML***, P, M1, F |
| 1093 | MA, 1, 1, P, ML***, F |
| 1094 | A, LA08, BHF, p, L***, F |
| 1095 | MA, M1, ML***, P, 1, F |
| 1096 | LA02, ML***, ML***, P, LA08, F |
| 1097 | MA, 1, 1, p, ML***, F |
| 1098 | BHF, 1, ML***, p, ML***, F |
| 1099 | A, M1, BHF, p, L***, F |
| 1100 | a, ML***, ML***, p, 1, F |
| 1101 | Ma, M1, ML***, p, L***, F |
| 1102 | MA, M1, LA08, P, M1, F |
| 1103 | Ma, L***, M1, p, 1, F |
| 1104 | A, 1, M1, p, M1, F |
| 1105 | Ma, ML***, LA08, p, 1, F |
| 1106 | BHF, ML***, L***, p, M1, F |
| 1107 | BHF, ML***, L***, p, M1, F |
| 1108 | A, 1, BHF, p, L***, F |
| 1109 | a, ML***, LA08, P, ML***, F |
| 1110 | MA, L***, LA08, p, LA08, F |
| 1111 | a, ML***, ML***, p, 1, F |
| 1112 | A, ML***, BHF, P, 1, F |

TABLE 1-continued

| Compound No. | Cyclic Peptide Sequence |
|---|---|
| 1113 | MA, L***, 1, p, 1, F |
| 1114 | Ma, 1, L***, p, ML***, F |
| 1115 | BHF, ML***, L***, P, M1, F |
| 1116 | Ma, 1, 1, p, L***, F |
| 1117 | BHF, ML***, L***, p, LA08, F |
| 1118 | Ma, L***, ML***, p, LA08, F |
| 1119 | MA, M1, M1, P, 1, F |
| 1120 | Ma, M1, LA08, p, L***, F |
| 1121 | A, ML***, BHF, P, LA08, F |
| 1122 | BHF, ML***, L***, P, LA08, F |
| 1123 | BHF, M1, L***, p, LA08, F |
| 1124 | LA02, ML***, L***, P, LA08, F |
| 1125 | a, 1, 1, p, ML***, F |
| 1126 | MA, 1, BHF, P, LA08, F |
| 1127 | BHF, ML***, LA08, p, LA08, F |
| 1128 | Ma, M1, M1, P, ML***, F |
| 1129 | LA02, L***, L***, p, LA08, F |
| 1130 | Ma, M1, 1, p, M1, F |
| 1131 | MA, M1, ML***, p, M1, F |
| 1132 | MA, ML***, ML***, P, 1, F |
| 1133 | a, 1, 1, p, L***, F |
| 1134 | a, ML***, BHF, p, LA08, F |
| 1135 | Ma, ML***, LA08, p, M1, F |
| 1136 | LA02, M1, 1, P, M1, F |
| 1137 | a, M1, 1, p, L***, F |
| 1138 | a, ML***, 1, p, L***, F |
| 1139 | a, 1, 1, P, ML***, F |
| 1140 | Ma, 1, L***, P, L***, F |
| 1141 | a, L***, ML***, P, M1, F |
| 1142 | a, M1, M1, P, 1, F |
| 1143 | BHF, ML***, L***, p, L***, F |
| 1144 | BHF, ML***, LA08, p, ML***, F |
| 1145 | A, ML***, BHF, p, LA08, F |
| 1146 | MA, L***, 1, p, LA08, F |
| 1147 | BHF, LA08, BHF, p, L***, F |
| 1148 | a, 1, M1, P, M1, F |
| 1149 | A, 1, 1, p, L***, F |
| 1150 | BHF, M1, LA08, p, M1, F |
| 1151 | a, ML***, BHF, P, L***, F |
| 1152 | Ma, L***, BHF, p, 1, F |
| 1153 | Ma, M1, 1, p, M1, F |
| 1154 | BHF, ML***, L***, p, LA08, F |
| 1155 | a, 1, BHF, P, L***, F |
| 1156 | BHF, M1, M1, P, LA08, F |
| 1157 | Ma, ML***, L***, P, L***, F |
| 1158 | LA02, LA08, BHF, P, ML***, F |
| 1159 | MA, ML***, L***, p, L***, F |
| 1160 | BHF, L***, BHF, p, L***, F |
| 1161 | Ma, L***, BHF, p, L***, F |
| 1162 | A, M1, LA08, P, 1, F |
| 1163 | Ma, ML***, BHF, P, LA08, F |
| 1164 | a, 1, M1, p, LA08, F |
| 1165 | A, L***, L***, P, LA08, F |
| 1166 | Ma, ML***, L***, p, L***, F |
| 1167 | BHF, 1, ML***, p, LA08, F |
| 1168 | MA, L***, BHF, p, L***, F |
| 1169 | A, ML***, L***, p, ML***, F |
| 1170 | A, L***, M1, p, 1, F |
| 1171 | MA, ML***, 1, p, L***, F |
| 1172 | a, 1, M1, p, M1, F |
| 1173 | BHF, M1, BHF, p, 1, F |
| 1174 | LA02, L***, BHF, p, L***, F |
| 1175 | a, 1, M1, P, ML***, F |
| 1176 | MA, M1, M1, P, 1, F |
| 1177 | BHF, M1, ML***, p, LA08, F |
| 1178 | BHF, ML***, LA08, p, L***, F |
| 1179 | BHF, ML***, LA08, p, L***, F |
| 1180 | A, 1, M1, p, L***, F |
| 1181 | A, 1, ML***, P, L***, F |
| 1182 | A, M1, M1, P, 1, F |
| 1183 | LA02, 1, LA08, p, 1, F |
| 1184 | Ma, ML***, 1, p, ML***, F |
| 1185 | a, 1, M1, p, L***, F |
| 1186 | LA02, M1, LA08, P, LA08, F |
| 1187 | A, LA08, L***, p, L***, F |
| 1188 | Ma, L***, LA08, p, ML***, F |
| 1189 | Ma, L***, BHF, p, LA08, F |

TABLE 1-continued

| Compound No. | Cyclic Peptide Sequence |
|---|---|
| 1190 | MA, M1, 1, P, L***, F |
| 1191 | A, L***, 1, p, 1, F |
| 1192 | a, L***, ML***, P, 1, F |
| 1193 | BHF, ML***, BHF, p, LA08, F |
| 1194 | BHF, L***, LA08, p, 1, F |
| 1195 | Ma, 1, LA08, P, L***, F |
| 1196 | A, L***, ML***, p, 1, F |
| 1197 | MA, L***, LA08, p, L***, F |
| 1198 | a, ML***, BHF, p, M1, F |
| 1199 | a, M1, LA08, P, M1, F |
| 1200 | BHF, L***, M1, P, LA08, F |
| 1201 | MA, 1, LA08, p, 1, F |
| 1202 | LA02, ML***, BHF, P, L***, F |
| 1203 | BHF, M1, LA08, p, 1, F |
| 1204 | A, M1, LA08, p, LA08, F |
| 1205 | BHF, M1, L***, p, ML***, F |
| 1206 | Ma, 1, LA08, p, L***, F |
| 1207 | BHF, M1, LA08, p, ML***, F |
| 1208 | MA, L***, LA08, P, LA08, F |
| 1209 | a, M1, BHF, p, LA08, F |
| 1210 | MA, L***, BHF, P, 1, F |
| 1211 | MA, LA08, BHF, P, L***, F |
| 1212 | a, ML***, LA08, p, LA08, F |
| 1213 | MA, LA08, BHF, p, L***, F |
| 1214 | A, 1, L***, p, L***, F |
| 1215 | a, LA08, ML***, p, ML***, F |
| 1216 | Ma, M1, LA08, P, 1, F |
| 1217 | a, 1, ML***, p, L***, F |
| 1218 | BHF, M1, M1, P, ML***, F |
| 1219 | Ma, ML***, LA08, P, 1, F |
| 1220 | Ma, 1, BHF, p, ML***, F |
| 1221 | BHF, M1, M1, p, LA08, F |
| 1222 | Ma, M1, BHF, p, 1, F |
| 1223 | MA, M1, BHF, p, 1, F |
| 1224 | LA02, LA08, M1, P, M1, F |
| 1225 | MA, ML***, LA08, P, LF |
| 1226 | MA, LA08, ML***, P, 1, F |
| 1227 | Ma, LA08, L***, p, M1, F |
| 1228 | a, LA08, M1, p, L***, F |
| 1229 | a, LA08, 1, P, ML***, F |
| 1230 | A, LA08, M1, p, ML***, F |
| 1231 | a, LA08, L***, p, 1, F |
| 1232 | MA, LA08, L***, p, 1, F |
| 1233 | a, LA08, LA08, p, L***, F |
| 1234 | LA02, LA08, L***, p, LA08, F |
| 1235 | MA, LA08, LA08, P, L***, F |
| 1236 | a, LA08, LA08, p, L***, F |
| 1237 | a, LA08, LA08, p, L***, F |
| 1238 | A, 1, M1, p, M1, F |
| 1239 | BHF, 1, M1, p, 1, F |
| 1240 | Ma, M1, M1, P, ML***, F |

Pharmaceutical Compositions and Methods of Use

The pharmaceutical composition according to the embodiments can further comprise a pharmaceutically acceptable carrier. The composition is conveniently formulated in a form suitable for oral (including buccal and sublingual) administration, for example as a tablet, capsule, thin film, powder, suspension, solution, syrup, dispersion or emulsion. The composition can contain components conventional in pharmaceutical preparations, e.g. one or more carriers, binders, lubricants, excipients, pH modifiers, sweeteners, bulking agents, coloring agents or further active agents.

As described above, patients can be humans, and also other mammals, such as livestock, zoo animals and companion animals, such as a cat, dog or horse.

In some embodiments, the present disclosure provides cyclic peptide scaffolds for use in the treatment of a patient.

In another aspect, the embodiments provide a method of treating a patient requiring treatment, which comprises administering an effective amount of one or more of the cyclic peptide scaffolds or pharmaceutical composition as described hereinabove. The amount of the one or more of the cyclic peptide scaffolds or pharmaceutical composition disclosed herein to be administered to a patient to be effective will depend upon the bioavailability of the particular composition, as well as other factors, such as the species, age, weight, sex, and condition of the patient, manner of administration and judgment of the prescribing physician. In general, the composition dose can be such that the cyclic peptide is in the range of from 0.01 milligrams per kilogram to 20 milligrams per kilogram (mg/kg) body weight. For example, a composition comprising a cyclic peptide scaffold compound can be administered at a dose equivalent to administration in the range of from 0.02 to 0.5 mg/kg body weight or 0.01 mg/kg to 10 mg/kg body weight or 0.01 to 2 mg/kg body weight.

The present disclosure also provides dose units of the subject cyclic peptide scaffold compounds that can provide for a desired pharmacokinetic (PK) profile. Dose units can provide a modified PK profile compared to a reference PK profile as disclosed herein. It will be appreciated that a modified PK profile can provide for a modified pharmacodynamic (PD) profile. Ingestion of multiples of such a dose unit can also provide a desired PK profile. The term dose unit is used herein to refer to a composition that provdies a therapeutically effective amount of drug (i.e., a sufficient amount of drug to effect a therapeutic effect, e.g., a dose within the respective drug's therapeutic window, or therapeutic range). "Multiple dose units" or "multiples of a dose unit" or a "multiple of a dose unit" refers to at least two single dose units.

As used herein, a "PK profile" refers to a profile of drug concentration in blood or plasma. Such a profile can be a relationship of drug concentration over time (i.e., a "concentration-time PK profile") or a relationship of drug concentration versus number of doses ingested (i.e., a "concentration-dose PK profile".) A PK profile is characterized by PK parameters.

As used herein, a "PK parameter" refers to a measure of drug concentration in blood or plasma, such as: 1) "drug Cmax", the maximum concentration of drug achieved in blood or plasma; 2) "drug Tmax", the time elapsed following ingestion to achieve Cmax; and 3) "drug exposure", the total concentration of drug present in blood or plasma over a selected period of time, which can be measured using the area under the curve (AUC) of a time course of drug release over a selected period of time (t). Modification of one or more PK parameters provides for a modified PK profile.

For purposes of describing the features of dose units of the present disclosure, "PK parameter values" that define a PK profile include drug Cmax (e.g., phenolic opioid Cmax), total drug exposure (e.g., area under the curve) and 1/(drug Tmax) (such that a decreased 1/Tmax is indicative of a delay in Tmax relative to a reference Tmax). Thus a decrease in a PK parameter value relative to a reference PK parameter value can indicate, for example, a decrease in drug Cmax, a decrease in drug exposure, and/or a delayed Tmax.

Dose units of the present disclosure can be adapted to provide for a modified PK profile, e.g., a PK profile that is different from that achieved from dosing a given dose of the cyclic peptide scaffold compound. For example, dose units can provide for at least one of decreased drug Cmax, delayed drug Tmax and/or decreased drug exposure.

As used herein, "a pharmacodynamic (PD) profile" refers to a profile of the efficacy of a drug in a patient (or subject or user), which is characterized by PD parameters. "PD parameters" include "drug Emax" (the maximum drug efficacy), "drug EC50" (the concentration of drug at 50% of the Emax), and side effects.

A dose unit can be adapted to provide for a desired PK profile (e.g., a concentration-time PK profile) following ingestion of a single dose. A dose unit can be adapted to provide for a desired PK profile (e.g., a concentration-dose PK profile) following ingestion of multiple dose units (e.g., at least 2, at least 3, at least 4 or more dose units).

In compositions of the present disclosure, the compounds disclosed herein may be administered in the form of their pharmaceutically acceptable salts, or they may also be used alone or in appropriate association, as well as in combination, with other pharmaceutically active compounds. The following methods and excipients are merely exemplary and are in no way limiting.

The cyclic peptide scaffold compounds can be administered to a host using any available conventional methods and routes suitable for delivery of conventional drugs, including systemic or localized routes. In general, routes of administration contemplated include but are not necessarily limited to, enteral, parenteral, or inhalational routes, such as intrapulmonary or intranasal delivery.

Conventional and pharmaceutically acceptable routes of administration include intranasal, intrapulmonary, intramuscular, intratracheal, subcutaneous, intradermal, topical application, intravenous, rectal, nasal, oral and other parenteral routes of administration. Routes of administration may be combined, if desired, or adjusted depending upon the agent and/or the desired effect. The composition can be administered in a single dose or in multiple doses.

For oral preparations, the subject compounds can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents. If oral administration is desired, the subject compounds may optionally be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

Parenteral routes of administration other than inhalation administration include, but are not necessarily limited to, topical, transdermal, subcutaneous, intramuscular, intraorbital, intracapsular, intraspinal, intrasternal, and intravenous routes. Parenteral administration can be carried to effect systemic or local delivery of the agent. Where systemic delivery is desired, administration typically involves invasive or systemically absorbed topical or mucosal administration of pharmaceutical preparations. Where local delivery is desired, administration typically involves administering the composition to a desired target tissue, such a liver, heart, spine, etc. For local delivery, the administration may be by injection or by placement of the composition in the desired tissue or organ by surgery, for example.

Methods of administration of the agent through the skin or mucosa include, but are not necessarily limited to, topical application of a suitable pharmaceutical preparation, transdermal transmission, injection and epidermal administration. For transdermal transmission, absorption promoters or iontophoresis are suitable methods. Iontophoretic transmission may be accomplished using commercially available "patches" which deliver their product continuously via electric pulses through unbroken skin for periods of several days or more.

The subject compounds of the invention can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The subject compounds can also be delivered to the subject by enteral administration. Enteral routes of administration include, but are not necessarily limited to, oral and rectal (e.g., using a suppository) delivery.

Furthermore, the subject compounds can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

Aspects of the present disclosure also include a library having 5 or more of the cell permeable cyclic peptide scaffolds described hereinabove, such as 10 or more, such as 15 or more, such as 20 or more, such as 25 or more, such as 30 or more, such as 35 or more, such as 40 or more, such as 45 or more, such as 50 or more, such as 75 or more and including a library having 100 or more of the subject cell permeable cyclic peptide scaffolds. The library of compounds may be include cyclic peptide scaffolds having similar amino acid sequences, conformation structures, or cell permeability values as desired. In embodiments, libraries of interest include 5 or more cell permeable cyclic peptide scaffolds, eaching having a structure according to Formula I:

Cyclo [Z—Y—X-Pro-Y-Phe]  Formula I wherein:
Pro is L-proline or D-proline;
Phe is L-phenylalanine or D-phenylalanine;
X is

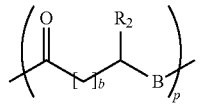

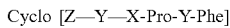

Y is

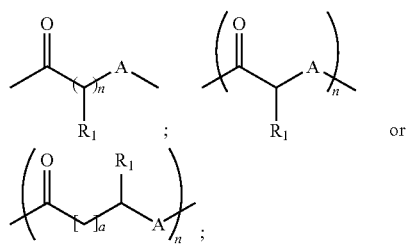

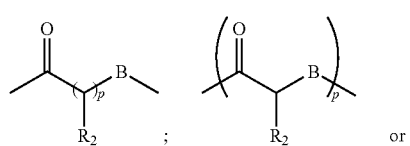

Z is

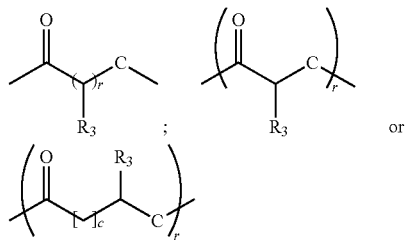

each $R_1$ is independently selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl, or optionally, $R^1$ together with the atoms to which it is bonded form a cycloheteroalkyl or substituted cycloheteroalkyl ring;

each $R_2$ is independently selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl, or optionally, $R^1$ together with the atoms to which it is bonded form a cycloheteroalkyl or substituted cycloheteroalkyl ring;

each $R_3$ is independently selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl, or optionally, $R^1$ together with the atoms to which it is bonded form a cycloheteroalkyl or substituted cycloheteroalkyl ring;

A is selected from —$NR_a$—, —O— or —S—;
B is selected from —$NR_b$—, —O— or —S—;
C is selected from —$NR_c$—, —O— or —S—;
each $R_a$, $R_b$, $R_c$ is independently selected from hydrogen, alkyl, substituted alkyl, aryl and substituted aryl, or
  $R_1$ and $R_a$ together with the atoms to which they are bonded form a cycloheteroalkyl or substituted cycloheteroalkyl ring;
  $R_2$ and $R_b$ together with the atoms to which they are bonded form a cycloheteroalkyl or substituted cycloheteroalkyl ring;
  $R_3$ and $R_c$ together with the atoms to which they are bonded form a cycloheteroalkyl or substituted cycloheteroalkyl ring;
n is an integer from one to 5 and a is an integer from one to 5;
p is an integer from one to 5 and b is an integer from one to 5; and
r is an integer from one to 5 and c is an integer from one to 5;
or a pharmaceutical acceptable salt, solvate or hydrate thereof.

EXAMPLES

As can be appreciated from the disclosure provided above, the present disclosure has a wide variety of applications. Accordingly, the following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Those of skill in the art will readily recognize a variety of noncritical parameters that could be changed or modified to yield essentially similar results. Thus, the following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, dimensions, etc.) but some experimental errors and deviations should be accounted for.

General

All starting reagents were commercially available and used without further purification except where mentioned. Purification was performed on a Biotage Isolera Prime HPLC using various solvent systems and columns (listed individually). Composition and purity were tested by HPLC (Waters 1525) with an attached mass spectrometer (Micromass ZQ, waters) and PDA detector (Waters 2998) through a 3.5 μm C18 column (XBridge BEH C18 4.6×50 mm). A mixture of water (0.1% formic acid) and ACN (0.1% formic acid) was used as an eluent, with results being analyzed by MassLynx4.1. Runs were 12 minutes long with 1.2 ml/min flow rate; ACN concentration was increased stepwise from its starting concentration (30% 0-2 min, linear increase to 100% 2-10 min, 100% 10-12 min). Tandem MS runs and LC-MS analyses for PAMPA were performed on an UHPLC (UltiMate 3000, Dionex) with attached mass spectrometer (Orbitrap Velos Pro, Thermo Scientific) through a 2.2 μm C18 column (Acclaim 120 2.1×250 mm, Thermo Scientific). A mixture of water (0.1% formic acid) and ACN (0.1% formic acid) was used as an eluent, with results being analyzed by XCALIBUR version 2.2 SP1.48. Runs were 32.7 minutes long with 0.5 ml/min flow rate; ACN concentration was increased stepwise from its starting concentration (40% 0-2 min, linear increase to 85% 2-22 min, 100% 22-27 min, 40% 27-32.7 min).

Fmoc Addition to Isotopically Labeled Leucine

Fmoc was added to unprotected isotopically labeled leucine. The procedure used herein was adapted from Malkov A et al, Journal of Organic Chemistry 74, 5839-5849, 2009 (including supporting information) which incorporated by reference herein. One gram of isotopically labeled leucine was added to a separate flask containing 30 ml of distilled water 80% saturated with sodium bicarbonate, then agitated by sonication until dissolved. 2.82 g (1 molar equivalent) of Fmoc succinimide was added to a separate round-bottom flask in an ice bath containing 30 ml dioxane. The dissolved leucine was added dropwise to the Fmoc solution over 10 minutes with rapid stirring. The mixture was stirred 2 hours on ice, then allowed to come to room temperature overnight with continued stirring. The mixture was then evaporated at 25 degrees Celsius and brought up in a minimal volume of DMF before reverse-phase purification over a SNAP Ultra C18 30 g cartridge (Biotage), eluting with water (0.1% TFA)/ACN (0.1% TFA). The resulting fractions were analyzed on the Waters LC-MS system, pooled, and evaporated to a white solid.

N-Methylation of Fmoc Amino Acids

All N-methylated amino acids used in the library synthesis were synthesized via the following procedure: Fmoc amino acid and paraformaldehyde (1:1 by mass) were added to a round-bottom flask containing 75 ml toluene per 5 g of amino acid. The flask was heated to 90 degrees Celsius before 0.2 molar equivalents of camphorsulfonic acid was added. The flask was stirred for at least 2 hours, then the solution was evaporated to 3 ml volume per gram of amino acid. 5 ml of ethyl acetate per gram of amino acid was added. The solution was then transferred to a separatory funnel and washed twice with an equal volume of water saturated with sodium bicarbonate and once with an equal volume of brine. The organic layer was dried with magnesium sulfate, filtered into a round-bottom flask, then evaporated to a minimal volume. 2 ml of DCM per gram of amino acid was added to the flask and the oil or solid thoroughly dissolved. Once dissolved, an equal volume of trifluoroacetic acid was added, then stirred for 5 minutes. Finally, 3 molar equivalents of triethylsilane was added and let stir overnight. The solution was then evaporated to minimal volume before addition of 5 ml ethyl acetate per gram of amino acid, transferred to a separatory funnel and washed twice with an equal volume of distilled water and once with an equal volume of brine. The organic layer was dried, filtered into a round-bottom flask, and evaporated to a white solid, then analyzed for purity.

Cyclic Peptomer Synthesis

Linear peptomers were synthesized on 2-chlorotrityl resin (0.14 mmol/g) using extended Fmoc coupling (Fmoc amino acid/HATU/DIPEA in DMF, overnight) and peptoid synthesis conditions (bromoacetic acid/DIC in DMF, 1 hr, then amine in DMF, overnight). The linear peptomers were cleaved from resin with 30% HFIP in DCM. Cyclization was performed in dilute conditions (<3 mM peptomer in a solution of 1:1 ACN:THF) with COMU (2 equiv) and DIPEA (10 equiv) and stirred overnight at room temperature. Each sublibrary was briefly purified using Isolute 103 SPE cartridge (200 mg/6 mL, Biotage).

Resin Loading Procedure

Phenylalanine and 2-Chlorotrityl resin were placed in a vacuum desiccator with phosphorous pentoxide overnight. The phenylalanine was added to a flame-dried round-bottom flask. Dry DCM of sufficient volume for the resin to float freely and 4 molar equivalents of dry DIPEA was added to the flask, which was then sonicated until the phenylalanine dissolved completely. The resin was added to the flask and the flask purged of air with a flow of argon, after which the flask was agitated for 4 hrs. The resin was transferred to a solid-phase synthesis tube/manifold and washed with 2 resin-volumes of DMF (3×), then 2 resin-volumes DCM (3×), always keeping the solvent level above the resin. Finally, the resin was capped with a solution of 17:2:1 DCM:MeOH:DIPEA (2 resin-volumes, 3×, 15 min incubation each). Loading value was calculated via resin cleavage (1% TFA) followed by quantification by UV absorbance at 280 nm.

Fmoc Deprotection

Two resin-volumes of 2% DBU 2% piperidine in DMF was added to the resin and the tube was capped and agitated for 20 minutes. The resin was then drained and washed with 2 resin-volumes of DMF (×3) and 2 resin-volumes of DCM (×3).

Amino Acid Couplings

Due to low resin loading value, 12 molar equivalents of Fmoc amino acid, 11.4 molar equivalents of HATU, and 15 molar equivalents of DIPEA were used to maintain high concentration in a DMF volume large enough to cover the resin. Fmoc amino acid, HATU, and dipea were added to a vial, then solubilized in the minimal amount of DMF which covers the resin-volume. The vial was set aside to react for 15 minutes before its contents were added to the resin. The SPPS tube was then capped and agitated overnight. The resin was then drained and washed with 2 resin-volumes of DMF (×3) and 2 resin-volumes of DCM (×3).

Peptoid Synthesis

For the same reasons as above, the 30 molar equivalents of bromoacetic acid was added to a vial and solubilized in a minimal volume of DMF which still covers the resin volume. 18 molar equivalents of DIC was then added, and the vial capped, mixed, and reacted for 15 minutes. The vial's contents were then added to the resin. The SPPS tube was then capped and agitated for 1 hour, after which the resin was drained and washed as above. 30 molar equivalents of the amine of choice was then added directly to the resin and the volume was increased with a minimal amount of DMF before capping the tube and agitating overnight (although the extended reaction time likely had little bearing on the results!). Finally, the resin was drained and washed as above.

Peptide Cleavage

Two resin-volumes of 30% HFIP in DCM was added to the resin, the tube capped, then agitated for 30 minutes. The tube was then drained into a vial, and was further washed with an equal volume of DCM three times. This above was then repeated with the addition of a further wash step of an equal volume of acetone. The contents of the vial were then evaporated.

Peptide Cyclization 5 ml ACN and 10 molar equivalents of DIPEA were added to each vial containing a cleaved sublibrary. The vials were then sonicated until all peptides were totally dissolved before addition of 5 ml THF, diluting the peptides to <3 mM. 2 molar equivalents of COMU were added to each vial, all of which were stirred overnight. Finally, each vial was evaporated to a solid or oil.

Purification of Sublibraries

Purification of each sublibrary was performed on individual Isolute 103 ENV+ flash chromatography columns (200 mg/6 ml). Each sublibrary was dissolved in a minimal volume of DMF (75 ul or less) and loaded onto the dry column. The column was washed with 10 ml of water, followed by elution with 10 ml of methanol into tared vials. The methanol was then evaporated and the vials weighed for final yield.

Verification of Synthesis

The composition and purity of each sublibrary were tested by LC-MS (Waters system). Expected UV absorbance and masses for the library and possible truncations were observed to verify synthesis and purity.

MSMS and PAMPA LC-MS Data Acquisition

PAMPA LC-MS data was acquired as above with no modifications. Tandem MS data was acquired by taking the 5 most intense non-isotopic peaks (Xcalibur setting) for MS2 acquisition at every MS1 acquisition.

Parallel Artificial Membrane Permeability Assay Procedure

Parallel Artificial Membrane Permeability Assay (PAMPA) was performed with a 96-well filter donor plate with 0.45 μm hydrophobic Immobilon-P membrane supports (Millipore) and a 96-well teflon acceptor plate. The donor plate filter was loaded with 5 μL of 1% lecithin in n-dodecane. 1NMe3, a well-characterized cyclic peptide, was added as a standard in each well at a concentration of 10 uM. 150 ul of each sublibrary (including standard) in PBS (containing 5% DMSO) was loaded into the donor plate (300 uM theoretical concentration, or ~2 uM per compound). The acceptor plate was loaded with 300 ul of PBS with 5% DMSO. The donor filter plate was then loaded into the acceptor plate and was left in a damp chamber at 25° C. for 18 hours. The concentration of each compound in the donor and acceptor wells was quantified by LC-MS to calculate Pe.

PAMPA Data Analysis

For each well, single ion chromatograms for each library mass were extracted, followed by peak-finding by first differential. The peak boundaries were found by following outward from peaks until the second differential met a detection threshold at a point sufficiently below the intensity of the peak center-point. Peaks and peak boundaries which were incorrectly detected were manually corrected. Integration was performed by fitting a Gaussian distribution to each peak and calculating its area.

Peaks were matched by retention time and peak number across wells to get acceptor and donor well intensities for each peak. A time independent permeability value was then calculated via the following equations:

$$C_{eq} = \frac{C_D \times V_D + C_A \times V_A}{V_D + V_A}$$

$$\% T = \frac{C_A}{C_{eq}} \times 100$$

$$P_e = \frac{-\ln\left(1 - \frac{C_A}{C_{eq}}\right)}{\left(\frac{1}{V_D} + \frac{1}{V_A}\right) \times \text{Area} \times \text{Time}}$$

Wherein C is concentration, V is well volume, % T is percent transmittance to the acceptor well, and Pe is the desired time-independent permeability value. The subscript eq stands for equilibrium, A for acceptor and D for donor. For these calculations, concentration has been substituted for intensity under the peak since the ionization intensity of a compound should not vary overly much between two wells. Finally, the Pe values were corrected based on the known Pe of the 1NMe3 standard.

Permeability values for the compounds of Table 1 were determined as described above and are summarized in Table 2.

| Compound No. | Peptomer Sequence | Permeability Value ($\times 10^{-6}$ cm/s) |
|---|---|---|
| 1 | BHF, L***, BHF, p, L***, F | 56.19061214 |
| 2 | BHF, 1, M1, p, M1, F | 50.8282355 |
| 3 | A, L***, L***, p, LA08, F | 48.71672758 |
| 4 | BHF, 1, M1, p, 1, F | 46.22198458 |
| 5 | BHF, L***, 1, P, L***, F | 42.78148279 |
| 6 | Ma, M1, L***, P, 1, F | 41.14185131 |
| 7 | A, L***, 1, p, 1, F | 36.44199332 |
| 8 | A, M1, BHF, P, 1, F | 34.07095274 |
| 9 | A, M1, 1, p, ML***, F | 33.27688014 |
| 10 | a, M1, 1, P, M1, F | 32.88796918 |
| 11 | MA, M1, M1, P, M1, F | 32.57897584 |
| 12 | A, 1, BHF, p, 1, F | 30.68291478 |
| 13 | BHF, 1, M1, P, M1, F | 29.1942956 |
| 14 | MA, M1, M1, P, ML***, F | 28.52497238 |
| 15 | MA, LA08, M1, P, 1, F | 28.50650176 |
| 16 | MA, M1, L***, P, M1, F | 28.33829512 |
| 17 | BHF, 1, ML***, P, ML***, F | 27.98815431 |
| 18 | BHF, L***, BHF, p, 1, F | 27.68606544 |

-continued

| Compound No. | Peptomer Sequence | Permeability Value (×10⁻⁶ cm/s) |
|---|---|---|
| 19 | MA, LA08, L***, P, M1, F | 27.41715714 |
| 20 | BHF, M1, M1, P, M1, F | 27.07177771 |
| 21 | LA02, 1, M1, P, M1, F | 26.82931976 |
| 22 | a, M1, ML***, p, 1, F | 26.82301824 |
| 23 | a, L***, L***, p, M1, F | 26.76564435 |
| 24 | BHF, M1, M1, p, M1, F | 26.70634473 |
| 25 | BHF, M1, M1, P, M1, F | 26.55043548 |
| 26 | Ma, L***, ML***, P, M1, F | 26.50654657 |
| 27 | MA, ML***, LA08, P, LA08, F | 26.32870586 |
| 28 | MA, M1, M1, P, M1, F | 26.22773297 |
| 29 | BHF, M1, M1, p, 1, F | 26.17265039 |
| 30 | a, ML***, L***, p, 1, F | 26.1105021 |
| 31 | Ma, M1, L***, P, ML***, F | 25.94258816 |
| 32 | A, M1, M1, p, 1, F | 25.80002884 |
| 33 | A, M1, L***, p, M1, F | 25.78220373 |
| 34 | A, LA08, M1, p, L***, F | 25.55775971 |
| 35 | A, M1, L***, P, M1, F | 25.36713829 |
| 36 | a, M1, BHF, p, M1, F | 25.35607442 |
| 37 | Ma, ML***, 1, P, ML***, F | 25.10086123 |
| 38 | A, M1, M1, P, ML***, F | 25.09089699 |
| 39 | MA, 1, M1, P, ML***, F | 25.0861927 |
| 40 | A, M1, M1, p, LA08, F | 25.03162272 |
| 41 | MA, M1, ML***, P, M1, F | 25.01886329 |
| 42 | BHF, M1, M1, P, M1, F | 24.87040135 |
| 43 | Ma, M1, 1, P, M1, F | 24.82810692 |
| 44 | Ma, M1, 1, P, M1, F | 24.82810692 |
| 45 | LA02, M1, LA08, P, M1, F | 24.5926188 |
| 46 | LA02, M1, LA08, P, M1, F | 24.5926188 |
| 47 | A, L***, BHF, p, 1, F | 24.57015331 |
| 48 | MA, M1, M1, P, L***, F | 24.38438951 |
| 49 | Ma, M1, M1, P, M1, F | 24.38348673 |
| 50 | Ma, ML***, M1, P, M1, F | 24.31080278 |
| 51 | MA, 1, M1, P, 1, F | 24.17124034 |
| 52 | A, M1, ML***, P, M1, F | 24.16377896 |
| 53 | A, L***, M1, p, ML***, F | 24.16030909 |
| 54 | MA, L***, M1, P, M1, F | 23.92605054 |
| 55 | A, 1, LA08, p, 1, F | 23.91283292 |
| 56 | Ma, M1, ML***, P, M1, F | 23.73833678 |
| 57 | MA, M1, LA08, P, ML***, F | 23.72007441 |
| 58 | A, M1, BHF, P, M1, F | 23.59143159 |
| 59 | BHF, 1, 1, p, M1, F | 23.53463022 |
| 60 | a, L***, BHF, p, 1, F | 23.26495371 |
| 61 | a, L***, LA08, P, L***, F | 23.22930206 |
| 62 | BHF, L***, 1, p, M1, F | 23.10492023 |
| 63 | a, M1, L***, p, M1, F | 23.0837236 |
| 64 | MA, ML***, M1, P, M1, F | 22.86097011 |
| 65 | Ma, 1, ML***, P, ML***, F | 22.72909836 |
| 66 | BHF, M1, M1, p, M1, F | 22.65698306 |
| 67 | MA, ML***, L***, p, M1, F | 22.65481294 |
| 68 | a, ML***, M1, P, 1, F | 22.58524245 |
| 69 | A, M1, M1, p, M1, F | 22.48095643 |
| 70 | A, ML***, BHF, P, L***, F | 22.47943243 |
| 71 | A, L***, L***, p, 1, F | 22.35705255 |
| 72 | Ma, ML***, M1, P, L***, F | 22.21408662 |
| 73 | A, 1, ML***, p, 1, F | 22.16308149 |
| 74 | A, M1, BHF, p, M1, F | 22.04952601 |
| 75 | MA, 1, M1, P, LA08, F | 21.9422274 |
| 76 | A, M1, BHF, p, M1, F | 21.89615654 |
| 77 | LA02, M1, BHF, P, L***, F | 21.85502465 |
| 78 | A, M1, 1, p, LA08, F | 21.78328972 |
| 79 | A, M1, 1, p, M1, F | 21.65504441 |
| 80 | A, M1, L***, p, ML***, F | 21.64904102 |
| 81 | Ma, M1, L***, P, LA08, F | 21.58462332 |
| 82 | A, 1, M1, p, F | 21.47967737 |
| 83 | a, M1, L***, P, M1, F | 21.43740026 |
| 84 | MA, M1, M1, p, M1, F | 21.43183575 |
| 85 | A, L***, LA08, p, M1, F | 21.40673824 |
| 86 | MA, L***, M1, P, M1, F | 21.2633048 |
| 87 | Ma, M1, M1, P, LA08, F | 21.25660811 |
| 88 | LA02, M1, L***, P, 1, F | 21.21198624 |
| 89 | Ma, L***, M1, P, ML***, F | 21.1569649 |
| 90 | Ma, ML***, L***, P, M1, F | 20.98978613 |
| 91 | A, M1, BHF, P, M1, F | 20.9628871 |
| 92 | Ma, M1, M1, P, M1, F | 20.76313119 |
| 93 | a, M1, BHF, p, M1, F | 20.74335994 |
| 94 | BHF, M1, M1, P, M1, F | 20.73949965 |
| 95 | a, M1, L***, P, ML***, F | 20.73281225 |
| 96 | BHF, L***, LA08, P, L***, F | 20.72754175 |
| 97 | A, M1, L***, p, 1, F | 20.51626729 |
| 98 | LA02, M1, BHF, P, M1, F | 20.41552774 |
| 99 | A, M1, L***, P, ML***, F | 20.2928769 |
| 100 | MA, ML***, 1, P, M1, F | 20.24070307 |
| 101 | Ma, M1, M1, P, M1, F | 20.2032426 |
| 102 | a, M1, BHF, p, M1, F | 20.10606447 |
| 103 | LA02, M1, M1, P, M1, F | 20.05269969 |
| 104 | MA, M1, ML***, P, LA08, F | 19.92606853 |
| 105 | LA02, L***, 1, P, L***, F | 19.78870101 |
| 106 | MA, 1, L***, p, ML***, F | 19.73554909 |
| 107 | Ma, L***, M1, p, ML***, F | 19.73186827 |
| 108 | MA, M1, 1, P, ML***, F | 19.69291384 |
| 109 | MA, L***, M1, P, ML***, F | 19.6567569 |
| 110 | BHF, L***, M1, P, L***, F | 19.61804884 |
| 111 | Ma, ML***, M1, P, LA08, F | 19.53234979 |
| 112 | a, LA08, M1, p, L***, F | 19.52903752 |
| 113 | LA02, 1, M1, P, M1, F | 19.51724784 |
| 114 | A, L***, LA08, p, 1, F | 19.5156128 |
| 115 | a, ML***, M1, P, LA08, F | 19.49874601 |
| 116 | a, 1, LA08, p, 1, F | 19.49562529 |
| 117 | a, M1, LA08, p, 1, F | 19.47372828 |
| 118 | A, 1, L***, P, L***, F | 19.46627882 |
| 119 | LA02, M1, M1, p, M1, F | 19.45529183 |
| 120 | A, 1, L***, p, L***, F | 19.36475021 |
| 121 | LA02, 1, M1, P, 1, F | 19.28813728 |
| 122 | a, M1, BHF, P, M1, F | 19.25184441 |
| 123 | A, L***, LA08, p, LA08, F | 19.22735011 |
| 124 | A, 1, L***, p, M1, F | 19.15078912 |
| 125 | a, M1, L***, p, 1, F | 19.11174655 |
| 126 | Ma, M1, BHF, P, M1, F | 19.08802734 |
| 127 | Ma, M1, 1, P, LA08, F | 19.04687727 |
| 128 | MA, 1, ML***, P, ML***, F | 18.99987845 |
| 129 | BHF, M1, M1, p, M1, F | 18.94392122 |
| 130 | Ma, M1, 1, P, 1, F | 18.93627832 |
| 131 | Ma, LA08, M1, P, M1, F | 18.91178744 |
| 132 | Ma, L***, M1, P, L***, F | 18.89699421 |
| 133 | a, M1, 1, P, ML***, F | 18.86867707 |
| 134 | BHF, 1, M1, P, 1, F | 18.8550913 |
| 135 | BHF, 1, L***, p, ML***, F | 18.84710992 |
| 136 | a, M1, LA08, p, ML***, F | 18.80246438 |
| 137 | MA, 1, M1, P, M1, F | 18.79110041 |
| 138 | MA, M1, 1, P, M1, F | 18.79110041 |
| 139 | BHF, M1, M1, P, M1, F | 18.77564569 |
| 140 | A, L***, M1, P, L***, F | 18.76412648 |
| 141 | a, M1, L***, p, ML***, F | 18.75454855 |
| 142 | MA, L***, M1, P, 1, F | 18.72629726 |
| 143 | LA02, M1, 1, P, M1, F | 18.57443693 |
| 144 | Ma, LA08, 1, P, M1, F | 18.56149677 |
| 145 | MA, M1, BHF, P, M1, F | 18.49316068 |
| 146 | BHF, 1, 1, P, ML***, F | 18.45259647 |
| 147 | Ma, L***, 1, P, ML***, F | 18.32419316 |
| 148 | Ma, L***, 1, P, M1, F | 18.30172016 |
| 149 | MA, 1, LA08, P, ML***, F | 18.26363562 |
| 150 | BHF, M1, M1, p, M1, F | 18.22781209 |
| 151 | MA, M1, 1, P, M1, F | 18.20517238 |
| 152 | MA, M1, M1, P, 1, F | 18.20517238 |
| 153 | LA02, L***, L***, P, M1, F | 18.18720053 |
| 154 | a, LA08, M1, P, M1, F | 18.15357743 |
| 155 | MA, M1, M1, P, 1, F | 17.98832753 |
| 156 | MA, M1, M1, P, 1, F | 17.98832753 |
| 157 | Ma, 1, M1, P, M1, F | 17.98816681 |
| 158 | LA02, 1, L***, p, M1, F | 17.98540374 |
| 159 | Ma, LA08, M1, P, M1, F | 17.9484773 |
| 160 | LA02, 1, L***, P, ML***, F | 17.8677765 |
| 161 | A, 1, ML***, p, M1, F | 17.83963166 |
| 162 | Ma, M1, BHF, P, M1, F | 17.82220647 |
| 163 | a, LA08, ML***, P, M1, F | 17.80862671 |
| 164 | LA02, L***, 1, P, M1, F | 17.79963046 |
| 165 | Ma, M1, BHF, P, M1, F | 17.7337768 |
| 166 | A, M1, M1, p, M1, F | 17.72766039 |
| 167 | a, ML***, L***, p, ML***, F | 17.70135387 |
| 168 | LA02, M1, M1, P, M1, F | 17.67238466 |

-continued

| Compound No. | Peptomer Sequence | Permeability Value (×10⁻⁶ cm/s) |
|---|---|---|
| 169 | A, M1, ML***, p, L***, F | 17.66551964 |
| 170 | MA, 1, 1, P, LA08, F | 17.65724109 |
| 171 | a, M1, L***, P, LA08, F | 17.62447466 |
| 172 | A, L***, ML***, p, M1, F | 17.6142183 |
| 173 | BHF, 1, M1, p, L***, F | 17.57956415 |
| 174 | a, LA08, M1, p, ML***, F | 17.5486073 |
| 175 | MA, ML***, LA08, P, LA08, F | 17.54234433 |
| 176 | BHF, ML***, LA08, p, ML***, F | 17.51418039 |
| 177 | BHF, L***, M1, p, 1, F | 17.49544027 |
| 178 | LA02, 1, ML***, P, M1, F | 17.46829141 |
| 179 | Ma, ML***, L***, p, M1, F | 17.40797742 |
| 180 | MA, 1, ML***, P, LA08, F | 17.3559126 |
| 181 | A, ML***, M1, P, M1, F | 17.31337854 |
| 182 | Ma, 1, ML***, P, 1, F | 17.30863947 |
| 183 | BHF, L***, 1, p, LA08, F | 17.30227074 |
| 184 | LA02, L***, 1, p, ML***, F | 17.28279029 |
| 185 | LA02, ML***, 1, p, ML***, F | 17.10834035 |
| 186 | Ma, 1, ML***, p, ML***, F | 17.09109135 |
| 187 | MA, M1, ML***, p, ML***, F | 17.04239744 |
| 188 | LA02, M1, BHF, P, M1, F | 17.00852323 |
| 189 | LA02, ML***, 1, p, LA08, F | 16.98977471 |
| 190 | MA, 1, LA08, p, ML***, F | 16.93095047 |
| 191 | Ma, L***, M1, P, LA08, F | 16.9245817 |
| 192 | Ma, M1, M1, P, 1, F | 16.8735617 |
| 193 | A, L***, BHF, P, ML***, F | 16.86530105 |
| 194 | a, M1, 1, p, ML***, F | 16.85433362 |
| 195 | A, M1, M1, P, L***, F | 16.84945047 |
| 196 | a, M1, M1, P, 1, F | 16.83154675 |
| 197 | A, M1, ML***, p, 1, F | 16.79150455 |
| 198 | Ma, L***, M1, P, 1, F | 16.7716384 |
| 199 | A, L***, L***, p, M1, F | 16.7279933 |
| 200 | A, 1, L***, P, LA08, F | 16.71717023 |
| 201 | A, ML***, M1, P, ML***, F | 16.71659758 |
| 202 | LA02, M1, M1, P, 1, F | 16.71497558 |
| 203 | BHF, M1, M1, p, M1, F | 16.61938228 |
| 204 | LA02, M1, M1, p, M1, F | 16.61477747 |
| 205 | LA02, M1, M1, P, M1, F | 16.53444871 |
| 206 | LA02, 1, L***, P, 1, F | 16.51415444 |
| 207 | a, M1, M1, p, M1, F | 16.50115041 |
| 208 | a, LA08, ML***, P, ML***, F | 16.47863675 |
| 209 | MA, 1, ML***, p, 1, F | 16.47315765 |
| 210 | a, L***, LA08, p, 1, F | 16.47314921 |
| 211 | Ma, ML***, M1, p, M1, F | 16.41152869 |
| 212 | A, M1, M1, p, M1, F | 16.40602598 |
| 213 | A, LA08, L***, P, M1, F | 16.38356976 |
| 214 | LA02, 1, L***, p, ML***, F | 16.37435754 |
| 215 | Ma, ML***, L***, P, 1, F | 16.35782285 |
| 216 | BHF, L***, M1, p, L***, F | 16.30049653 |
| 217 | LA02, L***, M1, P, M1, F | 16.25446901 |
| 218 | LA02, 1, 1, P, L***, F | 16.24185622 |
| 219 | a, M1, BHF, P, M1, F | 16.22333019 |
| 220 | BHF, 1, ML***, P, 1, F | 16.2199749 |
| 221 | BHF, L***, 1, p, 1, F | 16.21290967 |
| 222 | A, 1, M1, P, LA08, F | 16.13438796 |
| 223 | A, M1, 1, p, LA08, F | 16.13150772 |
| 224 | BHF, 1, M1, P, M1, F | 16.11552468 |
| 225 | MA, L***, M1, P, LA08, F | 16.11353439 |
| 226 | LA02, M1, 1, p, ML***, F | 16.06160444 |
| 227 | a, ML***, L***, P, M1, F | 16.03460499 |
| 228 | A, M1, BHF, P, M1, F | 15.99903862 |
| 229 | Ma, LA08, 1, P, 1, F | 15.97290745 |
| 230 | LA02, ML***, ML***, p, M1, F | 15.96856352 |
| 231 | a, 1, 1, P, L***, F | 15.95794462 |
| 232 | A, ML***, 1, P, LA08, F | 15.93909991 |
| 233 | LA02, M1, ML***, P, M1, F | 15.9017328 |
| 234 | Ma, M1, BHF, P, M1, F | 15.86578743 |
| 235 | BHF, 1, L***, P, ML***, F | 15.79262297 |
| 236 | A, 1, ML***, P, ML***, F | 15.71564676 |
| 237 | LA02, M1, M1, p, M1, F | 15.70403365 |
| 238 | Ma, M1, M1, p, M1, F | 15.69511476 |
| 239 | BHF, L***, 1, P, 1, F | 15.69315428 |
| 240 | a, M1, M1, P, M1, F | 15.63313769 |
| 241 | A, 1, LA08, p, LA08, F | 15.58997604 |
| 242 | A, L***, 1, p, LA08, F | 15.56273971 |
| 243 | A, 1, ML***, P, M1, F | 15.54088864 |
| 244 | A, ML***, LA08, P, M1, F | 15.53169555 |
| 245 | BHF, M1, 1, p, 1, F | 15.5025513 |
| 246 | BHF, 1, L***, P, L***, F | 15.5017172 |
| 247 | LA02, M1, L***, P, M1, F | 15.49541105 |
| 248 | BHF, L***, 1, P, ML***, F | 15.4724259 |
| 249 | LA02, ML***, L***, P, 1, F | 15.43740559 |
| 250 | A, 1, ML***, P, LA08, F | 15.41168385 |
| 251 | A, M1, ML***, P, LA08, F | 15.38459523 |
| 252 | Ma, LA08, 1, P, M1, F | 15.38085543 |
| 253 | Ma, L***, LA08, P, ML***, F | 15.37105241 |
| 254 | LA02, M1, ML***, P, ML***, F | 15.21410223 |
| 255 | MA, 1, L***, p, M1, F | 15.19253259 |
| 256 | a, L***, M1, p, ML***, F | 15.15432076 |
| 257 | A, M1, LA08, p, ML***, F | 15.06505249 |
| 258 | MA, 1, M1, p, 1, F | 15.04796558 |
| 259 | LA02, L***, 1, p, M1, F | 15.03779291 |
| 260 | Ma, 1, L***, P, M1, F | 15.03506168 |
| 261 | BHF, 1, ML***, p, 1, F | 15.02224354 |
| 262 | MA, L***, 1, P, ML***, F | 15.00436914 |
| 263 | A, M1, 1, P, M1, F | 14.98102179 |
| 264 | A, L***, M1, P, LA08, F | 14.89646656 |
| 265 | a, M1, 1, P, LA08, F | 14.89615672 |
| 266 | LA02, M1, M1, P, M1, F | 14.88908064 |
| 267 | Ma, L***, LA08, P, M1, F | 14.78884386 |
| 268 | LA02, M1, LA08, P, LA08, F | 14.71448863 |
| 269 | A, 1, ML***, p, ML***, F | 14.68900781 |
| 270 | a, 1, L***, p, M1, F | 14.61652756 |
| 271 | LA02, M1, BHF, p, M1, F | 14.60273571 |
| 272 | BHF, M1, M1, P, M1, F | 14.59898542 |
| 273 | MA, M1, M1, P, M1, F | 14.59463904 |
| 274 | A, ML***, LA08, p, LA08, F | 14.58763062 |
| 275 | MA, 1, M1, P, L***, F | 14.57290574 |
| 276 | LA02, 1, BHF, P, L***, F | 14.54063724 |
| 277 | MA, M1, M1, P, M1, F | 14.53241073 |
| 278 | BHF, 1, 1, p, M1, F | 14.53035014 |
| 279 | BHF, 1, 1, p, 1, F | 14.53035014 |
| 280 | Ma, 1, BHF, P, 1, F | 14.51066215 |
| 281 | A, ML***, 1, p, LA08, F | 14.49020071 |
| 282 | MA, 1, ML***, p, ML***, F | 14.47722646 |
| 283 | a, ML***, LA08, P, ML***, F | 14.47295475 |
| 284 | BHF, L***, L***, p, M1, F | 14.46686498 |
| 285 | A, M1, M1, P, M1, F | 14.41367424 |
| 286 | A, M1, M1, P, M1, F | 14.41367424 |
| 287 | A, LA08, BHF, p, 1, F | 14.37489535 |
| 288 | a, LA08, M1, P, L***, F | 14.3588776 |
| 289 | a, 1, ML***, p, M1, F | 14.34321989 |
| 290 | BHF, 1, 1, p, LA08, F | 14.32015491 |
| 291 | LA02, 1, LA08, P, M1, F | 14.31637679 |
| 292 | a, LA08, M1, P, L***, F | 14.28954986 |
| 293 | LA02, M1, ML***, p, 1, F | 14.25635378 |
| 294 | MA, M1, ML***, p, M1, F | 14.25599002 |
| 295 | BHF, M1, L***, P, 1, F | 14.25275906 |
| 296 | BHF, M1, 1, P, 1, F | 14.23889246 |
| 297 | MA, LA08, ML***, p, 1, F | 14.23396924 |
| 298 | a, M1, L***, p, L***, F | 14.16251831 |
| 299 | A, M1, LA08, P, L***, F | 14.15268194 |
| 300 | A, 1, LA08, P, L***, F | 14.07794459 |
| 301 | BHF, LA08, 1, P, M1, F | 14.00927789 |
| 302 | Ma, ML***, L***, P, LA08, F | 13.98383886 |
| 303 | BHF, LA08, L***, P, L***, F | 13.96167677 |
| 304 | LA02, M1, BHF, p, M1, F | 13.94351241 |
| 305 | A, M1, M1, P, M1, F | 13.93909716 |
| 306 | BHF, 1, LA08, p, 1, F | 13.92082944 |
| 307 | A, M1, ML***, P, ML***, F | 13.85607019 |
| 308 | MA, ML***, LA08, p, M1, F | 13.8343356 |
| 309 | A, M1, M1, p, M1, F | 13.81799304 |
| 310 | BHF, 1, 1, P, M1, F | 13.80170138 |
| 311 | MA, M1, BHF, p, M1, F | 13.78906142 |
| 312 | BHF, 1, L***, P, 1, F | 13.77226775 |
| 313 | MA, 1, L***, p, 1, F | 13.74395145 |
| 314 | BHF, 1, BHF, p, M1, F | 13.73456859 |
| 315 | a, M1, 1, P, M1, F | 13.71285744 |
| 316 | BHF, 1, BHF, p, 1, F | 13.69640691 |
| 317 | A, M1, LA08, P, ML***, F | 13.68166075 |
| 318 | a, 1, L***, p, LA08, F | 13.64865683 |

| Compound No. | Peptomer Sequence | Permeability Value ($\times 10^{-6}$ cm/s) |
| --- | --- | --- |
| 319 | LA02, ML***, M1, P, 1, F | 13.62670989 |
| 320 | BHF, 1, LA08, P, 1, F | 13.60501049 |
| 321 | A, ML***, L***, p, 1, F | 13.59271209 |
| 322 | MA, 1, L***, p, LA08, F | 13.57036188 |
| 323 | BHF, M1, L***, p, L***, F | 13.56602015 |
| 324 | A, LA08, L***, P, M1, F | 13.54743987 |
| 325 | A, M1, LA08, p, M1, F | 13.53244538 |
| 326 | LA02, M1, M1, p, M1, F | 13.51585557 |
| 327 | A, M1, L***, p, LA08, F | 13.51368794 |
| 328 | LA02, M1, L***, p, 1, F | 13.51085873 |
| 329 | Ma, L***, 1, P, M1, F | 13.47557403 |
| 330 | A, LA08, 1, P, LA08, F | 13.46652765 |
| 331 | LA02, M1, 1, p, M1, F | 13.46651411 |
| 332 | A, M1, BHF, p, M1, F | 13.46034782 |
| 333 | A, 1, BHF, p, ML***, F | 13.42999756 |
| 334 | LA02, ML***, M1, p, M1, F | 13.41658601 |
| 335 | LA02, 1, L***, p, 1, F | 13.38203284 |
| 336 | MA, M1, LA08, p, ML***, F | 13.37827685 |
| 337 | LA02, ML***, M1, P, M1, F | 13.35044535 |
| 338 | LA02, M1, BHF, P, M1, F | 13.32074194 |
| 339 | LA02, LA08, M1, P, 1, F | 13.27845085 |
| 340 | LA02, M1, M1, p, LA08, F | 13.27788945 |
| 341 | LA02, ML***, LA08, p, M1, F | 13.26225567 |
| 342 | Ma, LA08, M1, p, 1, F | 13.24549565 |
| 343 | Ma, ML***, LA08, P, LA08, F | 13.23173168 |
| 344 | A, 1, LA08, P, M1, F | 13.22457132 |
| 345 | a, ML***, M1, P, LA08, F | 13.21467684 |
| 346 | LA02, ML***, 1, P, 1, F | 13.17537765 |
| 347 | MA, M1, LA08, P, LA08, F | 13.16825196 |
| 348 | BHF, 1, L***, P, ML***, F | 13.1671722 |
| 349 | A, L***, M1, P, ML***, F | 13.16677535 |
| 350 | Ma, M1, M1, p, M1, F | 13.15497613 |
| 351 | Ma, M1, L***, p, L***, F | 13.15137152 |
| 352 | a, LA08, M1, p, M1, F | 13.13765997 |
| 353 | a, ML***, LA08, p, M1, F | 13.11783791 |
| 354 | A, M1, M1, P, LA08, F | 13.0552946 |
| 355 | Ma, LA08, 1, p, ML***, F | 13.05294248 |
| 356 | BHF, 1, L***, p, M1, F | 13.02817814 |
| 357 | a, LA08, ML***, p, ML***, F | 12.99665604 |
| 358 | A, M1, ML***, p, LA08, F | 12.98699884 |
| 359 | BHF, 1, L***, P, LA08, F | 12.97614593 |
| 360 | BHF, M1, BHF, P, L***, F | 12.96211767 |
| 361 | MA, M1, M1, M1, P, F | 12.86418892 |
| 362 | A, M1, 1, p, L***, F | 12.83953132 |
| 363 | BHF, 1, ML***, P, 1, F | 12.83540366 |
| 364 | Ma, M1, ML***, p, M1, F | 12.82155693 |
| 365 | MA, 1, ML***, p, 1, F | 12.78167723 |
| 366 | LA02, L***, M1, p, 1, F | 12.77806535 |
| 367 | LA02, ML***, 1, p, LA08, F | 12.76568836 |
| 368 | A, LA08, L***, P, LA08, F | 12.75886886 |
| 369 | a, ML***, 1, p, 1, F | 12.74944654 |
| 370 | LA02, ML***, 1, p, M1, F | 12.72752444 |
| 371 | BHF, M1, BHF, P, 1, F | 12.60378433 |
| 372 | a, LA08, LA08, p, ML***, F | 12.59939348 |
| 373 | MA, M1, M1, M1, F | 12.54321102 |
| 374 | A, LA08, 1, p, 1, F | 12.48129444 |
| 375 | MA, 1, BHF, p, M1, F | 12.47101605 |
| 376 | MA, M1, 1, P, 1, F | 12.40018963 |
| 377 | Ma, M1, BHF, P, L***, F | 12.36119896 |
| 378 | A, M1, M1, p, M1, F | 12.35053235 |
| 379 | A, M1, BHF, p, 1, F | 12.34098032 |
| 380 | LA02, 1, LA08, p, M1, F | 12.33153725 |
| 381 | MA, 1, ML***, P, M1, F | 12.32844411 |
| 382 | BHF, L***, 1, p, M1, F | 12.29193608 |
| 383 | LA02, L***, LA08, P, M1, F | 12.29073611 |
| 384 | a, M1, 1, p, M1, F | 12.25785791 |
| 385 | Ma, 1, LA08, p, M1, F | 12.22560074 |
| 386 | MA, 1, L***, P, ML***, F | 12.21173435 |
| 387 | a, ML***, LA08, p, ML***, F | 12.20097919 |
| 388 | BHF, ML***, LA08, P, M1, F | 12.16312141 |
| 389 | A, ML***, 1, P, M1, F | 12.13945126 |
| 390 | Ma, ML***, 1, P, LA08, F | 12.05950752 |
| 391 | a, 1, BHF, p, ML***, F | 12.02350374 |
| 392 | A, LA08, ML***, P, LA08, F | 12.02339437 |
| 393 | a, 1, ML***, p, LA08, F | 11.98988226 |
| 394 | Ma, 1, LA08, P, LA08, F | 11.97735999 |
| 395 | Ma, M1, L***, p, ML***, F | 11.97433204 |
| 396 | Ma, M1, M1, P, M1, F | 11.95760508 |
| 397 | A, LA08, M1, P, LA08, F | 11.94247557 |
| 398 | BHF, 1, 1, P, 1, F | 11.93620769 |
| 399 | MA, 1, LA08, p, ML***, F | 11.91440886 |
| 400 | Ma, L***, LA08, P, LA08, F | 11.90580391 |
| 401 | LA02, L***, L***, p, M1, F | 11.89457829 |
| 402 | A, LA08, LA08, p, L***, F | 11.8916768 |
| 403 | LA02, 1, 1, P, M1, F | 11.89148268 |
| 404 | Ma, M1, LA08, p, ML***, F | 11.87951487 |
| 405 | Ma, ML***, L***, p, LA08, F | 11.8657429 |
| 406 | BHF, LA08, M1, p, M1, F | 11.86354209 |
| 407 | BHF, 1, L***, p, ML***, F | 11.8465143 |
| 408 | MA, L***, BHF, p, L***, F | 11.81568914 |
| 409 | LA02, M1, M1, p, M1, F | 11.81300096 |
| 410 | A, L***, 1, P, LA08, F | 11.80634988 |
| 411 | LA02, 1, BHF, p, M1, F | 11.78306695 |
| 412 | a, ML***, ML***, P, LA08, F | 11.76930838 |
| 413 | A, 1, L***, P, M1, F | 11.75739516 |
| 414 | MA, ML***, LA08, p, LA08, F | 11.75012842 |
| 415 | MA, 1, M1, p, LA08, F | 11.7066321 |
| 416 | A, 1, LA08, p, ML***, F | 11.69139032 |
| 417 | Ma, 1, ML***, p, 1, F | 11.69018972 |
| 418 | Ma, LA08, L***, p, M1, F | 11.68097375 |
| 419 | A, 1, M1, P, M1, F | 11.67215468 |
| 420 | A, M1, M1, p, M1, F | 11.6708824 |
| 421 | a, ML***, 1, P, ML***, F | 11.62755806 |
| 422 | LA02, L***, L***, P, LA08, F | 11.60051198 |
| 423 | MA, L***, L***, P, M1, F | 11.58242904 |
| 424 | LA02, 1, ML***, p, L***, F | 11.53970127 |
| 425 | a, M1, BHF, P, L***, F | 11.53741255 |
| 426 | LA02, M1, LA08, p, M1, F | 11.50816966 |
| 427 | BHF, LA08, 1, P, L***, F | 11.49086837 |
| 428 | A, L***, LA08, P, LA08, F | 11.46140752 |
| 429 | A, M1, LA08, p, M1, F | 11.45827993 |
| 430 | BHF, M1, M1, p, M1, F | 11.43468181 |
| 431 | MA, 1, LA08, P, M1, F | 11.41533436 |
| 432 | MA, LA08, L***, p, ML***, F | 11.39463489 |
| 433 | a, L***, M1, P, L***, F | 11.38840445 |
| 434 | Ma, M1, M1, P, M1, F | 11.38484272 |
| 435 | a, LA08, L***, P, L***, F | 11.37202846 |
| 436 | A, ML***, 1, P, L***, F | 11.34763032 |
| 437 | MA, L***, 1, P, M1, F | 11.3403253 |
| 438 | LA02, 1, ML***, P, LA08, F | 11.31935215 |
| 439 | A, M1, M1, P, 1, F | 11.31550664 |
| 440 | MA, M1, ML***, p, LA08, F | 11.31270331 |
| 441 | MA, M1, L***, p, LA08, F | 11.26658443 |
| 442 | A, 1, LA08, P, ML***, F | 11.25340711 |
| 443 | a, LA08, 1, P, L***, F | 11.24073126 |
| 444 | LA02, LA08, ML***, P, M1, F | 11.2240681 |
| 445 | MA, ML***, L***, p, LA08, F | 11.21773269 |
| 446 | LA02, M1, ML***, P, 1, F | 11.2038765 |
| 447 | LA02, 1, ML***, p, 1, F | 11.19139945 |
| 448 | A, M1, LA08, p, L***, F | 11.17294641 |
| 449 | Ma, 1, ML***, p, M1, F | 11.17154455 |
| 450 | MA, 1, 1, p, 1, F | 11.15483763 |
| 451 | A, M1, L***, p, L***, F | 11.15384133 |
| 452 | Ma, 1, L***, p, ML***, F | 11.14084235 |
| 453 | a, LA08, L***, P, LA08, F | 11.13170381 |
| 454 | BHF, ML***, ML***, P, LA08, F | 11.1300007 |
| 455 | LA02, LA08, 1, p, L***, F | 11.12077509 |
| 456 | LA02, LA08, M1, P, LA08, F | 11.11239467 |
| 457 | A, M1, M1, p, M1, F | 11.10605987 |
| 458 | a, M1, LA08, P, M1, F | 11.08040848 |
| 459 | Ma, L***, LA08, p, M1, F | 11.06700862 |
| 460 | a, 1, ML***, p, ML***, F | 11.05716762 |
| 461 | A, L***, LA08, p, L***, F | 11.04762588 |
| 462 | LA02, M1, LA08, p, M1, F | 11.01911964 |
| 463 | Ma, LA08, 1, p, ML***, F | 11.00753821 |
| 464 | a, M1, M1, P, M1, F | 10.99483912 |
| 465 | A, ML***, 1, P, ML***, F | 10.99059111 |
| 466 | MA, M1, 1, p, M1, F | 10.98389537 |
| 467 | Ma, 1, L***, p, M1, F | 10.96931203 |
| 468 | MA, LA08, ML***, p, ML***, F | 10.95272724 |

| Compound No. | Peptomer Sequence | Permeability Value (×10⁻⁶ cm/s) |
|---|---|---|
| 469 | LA02, 1, BHF, P, L***, F | 10.94048337 |
| 470 | BHF, M1, BHF, p, 1, F | 10.90683173 |
| 471 | MA, 1, L***, P, M1, F | 10.89476174 |
| 472 | LA02, L***, ML***, p, M1, F | 10.85672407 |
| 473 | LA02, M1, L***, p, M1, F | 10.81739315 |
| 474 | LA02, 1, L***, p, LA08, F | 10.81720781 |
| 475 | Ma, LA08, L***, p, ML***, F | 10.81173878 |
| 476 | Ma, M1, LA08, p, 1, F | 10.80968441 |
| 477 | LA02, M1, LA08, p, LA08, F | 10.8082134 |
| 478 | MA, LA08, L***, p, L***, F | 10.80759226 |
| 479 | LA02, LA08, L***, p, L***, F | 10.76342435 |
| 480 | BHF, 1, ML***, P, ML***, F | 10.74069253 |
| 481 | Ma, 1, LA08, P, M1, F | 10.67978794 |
| 482 | a, M1, LA08, P, ML***, F | 10.66489775 |
| 483 | BHF, LA08, 1, p, 1, F | 10.65589664 |
| 484 | A, LA08, 1, P, L***, F | 10.64954297 |
| 485 | LA02, M1, L***, p, LA08, F | 10.64731224 |
| 486 | A, L***, LA08, P, M1, F | 10.61764419 |
| 487 | A, 1, 1, p, 1, F | 10.616968 |
| 488 | LA02, M1, LA08, p, M1, F | 10.61411526 |
| 489 | LA02, M1, BHF, p, 1, F | 10.61411526 |
| 490 | BHF, 1, ML***, P, L***, F | 10.61055238 |
| 491 | BHF, M1, BHF, p, M1, F | 10.60337842 |
| 492 | BHF, ML***, LA08, P, 1, F | 10.59249394 |
| 493 | BHF, L***, BHF, P, L***, F | 10.58270593 |
| 494 | a, LA08, BHF, P, 1, F | 10.56527141 |
| 495 | MA, M1, LA08, p, M1, F | 10.54209193 |
| 496 | BHF, 1, LA08, P, L***, F | 10.52391316 |
| 497 | A, M1, BHF, p, M1, F | 10.49832262 |
| 498 | A, M1, ML***, p, 1, F | 10.48610492 |
| 499 | MA, LA08, 1, P, 1, F | 10.47587086 |
| 500 | LA02, ML***, 1, p, 1, F | 10.47248244 |
| 501 | A, 1, L***, P, ML***, F | 10.4452417 |
| 502 | Ma, M1, M1, P, M1, F | 10.44310076 |
| 503 | MA, M1, LA08, p, ML***, F | 10.38960721 |
| 504 | BHF, M1, BHF, p, M1, F | 10.38811427 |
| 505 | LA02, LA08, L***, P, ML***, F | 10.38303635 |
| 506 | a, ML***, LA08, P, 1, F | 10.38125717 |
| 507 | LA02, M1, LA08, p, 1, F | 10.35501938 |
| 508 | A, ML***, BHF, p, 1, F | 10.34392486 |
| 509 | LA02, ML***, ML***, p, 1, F | 10.33568023 |
| 510 | A, 1, ML***, p, L***, F | 10.31645393 |
| 511 | A, 1, L***, p, ML***, F | 10.30829187 |
| 512 | a, ML***, L***, p, M1, F | 10.30294089 |
| 513 | Ma, ML***, LA08, p, LA08, F | 10.30260088 |
| 514 | A, ML***, M1, P, 1, F | 10.29020859 |
| 515 | LA02, M1, ML***, P, LA08, F | 10.23700271 |
| 516 | LA02, LA08, 1, P, 1, F | 10.22478091 |
| 517 | LA02, 1, M1, P, 1, F | 10.19247245 |
| 518 | LA02, 1, M1, P, 1, F | 10.19247245 |
| 519 | BHF, M1, BHF, P, 1, F | 10.0880796 |
| 520 | LA02, M1, LA08, p, LA08, F | 9.987721562 |
| 521 | LA02, ML***, M1, p, 1, F | 9.985820738 |
| 522 | LA02, 1, LA08, p, ML***, F | 9.975015248 |
| 523 | MA, M1, L***, p, ML***, F | 9.964912872 |
| 524 | A, 1, LA08, P, 1, F | 9.962388042 |
| 525 | A, LA08, M1, P, M1, F | 9.952205367 |
| 526 | a, M1, L***, P, 1, F | 9.855274575 |
| 527 | a, M1, ML***, p, LA08, F | 9.839043457 |
| 528 | LA02, 1, 1, p, ML***, F | 9.825155355 |
| 529 | A, 1, 1, P, LA08, F | 9.812290975 |
| 530 | Ma, 1, L***, p, LA08, F | 9.778237191 |
| 531 | LA02, LA08, M1, P, 1, F | 9.77761088 |
| 532 | A, M1, ML***, p, L***, F | 9.770813193 |
| 533 | Ma, 1, L***, p, 1, F | 9.764531664 |
| 534 | MA, M1, ML***, p, L***, F | 9.750745143 |
| 535 | LA02, 1, ML***, p, ML***, F | 9.739676705 |
| 536 | LA02, M1, M1, p, M1, F | 9.72873097 |
| 537 | LA02, L***, LA08, P, LA08, F | 9.720623957 |
| 538 | MA, M1, M1, p, M1, F | 9.688707921 |
| 539 | LA02, M1, LA08, P, ML***, F | 9.672273612 |
| 540 | LA02, LA08, 1, p, 1, F | 9.632201764 |
| 541 | LA02, LA08, 1, p, M1, F | 9.631578926 |
| 542 | a, ML***, L***, P, 1, F | 9.610381805 |
| 543 | Ma, L***, M1, p, LA08, F | 9.598223554 |
| 544 | Ma, L***, L***, P, M1, F | 9.576568139 |
| 545 | MA, 1, LA08, P, M1, F | 9.569340747 |
| 546 | BHF, LA08, M1, p, 1, F | 9.565372495 |
| 547 | A, LA08, LA08, P, LA08, F | 9.558499572 |
| 548 | a, LA08, BHF, P, L***, F | 9.513743034 |
| 549 | LA02, M1, L***, p, LA08, F | 9.454798609 |
| 550 | A, LA08, ML***, P, LA08, F | 9.450444361 |
| 551 | Ma, M1, LA08, P, LA08, F | 9.447880793 |
| 552 | a, LA08, M1, p, LA08, F | 9.432127808 |
| 553 | BHF, LA08, M1, P, L***, F | 9.358572929 |
| 554 | a, M1, 1, p, LA08, F | 9.312301232 |
| 555 | Ma, M1, ML***, p, LA08, F | 9.305536018 |
| 556 | A, LA08, M1, P, 1, F | 9.275517312 |
| 557 | A, L***, L***, P, LA08, F | 9.266477273 |
| 558 | LA02, ML***, BHF, p, 1, F | 9.240056979 |
| 559 | a, M1, BHF, P, ML***, F | 9.195542246 |
| 560 | BHF, 1, BHF, p, LA08, F | 9.169735085 |
| 561 | MA, 1, 1, P, 1, F | 9.156141386 |
| 562 | BHF, M1, L***, P, ML***, F | 9.128480075 |
| 563 | BHF, 1, BHF, p, ML***, F | 9.06582977 |
| 564 | A, LA08, BHF, P, L***, F | 9.060761253 |
| 565 | a, ML***, M1, p, LA08, F | 9.048478377 |
| 566 | LA02, ML***, L***, p, M1, F | 9.047716444 |
| 567 | Ma, L***, ML***, P, 1, F | 9.021357089 |
| 568 | LA02, ML***, 1, p, L***, F | 8.993329364 |
| 569 | A, LA08, LA08, p, LA08, F | 8.989392592 |
| 570 | BHF, L***, M1, P, 1, F | 8.988047245 |
| 571 | MA, M1, M1, p, M1, F | 8.974656881 |
| 572 | BHF, ML***, 1, p, M1, F | 8.957058001 |
| 573 | MA, 1, ML***, p, M1, F | 8.949936716 |
| 574 | A, ML***, LA08, p, LA08, F | 8.949298386 |
| 575 | A, L***, L***, P, M1, F | 8.924944906 |
| 576 | MA, 1, 1, P, M1, F | 8.923494816 |
| 577 | MA, 1, BHF, p, 1, F | 8.850533896 |
| 578 | a, LA08, M1, P, 1, F | 8.84662479 |
| 579 | MA, 1, L***, P, LA08, F | 8.843453166 |
| 580 | a, M1, L***, p, LA08, F | 8.843156174 |
| 581 | BHF, M1, L***, P, L***, F | 8.837774041 |
| 582 | LA02, M1, BHF, p, M1, F | 8.801827256 |
| 583 | LA02, 1, LA08, p, L***, F | 8.799123611 |
| 584 | a, L***, M1, P, ML***, F | 8.783351487 |
| 585 | BHF, LA08, L***, p, 1, F | 8.764049129 |
| 586 | Ma, M1, LA08, P, LA08, F | 8.757968504 |
| 587 | BHF, L***, L***, P, M1, F | 8.708349082 |
| 588 | BHF, 1, LA08, p, M1, F | 8.698036413 |
| 589 | BHF, 1, L***, p, LA08, F | 8.666959869 |
| 590 | A, 1, ML***, P, 1, F | 8.649168455 |
| 591 | BHF, 1, L***, p, LA08, F | 8.624324092 |
| 592 | A, LA08, L***, P, LA08, F | 8.615162882 |
| 593 | LA02, LA08, M1, p, LA08, F | 8.589641782 |
| 594 | a, M1, BHF, ML***, F | 8.573690092 |
| 595 | LA02, L***, L***, p, LA08, F | 8.567734244 |
| 596 | Ma, M1, L***, p, LA08, F | 8.510300222 |
| 597 | BHF, 1, L***, p, 1, F | 8.478559661 |
| 598 | MA, LA08, M1, p, 1, F | 8.476980949 |
| 599 | LA02, M1, LA08, p, ML***, F | 8.453291457 |
| 600 | A, 1, M1, p, ML***, F | 8.423428825 |
| 601 | BHF, M1, L***, P, M1, F | 8.416794288 |
| 602 | A, LA08, M1, P, LA08, F | 8.379323649 |
| 603 | a, LA08, 1, p, ML***, F | 8.37012376 |
| 604 | Ma, 1, 1, P, 1, F | 8.346444716 |
| 605 | Ma, M1, M1, p, M1, F | 8.332435709 |
| 606 | Ma, 1, BHF, P, ML***, F | 8.30570999 |
| 607 | Ma, 1, L***, P, 1, F | 8.269826169 |
| 608 | MA, ML***, L***, p, 1, F | 8.261007071 |
| 609 | A, LA08, 1, p, L***, F | 8.2447995 |
| 610 | a, L***, M1, P, LA08, F | 8.228769492 |
| 611 | LA02, LA08, BHF, P, M1, F | 8.216852927 |
| 612 | a, ML***, 1, p, LA08, F | 8.203081879 |
| 613 | LA02, LA08, M1, p, M1, F | 8.191493245 |
| 614 | MA, 1, LA08, p, M1, F | 8.145248107 |
| 615 | LA02, M1, BHF, P, M1, F | 8.127230269 |
| 616 | LA02, M1, L***, P, LA08, F | 8.118609252 |
| 617 | a, M1, BHF, p, 1, F | 8.102601635 |
| 618 | LA02, LA08, BHF, P, 1, F | 8.091902464 |

| Compound No. | Peptomer Sequence | Permeability Value ($\times 10^{-6}$ cm/s) |
|---|---|---|
| 619 | LA02, M1, M1, p, M1, F | 8.087341698 |
| 620 | BHF, 1, BHF, P, ML***, F | 8.087125042 |
| 621 | MA, LA08, L***, p, 1, F | 8.085861541 |
| 622 | Ma, LA08, L***, P, 1, F | 8.054472566 |
| 623 | a, LA08, L***, P, LA08, F | 8.048127709 |
| 624 | A, L***, M1, p, M1, F | 8.046713312 |
| 625 | LA02, ML***, LA08, p, LA08, F | 8.046674225 |
| 626 | A, 1, LA08, P, LA08, F | 8.044443501 |
| 627 | LA02, LA08, ML***, P, 1, F | 8.019399396 |
| 628 | BHF, M1, BHF, p, M1, F | 8.010904406 |
| 629 | LA02, ML***, L***, p, 1, F | 8.004570537 |
| 630 | Ma, L***, M1, p, 1, F | 7.993062212 |
| 631 | LA02, M1, LA08, p, ML***, F | 7.97665354 |
| 632 | MA, M1, M1, p, M1, F | 7.937880559 |
| 633 | a, ML***, 1, p, M1, F | 7.893355922 |
| 634 | A, ML***, L***, P, 1, F | 7.867367418 |
| 635 | Ma, 1, 1, p, 1, F | 7.864537078 |
| 636 | BHF, M1, M1, P, M1, F | 7.851231014 |
| 637 | LA02, LA08, LA08, p, 1, F | 7.837222558 |
| 638 | a, ML***, 1, P, M1, F | 7.813251831 |
| 639 | a, M1, BHF, P, 1, F | 7.793065895 |
| 640 | a, LA08, L***, P, LA08, F | 7.758108471 |
| 641 | LA02, 1, LA08, P, LA08, F | 7.748292417 |
| 642 | LA02, 1, 1, P, LA08, F | 7.731597276 |
| 643 | LA02, M1, M1, p, LA08, F | 7.730253597 |
| 644 | LA02, M1, LA08, p, LA08, F | 7.688530783 |
| 645 | MA, 1, LA08, P, LA08, F | 7.674105266 |
| 646 | A, 1, LA08, p, M1, F | 7.628702763 |
| 647 | A, L***, M1, P, M1, F | 7.623092282 |
| 648 | Ma, ML***, BHF, p, LA08, F | 7.615059868 |
| 649 | MA, ML***, BHF, p, LA08, F | 7.607566237 |
| 650 | MA, L***, ML***, p, LA08, F | 7.599284711 |
| 651 | a, M1, M1, P, M1, F | 7.59776048 |
| 652 | Ma, M1, M1, p, M1, F | 7.594492079 |
| 653 | a, L***, M1, P, 1, F | 7.575968604 |
| 654 | A, M1, LA08, p, M1, F | 7.56853665 |
| 655 | Ma, L***, 1, P, LA08, F | 7.553279146 |
| 656 | Ma, 1, 1, P, L***, F | 7.54894806 |
| 657 | Ma, 1, 1, p, LA08, F | 7.465613977 |
| 658 | MA, M1, LA08, p, LA08, F | 7.464612233 |
| 659 | BHF, M1, 1, p, M1, F | 7.453519149 |
| 660 | LA02, LA08, 1, P, LA08, F | 7.43726545 |
| 661 | LA02, 1, BHF, p, L***, F | 7.429402282 |
| 662 | LA02, LA08, LA08, p, 1, F | 7.419630776 |
| 663 | LA02, 1, M1, p, M1, F | 7.402734165 |
| 664 | LA02, M1, ML***, p, ML***, F | 7.391575169 |
| 665 | A, LA08, ML***, P, M1, F | 7.34042489 |
| 666 | a, M1, ML***, p, L***, F | 7.323662362 |
| 667 | a, LA08, LA08, p, 1, F | 7.302210643 |
| 668 | BHF, ML***, LA08, P, 1, F | 7.293312811 |
| 669 | BHF, L***, ML***, p, LA08, F | 7.267970912 |
| 670 | BHF, 1, BHF, P, 1, F | 7.266800993 |
| 671 | MA, L***, LA08, p, LA08, F | 7.258863301 |
| 672 | A, 1, LA08, p, L***, F | 7.225489084 |
| 673 | BHF, 1, 1, P, LA08, F | 7.212470041 |
| 674 | a, L***, LA08, P, LA08, F | 7.188958972 |
| 675 | LA02, LA08, LA08, P, LA08, F | 7.175169234 |
| 676 | LA02, LA08, LA08, P, L***, F | 7.160087694 |
| 677 | LA02, L***, L***, p, LA08, F | 7.115171485 |
| 678 | a, L***, 1, P, M1, F | 7.113170196 |
| 679 | BHF, LA08, 1, P, 1, F | 7.041035412 |
| 680 | A, L***, 1, P, M1, F | 7.040603365 |
| 681 | a, M1, 1, P, 1, F | 7.03870328 |
| 682 | LA02, ML***, LA08, P, LA08, F | 7.035647254 |
| 683 | Ma, ML***, 1, P, 1, F | 7.017011869 |
| 684 | a, M1, LA08, p, LA08, F | 7.011283929 |
| 685 | A, L***, 1, p, M1, F | 6.975808294 |
| 686 | Ma, LA08, L***, P, 1, F | 6.959702972 |
| 687 | LA02, ML***, LA08, P, LA08, F | 6.943695894 |
| 688 | BHF, L***, BHF, p, M1, F | 6.935705496 |
| 689 | a, ML***, 1, p, L***, F | 6.917928868 |
| 690 | Ma, L***, M1, p, L***, F | 6.916143735 |
| 691 | LA02, 1, BHF, p, M1, F | 6.903212049 |
| 692 | Ma, 1, BHF, p, LA08, F | 6.882744451 |
| 693 | A, L***, LA08, P, 1, F | 6.875531808 |
| 694 | Ma, L***, LA08, P, LA08, F | 6.824900307 |
| 695 | a, L***, 1, P, ML***, F | 6.822741577 |
| 696 | A, LA08, 1, P, LA08, F | 6.81157788 |
| 697 | BHF, L***, M1, P, ML***, F | 6.809746689 |
| 698 | LA02, ML***, BHF, P, L***, F | 6.791270429 |
| 699 | BHF, L***, ML***, P, 1, F | 6.755272298 |
| 700 | LA02, M1, L***, p, ML***, F | 6.749230183 |
| 701 | LA02, M1, ML***, p, M1, F | 6.747900026 |
| 702 | BHF, L***, LA08, P, 1, F | 6.720235555 |
| 703 | MA, 1, BHF, p, LA08, F | 6.685521839 |
| 704 | A, L***, LA08, p, 1, F | 6.682576235 |
| 705 | LA02, L***, BHF, P, L***, F | 6.681723993 |
| 706 | MA, M1, 1, P, LA08, F | 6.654625468 |
| 707 | LA02, 1, M1, p, M1, F | 6.603141301 |
| 708 | a, 1, BHF, p, 1, F | 6.601010658 |
| 709 | BHF, L***, L***, P, LA08, F | 6.596594725 |
| 710 | LA02, LA08, BHF, P, L***, F | 6.590767157 |
| 711 | a, LA08, 1, P, LA08, F | 6.542426979 |
| 712 | a, M1, 1, P, L***, F | 6.532408763 |
| 713 | BHF, 1, BHF, P, LA08, F | 6.499409236 |
| 714 | LA02, L***, 1, P, 1, F | 6.436337086 |
| 715 | BHF, LA08, BHF, P, L***, F | 6.320166945 |
| 716 | A, LA08, ML***, P, ML***, F | 6.291937124 |
| 717 | a, 1, LA08, P, LA08, F | 6.253940796 |
| 718 | LA02, 1, L***, p, L***, F | 6.250077616 |
| 719 | BHF, M1, BHF, P, 1, F | 6.245065973 |
| 720 | a, 1, BHF, p, M1, F | 6.230284798 |
| 721 | BHF, LA08, 1, P, M1, F | 6.204256998 |
| 722 | A, ML***, LA08, p, M1, F | 6.186737279 |
| 723 | MA, L***, L***, p, M1, F | 6.180292332 |
| 724 | A, M1, BHF, P, L***, F | 6.173418821 |
| 725 | BHF, L***, ML***, P, LA08, F | 6.166490266 |
| 726 | BHF, LA08, M1, p, M1, F | 6.152430163 |
| 727 | LA02, L***, BHF, p, 1, F | 6.127555176 |
| 728 | a, LA08, ML***, p, ML***, F | 6.114988928 |
| 729 | A, LA08, ML***, P, 1, F | 6.102511913 |
| 730 | A, M1, M1, p, M1, F | 6.094306779 |
| 731 | LA02, LA08, L***, p, LA08, F | 6.080538292 |
| 732 | BHF, 1, ML***, p, LA08, F | 6.073384376 |
| 733 | Ma, L***, L***, p, M1, F | 6.062607317 |
| 734 | LA02, M1, M1, P, M1, F | 6.043175019 |
| 735 | BHF, M1, 1, P, ML***, F | 6.039999151 |
| 736 | Ma, M1, L***, p, 1, F | 6.038344336 |
| 737 | BHF, LA08, ML***, P, L***, F | 6.029179956 |
| 738 | BHF, ML***, M1, p, M1, F | 5.962395369 |
| 739 | a, 1, LA08, p, ML***, F | 5.952173707 |
| 740 | a, M1, LA08, P, L***, F | 5.952015047 |
| 741 | LA02, LA08, 1, p, L***, F | 5.849625283 |
| 742 | BHF, 1, L***, p, ML***, F | 5.8405699 |
| 743 | LA02, 1, L***, p, L***, F | 5.834238188 |
| 744 | A, 1, 1, p, LA08, F | 5.801327507 |
| 745 | LA02, L***, M1, p, LA08, F | 5.796177059 |
| 746 | MA, ML***, BHF, p, LA08, F | 5.796105762 |
| 747 | a, L***, L***, P, LA08, F | 5.774621052 |
| 748 | BHF, L***, 1, P, LA08, F | 5.762289714 |
| 749 | LA02, M1, 1, P, LA08, F | 5.732089574 |
| 750 | MA, M1, L***, p, 1, F | 5.729766862 |
| 751 | a, LA08, 1, p, M1, F | 5.722356207 |
| 752 | LA02, L***, 1, p, 1, F | 5.681169623 |
| 753 | Ma, M1, BHF, P, 1, F | 5.679997044 |
| 754 | MA, LA08, ML***, P, M1, F | 5.642892187 |
| 755 | MA, LA08, 1, p, LA08, F | 5.628456201 |
| 756 | Ma, M1, BHF, p, 1, F | 5.6180916 |
| 757 | BHF, M1, L***, p, 1, F | 5.614251779 |
| 758 | LA02, M1, BHF, p, M1, F | 5.604317419 |
| 759 | BHF, 1, 1, p, L***, F | 5.598423026 |
| 760 | a, LA08, BHF, p, ML***, F | 5.595643211 |
| 761 | a, M1, M1, P, M1, F | 5.58553753 |
| 762 | BHF, M1, L***, p, 1, F | 5.582865938 |
| 763 | a, LA08, 1, p, LA08, F | 5.564052656 |
| 764 | Ma, L***, 1, p, LA08, F | 5.54833614 |
| 765 | LA02, ML***, M1, P, LA08, F | 5.539608771 |
| 766 | BHF, LA08, BHF, p, 1, F | 5.523929465 |
| 767 | A, L***, M1, P, 1, F | 5.498324786 |
| 768 | A, M1, 1, P, 1, F | 5.467952168 |

-continued

| Compound No. | Peptomer Sequence | Permeability Value (×10⁻⁶ cm/s) |
|---|---|---|
| 769 | Ma, ML***, LA08, p, M1, F | 5.462668405 |
| 770 | A, ML***, LA08, P, 1, F | 5.450254902 |
| 771 | a, LA08, LA08, p, 1, F | 5.3981743 |
| 772 | BHF, L***, LA08, p, M1, F | 5.384658442 |
| 773 | Ma, 1, BHF, P, M1, F | 5.37358175 |
| 774 | A, 1, BHF, P, 1, F | 5.333276911 |
| 775 | a, ML***, BHF, P, LA08, F | 5.322246179 |
| 776 | A, M1, LA08, p, M1, F | 5.303308773 |
| 777 | BHF, M1, LA08, p, L***, F | 5.299551298 |
| 778 | LA02, 1, M1, P, M1, F | 5.291625049 |
| 779 | Ma, LA08, ML***, P, 1, F | 5.279177817 |
| 780 | LA02, M1, 1, p, 1, F | 5.276656133 |
| 781 | BHF, ML***, LA08, p, LA08, F | 5.268923867 |
| 782 | MA, 1, LA08, p, LA08, F | 5.259222912 |
| 783 | Ma, ML***, BHF, p, 1, F | 5.255010107 |
| 784 | Ma, LA08, BHF, P, L***, F | 5.251781145 |
| 785 | LA02, 1, 1, p, LA08, F | 5.237026512 |
| 786 | a, L***, 1, p, M1, F | 5.197078286 |
| 787 | Ma, 1, L***, P, LA08, F | 5.18849604 |
| 788 | LA02, ML***, 1, P, L***, F | 5.170969683 |
| 789 | LA02, 1, BHF, p, L***, F | 5.163029145 |
| 790 | BHF, LA08, L***, p, M1, F | 5.157084708 |
| 791 | LA02, M1, LA08, p, ML***, F | 5.140152542 |
| 792 | MA, M1, M1, P, M1, F | 5.125129024 |
| 793 | BHF, LA08, LA08, p, 1, F | 5.110278738 |
| 794 | A, 1, 1, P, M1, F | 5.110183983 |
| 795 | a, L***, 1, p, LA08, F | 5.05005887 |
| 796 | a, M1, BHF, P, LA08, F | 5.026004109 |
| 797 | MA, L***, 1, p, L***, F | 5.022181461 |
| 798 | BHF, M1, 1, P, M1, F | 5.014468783 |
| 799 | a, LA08, M1, p, 1, F | 5.01218403 |
| 800 | A, 1, BHF, P, ML***, F | 5.008957941 |
| 801 | A, LA08, M1, p, L***, F | 4.999599179 |
| 802 | MA, M1, LA08, p, L***, F | 4.987967246 |
| 803 | MA, M1, BHF, P, ML***, F | 4.98242252 |
| 804 | A, LA08, 1, P, 1, F | 4.971700529 |
| 805 | A, 1, L***, P, L***, F | 4.955513875 |
| 806 | BHF, M1, ML***, P, ML***, F | 4.949040241 |
| 807 | MA, M1, M1, P, M1, F | 4.925309949 |
| 808 | MA, ML***, BHF, p, 1, F | 4.92064853 |
| 809 | A, 1, BHF, P, LA08, F | 4.920431357 |
| 810 | a, 1, BHF, P, ML***, F | 4.918630557 |
| 811 | a, LA08, M1, P, LA08, F | 4.887620717 |
| 812 | BHF, M1, 1, p, ML***, F | 4.853776703 |
| 813 | a, L***, M1, p, 1, F | 4.818220363 |
| 814 | a, 1, BHF, P, LA08, F | 4.798780921 |
| 815 | a, LA08, L***, p, L***, F | 4.730771203 |
| 816 | LA02, 1, 1, P, M1, F | 4.679523254 |
| 817 | A, 1, BHF, p, M1, F | 4.661421409 |
| 818 | BHF, L***, LA08, p, LA08, F | 4.650276938 |
| 819 | LA02, 1, LA08, p, LA08, F | 4.645548262 |
| 820 | MA, L***, L***, p, LA08, F | 4.645204105 |
| 821 | BHF, L***, M1, p, ML***, F | 4.560491954 |
| 822 | A, 1, 1, P, L***, F | 4.558809103 |
| 823 | MA, L***, BHF, p, LA08, F | 4.558093826 |
| 824 | BHF, M1, L***, p, ML***, F | 4.540809527 |
| 825 | BHF, L***, L***, P, 1, F | 4.496476521 |
| 826 | a, M1, M1, P, M1, F | 4.489806331 |
| 827 | MA, 1, M1, P, 1, F | 4.481489595 |
| 828 | Ma, L***, 1, p, M1, F | 4.439123536 |
| 829 | LA02, LA08, LA08, p, LA08, F | 4.413765128 |
| 830 | LA02, L***, L***, P, 1, F | 4.397697324 |
| 831 | LA02, 1, 1, p, L***, F | 4.379675726 |
| 832 | A, L***, 1, P, 1, F | 4.343619858 |
| 833 | MA, 1, LA08, P, L***, F | 4.292368636 |
| 834 | a, 1, L***, P, LA08, F | 4.292139985 |
| 835 | Ma, 1, LA08, P, LA08, F | 4.285097752 |
| 836 | LA02, L***, LA08, p, L***, F | 4.230986934 |
| 837 | a, LA08, 1, P, 1, F | 4.207597614 |
| 838 | Ma, 1, ML***, p, L***, F | 4.20015786 |
| 839 | BHF, M1, M1, P, 1, F | 4.186196982 |
| 840 | a, ML***, BHF, P, 1, F | 4.18179341 |
| 841 | BHF, M1, 1, p, ML***, F | 4.157185489 |
| 842 | LA02, LA08, LA08, P, L***, F | 4.140926176 |
| 843 | Ma, 1, LA08, p, LA08, F | 4.138746826 |
| 844 | MA, LA08, LA08, P, LA08, F | 4.06024523 |
| 845 | a, 1, LA08, P, M1, F | 4.047409136 |
| 846 | BHF, L***, M1, P, LA08, F | 4.027404683 |
| 847 | A, 1, 1, p, ML***, F | 3.998229076 |
| 848 | MA, L***, L***, P, M1, F | 3.99591015 |
| 849 | Ma, LA08, BHF, p, ML***, F | 3.986868127 |
| 850 | LA02, M1, BHF, p, M1, F | 3.943742224 |
| 851 | A, M1, BHF, P, 1, F | 3.940021 |
| 852 | A, ML***, 1, p, L***, F | 3.9357447 |
| 853 | A, ML***, 1, p, M1, F | 3.933263636 |
| 854 | A, 1, ML***, P, 1, F | 3.912148737 |
| 855 | a, M1, BHF, p, M1, F | 3.822583984 |
| 856 | MA, 1, BHF, p, ML***, F | 3.816794499 |
| 857 | MA, M1, M1, P, M1, F | 3.799446452 |
| 858 | BHF, M1, M1, P, M1, F | 3.792816741 |
| 859 | MA, M1, 1, p, L***, F | 3.78573774 |
| 860 | a, LA08, LA08, p, LA08, F | 3.779480912 |
| 861 | BHF, L***, BHF, P, ML***, F | 3.77844294 |
| 862 | Ma, 1, 1, P, M1, F | 3.75684075 |
| 863 | BHF, ML***, LA08, p, M1, F | 3.702677784 |
| 864 | a, L***, L***, P, M1, F | 3.701467648 |
| 865 | a, 1, LA08, p, M1, F | 3.68847873 |
| 866 | a, L***, 1, p, 1, F | 3.680001237 |
| 867 | Ma, L***, LA08, p, LA08, F | 3.674158941 |
| 868 | LA02, 1, BHF, P, LA08, F | 3.672058035 |
| 869 | LA02, 1, 1, p, M1, F | 3.670730924 |
| 870 | A, L***, L***, P, 1, F | 3.661227149 |
| 871 | MA, L***, 1, P, 1, F | 3.648335683 |
| 872 | BHF, ML***, LA08, p, 1, F | 3.646265202 |
| 873 | A, ML***, 1, p, 1, F | 3.639896025 |
| 874 | BHF, M1, M1, P, 1, F | 3.614011685 |
| 875 | MA, ML***, L***, P, 1, F | 3.613970739 |
| 876 | a, LA08, ML***, p, LA08, F | 3.565440407 |
| 877 | LA02, ML***, L***, p, LA08, F | 3.513531711 |
| 878 | a, M1, LA08, p, 1, F | 3.509375384 |
| 879 | MA, M1, BHF, p, 1, F | 3.47207946 |
| 880 | LA02, LA08, L***, p, ML***, F | 3.468532214 |
| 881 | A, M1, 1, p, L***, F | 3.467292771 |
| 882 | Ma, M1, LA08, p, LA08, F | 3.449848179 |
| 883 | LA02, ML***, LA08, p, L***, F | 3.422626161 |
| 884 | a, M1, 1, p, 1, F | 3.413045384 |
| 885 | MA, M1, L***, P, 1, F | 3.411058229 |
| 886 | LA02, M1, 1, P, LA08, F | 3.398787948 |
| 887 | Ma, 1, BHF, P, L***, F | 3.363638424 |
| 888 | A, L***, 1, P, 1, F | 3.342324735 |
| 889 | BHF, 1, LA08, P, LA08, F | 3.336977214 |
| 890 | Ma, 1, BHF, p, M1, F | 3.328291543 |
| 891 | Ma, 1, BHF, P, LA08, F | 3.29864556 |
| 892 | A, 1, BHF, P, L***, F | 3.283361952 |
| 893 | BHF, M1, 1, P, LA08, F | 3.282990164 |
| 894 | a, L***, M1, p, L***, F | 3.265382315 |
| 895 | MA, M1, 1, p, 1, F | 3.24089528 |
| 896 | BHF, M1, LA08, P, ML***, F | 3.233604517 |
| 897 | a, M1, BHF, P, M1, F | 3.219899095 |
| 898 | a, M1, BHF, p, LA08, F | 3.209271364 |
| 899 | BHF, ML***, LA08, p, M1, F | 3.203077023 |
| 900 | a, L***, 1, P, LA08, F | 3.192997038 |
| 901 | a, M1, LA08, p, L***, F | 3.188836831 |
| 902 | LA02, L***, ML***, p, LA08, F | 3.186920091 |
| 903 | MA, LA08, BHF, p, 1, F | 3.170561209 |
| 904 | BHF, LA08, LA08, P, 1, F | 3.16955984 |
| 905 | BHF, M1, L***, P, M1, F | 3.163553756 |
| 906 | Ma, LA08, BHF, p, 1, F | 3.158294592 |
| 907 | Ma, M1, M1, p, 1, F | 3.150790127 |
| 908 | BHF, LA08, M1, P, LA08, F | 3.096760797 |
| 909 | LA02, M1, M1, p, 1, F | 3.09466279 |
| 910 | MA, ML***, 1, p, LA08, F | 3.090144419 |
| 911 | A, LA08, LA08, p, L***, F | 3.064018713 |
| 912 | a, L***, 1, P, 1, F | 3.054271484 |
| 913 | BHF, LA08, BHF, P, 1, F | 3.051380451 |
| 914 | a, M1, M1, p, M1, F | 3.049366565 |
| 915 | Ma, LA08, 1, p, L***, F | 3.010185207 |
| 916 | BHF, M1, ML***, P, M1, F | 2.995666887 |
| 917 | A, 1, 1, P, 1, F | 2.99007427 |
| 918 | a, ML***, 1, P, 1, F | 2.946257625 |

| Compound No. | Peptomer Sequence | Permeability Value ($\times 10^{-6}$ cm/s) |
|---|---|---|
| 919 | MA, 1, M1, p, L***, F | 2.944306232 |
| 920 | Ma, LA08, LA08, P, LA08, F | 2.918329696 |
| 921 | a, 1, M1, p, 1, F | 2.887948226 |
| 922 | Ma, 1, 1, P, LA08, F | 2.86571319 |
| 923 | LA02, M1, BHF, p, M1, F | 2.864702906 |
| 924 | Ma, L***, ML***, p, 1, F | 2.86160219 |
| 925 | MA, M1, M1, P, M1, F | 2.831646367 |
| 926 | A, M1, 1, p, 1, F | 2.827508693 |
| 927 | Ma, LA08, 1, p, L***, F | 2.817673975 |
| 928 | Ma, M1, M1, p, M1, F | 2.779684151 |
| 929 | a, 1, LA08, P, 1, F | 2.750737412 |
| 930 | LA02, ML***, BHF, p, M1, F | 2.743938266 |
| 931 | a, L***, LA08, P, 1, F | 2.722944496 |
| 932 | MA, ML***, BHF, P, 1, F | 2.710500596 |
| 933 | MA, L***, 1, P, LA08, F | 2.709421124 |
| 934 | a, M1, M1, p, 1, F | 2.704207233 |
| 935 | LA02, ML***, BHF, p, LA08, F | 2.631383083 |
| 936 | LA02, L***, L***, p, 1, F | 2.616954756 |
| 937 | BHF, M1, LA08, P, ML***, F | 2.609283785 |
| 938 | Ma, M1, BHF, P, M1, F | 2.5838208 |
| 939 | a, 1, L***, P, ML***, F | 2.573450027 |
| 940 | BHF, ML***, LA08, P, LA08, F | 2.558926316 |
| 941 | A, 1, 1, p, 1, F | 2.552894905 |
| 942 | MA, 1, LA08, p, L***, F | 2.546867999 |
| 943 | a, 1, M1, P, M1, F | 2.53015786 |
| 944 | MA, M1, L***, P, L***, F | 2.507583547 |
| 945 | Ma, 1, 1, p, ML***, F | 2.483452527 |
| 946 | Ma, 1, BHF, p, M1, F | 2.482115084 |
| 947 | Ma, LA08, BHF, p, M1, F | 2.45866909 |
| 948 | MA, M1, M1, p, 1, F | 2.430356628 |
| 949 | A, 1, 1, p, M1, F | 2.392962435 |
| 950 | a, M1, LA08, p, M1, F | 2.366270393 |
| 951 | MA, 1, ML***, P, L***, F | 2.343324006 |
| 952 | a, L***, BHF, p, 1, F | 2.340204055 |
| 953 | BHF, ML***, M1, P, LA08, F | 2.334566318 |
| 954 | a, 1, 1, P, LA08, F | 2.322052743 |
| 955 | MA, 1, 1, P, M1, F | 2.321953035 |
| 956 | BHF, ML***, LA08, P, LA08, F | 2.317827141 |
| 957 | MA, LA08, BHF, P, 1, F | 2.315571818 |
| 958 | BHF, LA08, LA08, p, M1, F | 2.28082983 |
| 959 | A, 1, BHF, P, M1, F | 2.267306184 |
| 960 | a, L***, M1, p, M1, F | 2.262653009 |
| 961 | MA, 1, BHF, P, L***, F | 2.236342237 |
| 962 | BHF, L***, LA08, P, LA08, F | 2.224107332 |
| 963 | MA, L***, LA08, P, 1, F | 2.220888577 |
| 964 | BHF, M1, LA08, p, 1, F | 2.200773477 |
| 965 | a, 1, M1, p, ML***, F | 2.150885314 |
| 966 | Ma, M1, BHF, p, LA08, F | 2.130913971 |
| 967 | BHF, ML***, LA08, p, ML***, F | 2.113078776 |
| 968 | BHF, 1, LA08, p, LA08, F | 2.097299106 |
| 969 | MA, 1, 1, P, L***, F | 2.097240979 |
| 970 | MA, M1, BHF, P, M1, F | 2.084457722 |
| 971 | MA, M1, LA08, P, 1, F | 2.019124535 |
| 972 | a, LA08, 1, p, 1, F | 1.986395902 |
| 973 | MA, 1, BHF, P, M1, F | 1.976703241 |
| 974 | MA, 1, BHF, P, M1, F | 1.976703241 |
| 975 | a, ML***, 1, p, ML***, F | 1.949056916 |
| 976 | Ma, LA08, LA08, p, LA08, F | 1.931680012 |
| 977 | a, 1, LA08, P, L***, F | 1.917554286 |
| 978 | a, L***, L***, p, 1, F | 1.896665982 |
| 979 | MA, LA08, LA08, p, LA08, F | 1.891875636 |
| 980 | BHF, ML***, LA08, P, M1, F | 1.889646603 |
| 981 | BHF, ML***, M1, P, M1, F | 1.884015652 |
| 982 | MA, 1, BHF, p, L***, F | 1.878245365 |
| 983 | MA, 1, BHF, p, L***, F | 1.808753284 |
| 984 | BHF, LA08, L***, P, LA08, F | 1.800796374 |
| 985 | BHF, 1, LA08, P, LA08, F | 1.800065615 |
| 986 | BHF, ML***, ML***, P, LA08, F | 1.771227842 |
| 987 | Ma, L***, BHF, P, L***, F | 1.764502925 |
| 988 | BHF, LA08, BHF, p, M1, F | 1.749745372 |
| 989 | MA, M1, BHF, P, 1, F | 1.702128466 |
| 990 | Ma, 1, 1, p, M1, F | 1.644239055 |
| 991 | a, L***, 1, p, 1, F | 1.607246122 |
| 992 | BHF, M1, BHF, p, M1, F | 1.571943589 |
| 993 | BHF, ML***, LA08, p, LA08, F | 1.569937417 |
| 994 | MA, 1, 1, p, LA08, F | 1.505486657 |
| 995 | MA, LA08, L***, P, 1, F | 1.505202515 |
| 996 | Ma, LA08, 1, p, 1, F | 1.497100343 |
| 997 | BHF, LA08, LA08, p, L***, F | 1.489150081 |
| 998 | Ma, L***, 1, P, 1, F | 1.480181817 |
| 999 | MA, M1, M1, p, 1, F | 1.462990076 |
| 1000 | BHF, M1, 1, p, LA08, F | 1.447153033 |
| 1001 | Ma, M1, M1, P, 1, F | 1.390305635 |
| 1002 | a, 1, BHF, P, M1, F | 1.33946399 |
| 1003 | Ma, L***, 1, P, LA08, F | 1.326574827 |
| 1004 | MA, L***, 1, p, LA08, F | 1.324580747 |
| 1005 | BHF, ML***, ML***, P, M1, F | 1.324471746 |
| 1006 | MA, LA08, 1, p, LA08, F | 1.314797814 |
| 1007 | BHF, ML***, LA08, p, M1, F | 1.210283521 |
| 1008 | MA, L***, BHF, p, 1, F | 1.198411999 |
| 1009 | a, 1, 1, p, 1, F | 1.167434745 |
| 1010 | MA, L***, L***, p, 1, F | 1.159476244 |
| 1011 | Ma, M1, M1, p, 1, F | 1.15303301 |
| 1012 | MA, 1, 1, p, L***, F | 1.140630815 |
| 1013 | LA02, M1, ML***, p, L***, F | 1.136297368 |
| 1014 | BHF, M1, L***, p, M1, F | 1.127409942 |
| 1015 | Ma, L***, 1, p, 1, F | 1.116819581 |
| 1016 | a, 1, 1, P, M1, F | 1.110903769 |
| 1017 | BHF, LA08, LA08, p, M1, F | 1.103406979 |
| 1018 | Ma, M1, M1, p, 1, F | 1.040434901 |
| 1019 | MA, 1, L***, P, L***, F | 1.029054628 |
| 1020 | Ma, L***, L***, P, 1, F | 1.025434776 |
| 1021 | a, 1, 1, p, LA08, F | 1.018947064 |
| 1022 | Ma, 1, 1, p, LA08, F | 0.970181534 |
| 1023 | a, 1, LA08, p, L***, F | 0.963388403 |
| 1024 | a, 1, M1, p, M1, F | 0.937026383 |
| 1025 | a, 1, 1, P, 1, F | 0.932844583 |
| 1026 | LA02, LA08, BHF, p, M1, F | 0.916820282 |
| 1027 | BHF, LA08, BHF, P, LA08, F | 0.901184923 |
| 1028 | BHF, ML***, BHF, p, LA08, F | 0.881944575 |
| 1029 | Ma, 1, L***, p, L***, F | 0.876722677 |
| 1030 | BHF, M1, ML***, p, M1, F | 0.867335833 |
| 1031 | MA, M1, BHF, P, L***, F | 0.860854334 |
| 1032 | a, LA08, LA08, p, L***, F | 0.860791996 |
| 1033 | BHF, M1, BHF, p, LA08, F | 0.860571037 |
| 1034 | a, L***, 1, P, 1, F | 0.837694591 |
| 1035 | MA, 1, 1, p, LA08, F | 0.806641355 |
| 1036 | BHF, M1, LA08, P, LA08, F | 0.763620189 |
| 1037 | BHF, ML***, LA08, p, ML***, F | 0.747831927 |
| 1038 | BHF, LA08, LA08, P, LA08, F | 0.743104171 |
| 1039 | BHF, LA08, L***, p, ML***, F | 0.737624873 |
| 1040 | a, 1, 1, P, F | 0.736545175 |
| 1041 | a, 1, 1, p, M1, F | 0.713310536 |
| 1042 | BHF, M1, BHF, P, ML***, F | 0.670525435 |
| 1043 | Ma, M1, M1, p, 1, F | 0.644183993 |
| 1044 | Ma, L***, 1, p, L***, F | 0.602912753 |
| 1045 | a, 1, L***, p, L***, F | 0.592490913 |
| 1046 | BHF, LA08, BHF, p, M1, F | 0.523175137 |
| 1047 | Ma, L***, L***, p, 1, F | 0.478053842 |
| 1048 | a, L***, 1, p, L***, F | 0.424511465 |
| 1049 | MA, L***, L***, P, 1, F | 0.41125112 |
| 1050 | BHF, LA08, LA08, p, LA08, F | 0.361255187 |
| 1051 | MA, LA08, M1, p, LA08, F | 0.342058957 |
| 1052 | Ma, M1, BHF, p, M1, F | |
| 1053 | Ma, 1, 1, P, 1, F | |
| 1054 | MA, 1, 1, P, 1, F | |
| 1055 | MA, 1, 1, p, 1, F | |
| 1056 | LA02, L***, L***, p, L***, F | |
| 1057 | BHF, LA08, BHF, p, LA08, F | |
| 1058 | a, M1, BHF, p, M1, F | |
| 1059 | LA02, M1, BHF, P, M1, F | |
| 1060 | BHF, ML***, BHF, p, ML***, F | |
| 1061 | BHF, M1, BHF, P, M1, F | |
| 1062 | a, M1, BHF, p, M1, F | |
| 1063 | BHF, M1, BHF, p, M1, F | |
| 1064 | BHF, M1, BHF, P, M1, F | |
| 1065 | A, M1, M1, p, M1, F | |
| 1066 | a, M1, M1, p, M1, F | |
| 1067 | A, M1, M1, P, M1, F | |
| 1068 | a, M1, M1, P, M1, F | |

-continued

| Compound No. | Peptomer Sequence | Permeability Value (×10⁻⁶ cm/s) |
|---|---|---|
| 1069 | MA, M1, M1, P, M1, F | |
| 1070 | Ma, M1, M1, P, M1, F | |
| 1071 | Ma, 1, 1, p, 1, F | |
| 1072 | MA, 1, 1, p, 1, F | |
| 1073 | MA, 1, 1, p, 1, F | |
| 1074 | Ma, M1, BHF, P, M1, F | |
| 1075 | a, 1, 1, p, 1, F | |
| 1076 | MA, LA08, LA08, P, LA08, F | |
| 1077 | A, M1, BHF, p, M1, F | |
| 1078 | MA, M1, BHF, P, M1, F | |
| 1079 | a, M1, M1, p, M1, F | |
| 1080 | BHF, 1, 1, P, M1, F | |
| 1081 | LA02, M1, BHF, P, ML***, F | |
| 1082 | Ma, M1, M1, P, ML***, F | |
| 1083 | LA02, ML***, BHF, p, M1, F | |
| 1084 | Ma, ML***, ML***, P, 1, F | |
| 1085 | MAL***LA08, PLA08, F | |
| 1086 | Ma, L***, L***, p, ML***, F | |
| 1087 | MA, M1, M1, P, ML***, F | |
| 1088 | MA, M1, M1, P, ML***, F | |
| 1089 | MaL***, ML***, p, M1, F | |
| 1090 | MA, 1, 1, p, M1, F | |
| 1091 | Ma, L***, L***, P, ML***, F | |
| 1092 | a, 1, ML***, P, M1, F | |
| 1093 | MA, 1, 1, P, ML***, F | |
| 1094 | ALA08, BHF, p, L***, F | |
| 1095 | MA, M1, ML***, P, 1, F | |
| 1096 | LA02, ML***, ML***, PLA08, F | |
| 1097 | MA, 1, 1, p, ML***, F | |
| 1098 | BHF, 1, ML***, p, ML***, F | |
| 1099 | A, M1, BHF, p, L***, F | |
| 1100 | a, ML***, ML***, p, 1, F | |
| 1101 | Ma, M1, ML***, p, L***, F | |
| 1102 | MA, M1, LA08, P, M1, F | |
| 1103 | MaL***, M1, p, 1, F | |
| 1104 | A, 1, M1, p, M1, F | |
| 1105 | Ma, ML***, LA08, p, 1, F | |
| 1106 | BHF, ML***, L***, p, M1, F | |
| 1107 | BHF, ML***, L***, p, M1, F | |
| 1108 | A, 1, BHF, p, L***, F | |
| 1109 | a, ML***, LA08, P, ML***, F | |
| 1110 | MAL***LA08, p, LA08, F | |
| 1111 | a, ML***, ML***, p, 1, F | |
| 1112 | A, ML***, BHF, P, 1, F | |
| 1113 | MAL***, 1, p, 1, F | |
| 1114 | Ma, 1, L***, p, ML***, F | |
| 1115 | BHF, ML***, L***, P, M1, F | |
| 1116 | Ma, 1, 1, p, L***, F | |
| 1117 | BHF, ML***, L***, p, LA08, F | |
| 1118 | MaL***, ML***, p, LA08, F | |
| 1119 | MA, M1, M1, P, 1, F | |
| 1120 | Ma, M1, LA08, p, L***, F | |
| 1121 | A, ML***, BHF, PLA08, F | |
| 1122 | BHF, ML***, L***, PLA08, F | |
| 1123 | BHF, M1, L***, p, LA08, F | |
| 1124 | LA02, ML***, L***, PLA08, F | |
| 1125 | a, 1, 1, p, ML***, F | |
| 1126 | MA, 1, BHF, PLA08, F | |
| 1127 | BHF, ML***, LA08, p, LA08, F | |
| 1128 | Ma, M1, M1, P, ML***, F | |
| 1129 | LA02, L***, L***, p, LA08, F | |
| 1130 | Ma, M1, 1, p, M1, F | |
| 1131 | MA, M1, ML***, p, M1, F | |
| 1132 | MA, ML***, ML***, P, 1, F | |
| 1133 | a, 1, 1, p, L***, F | |
| 1134 | a, ML***, BHF, p, LA08, F | |
| 1135 | Ma, ML***, LA08, p, M1, F | |
| 1136 | LA02, M1, 1, P, M1, F | |
| 1137 | a, M1, 1, p, L***, F | |
| 1138 | a, ML***, 1, p, L***, F | |
| 1139 | a, 1, 1, P, ML***, F | |
| 1140 | Ma, 1, L***, P, L***, F | |
| 1141 | aL***, ML***, P, M1, F | |
| 1142 | a, M1, M1, P, 1, F | |
| 1143 | BHF, ML***, L***, p, L***, F | |
| 1144 | BHF, ML***, LA08, p, ML***, F | |
| 1145 | A, ML***, BHF, p, LA08, F | |
| 1146 | MAL***, 1, p, LA08, F | |
| 1147 | BHFLA08, BHF, p, L***, F | |
| 1148 | a, 1, M1, P, M1, F | |
| 1149 | A, 1, 1, p, L***, F | |
| 1150 | BHF, M1, LA08, p, M1, F | |
| 1151 | a, ML***, BHF, P, L***, F | |
| 1152 | MaL***, BHF, p, 1, F | |
| 1153 | Ma, M1, 1, p, M1, F | |
| 1154 | BHF, ML***, L***, p, LA08, F | |
| 1155 | a, 1, BHF, P, L***, F | |
| 1156 | BHF, M1, M1, P, LA08, F | |
| 1157 | Ma, ML***, L***, P, L***, F | |
| 1158 | LA02, LA08, BHF, P, ML***, F | |
| 1159 | MA, ML***, L***, p, L***, F | |
| 1160 | BHF, L***, BHF, p, L***, F | |
| 1161 | Ma, L***, BHF, p, L***, F | |
| 1162 | A, M1, LA08, P, 1, F | |
| 1163 | Ma, ML***, BHF, P, LA08, F | |
| 1164 | a, 1, M1, p, LA08, F | |
| 1165 | A, L***, L***, P, LA08, F | |
| 1166 | Ma, ML***, L***, p, L***, F | |
| 1167 | BHF, 1, ML***, p, LA08, F | |
| 1168 | MA, L***, BHF, p, L***, F | |
| 1169 | A, ML***, L***, p, ML***, F | |
| 1170 | A, L***, M1, p, 1, F | |
| 1171 | MA, ML***, 1, p, L***, F | |
| 1172 | a, 1, M1, p, M1, F | |
| 1173 | BHF, M1, BHF, p, 1, F | |
| 1174 | LA02, L***, BHF, p, L***, F | |
| 1175 | a, 1, M1, P, ML***, F | |
| 1176 | MA, M1, M1, P, 1, F | |
| 1177 | BHF, M1, ML***, p, LA08, F | |
| 1178 | BHF, ML***, LA08, p, L***, F | |
| 1179 | BHF, ML***, LA08, p, L***, F | |
| 1180 | A, 1, M1, p, L***, F | |
| 1181 | A, 1, ML***, P, L***, F | |
| 1182 | A, M1, M1, P, 1, F | |
| 1183 | LA02, 1, LA08, p, 1, F | |
| 1184 | Ma, ML***, 1, p, ML***, F | |
| 1185 | a, 1, M1, p, L***, F | |
| 1186 | LA02, M1, LA08, P, LA08, F | |
| 1187 | A, LA08, L***, p, L***, F | |
| 1188 | Ma, L***, LA08, p, ML***, F | |
| 1189 | Ma, L***, BHF, p, LA08, F | |
| 1190 | MA, M1, 1, p, L***, F | |
| 1191 | A, L***, 1, p, 1, F | |
| 1192 | a, L***, ML***, P, 1, F | |
| 1193 | BHF, ML***, BHF, p, LA08, F | |
| 1194 | BHF, L***, LA08, p, 1, F | |
| 1195 | Ma, 1, LA08, P, L***, F | |
| 1196 | A, L***, ML***, p, 1, F | |
| 1197 | MA, L***, LA08, p, L***, F | |
| 1198 | a, ML***, BHF, p, M1, F | |
| 1199 | a, M1, LA08, P, M1, F | |
| 1200 | BHF, L***, M1, PLA08, F | |
| 1201 | MA, 1, LA08, p, 1, F | |
| 1202 | LA02, ML***, BHF, P, L***, F | |
| 1203 | BHF, M1, LA08, P, 1, F | |
| 1204 | A, M1, LA08, P, LA08, F | |
| 1205 | BHF, M1, L***, p, ML***, F | |
| 1206 | Ma, 1, LA08, p, L***, F | |
| 1207 | BHF, M1, LA08, p, ML***, F | |
| 1208 | MAL***LA08, PLA08, F | |
| 1209 | a, M1, BHF, p, LA08, F | |
| 1210 | MA, L***, BHF, P, 1, F | |
| 1211 | MA, LA08, BHF, P, L***, F | |
| 1212 | a, ML***, LA08, p, LA08, F | |
| 1213 | MA, LA08, BHF, p, L***, F | |
| 1214 | A, 1, L***, p, L***, F | |
| 1215 | aLA08, ML***, p, ML***, F | |
| 1216 | Ma, M1, LA08, P, 1, F | |
| 1217 | a, 1, ML***, p, L***, F | |
| 1218 | BHF, M1, M1, P, ML***, F | |

-continued

| Compound No. | Peptomer Sequence | Permeability Value (×10⁻⁶ cm/s) |
|---|---|---|
| 1219 | Ma, ML***, LA08, P, 1, F | |
| 1220 | Ma, 1, BHF, p, ML***, F | |
| 1221 | BHF, M1, M1, p, LA08, F | |
| 1222 | Ma, M1, BHF, p, 1, F | |
| 1223 | MA, M1, BHF, p, 1, F | |
| 1224 | LA02, LA08, M1, P, M1, F | |
| 1225 | MA, ML***LA08, P, 1, F | |
| 1226 | MA, LA08, ML***, P, 1, F | |
| 1227 | Ma, LA08, L***, p, M1, F | |
| 1228 | a, LA08, M1, p, L***, F | |
| 1229 | a, LA08, 1, P, ML***, F | |
| 1230 | A, LA08, M1, p, ML***, F | |
| 1231 | a, LA08, L***, p, 1, F | |
| 1232 | MA, LA08, L***, p, 1, F | |
| 1233 | a, LA08, LA08, p, L***, F | |
| 1234 | LA02, LA08, L***, p, LA08, F | |
| 1235 | MA, LA08, LA08, P, L***, F | |
| 1236 | a, LA08, LA08, p, L***, F | |
| 1237 | a, LA08, LA08, p, L***, F | |
| 1238 | A, 1, M1, p, M1, F | |
| 1239 | BHF, 1, M1, p, 1, F | |
| 1240 | Ma, M1, M1, P, ML***, F | |

MSMS Processing

Centroided MS2 spectra first had their parent ion mass corrected to high resolution by locating the closest high resolution mass in the MS1 spectrum, then filtered down to those spectra matching masses of the sublibrary of interest. MS2 spectra were then grouped per their source-peak, before using the most intense as a base spectrum for intensity combination. Combination occurred by a one-to-one m/z correspondence rule with the closest m/z being matched between spectra. In a separate process, all MS2 spectra (pre-filtration) had their peak intensities collected into a single dataset, which was filtered to the lowest 90% and used to generate a kernel density estimate of the noise distribution. From that noise distribution, a noise threshold was decided by setting it to the p-value of 0.05 of a noise peak having intensity equal to or greater than the threshold. Finally, intensity-combined MS2 spectra were filtered by peak intensity at that threshold.

Sequencing

Each MS2 spectrum was first matched at high resolution (0.015 m/z) to all possible parent compounds from the library design. All possible fragment masses were belonging to those possible parent compounds were generated, then matched against the MS2 spectrum peaks. Based on those matches, a best candidate was identified. Number of matches, identity of matches, and peak intensity were all included in the scoring of each candidate molecule.

Data Correlation

Permeability data and sequencing data were correlated by mass and retention time matches within large precision gaps to account for inter-run variability (time precision=3 seconds, mass precision=0.03). The data were then pruned of those peaks for which no Pe value could be calculated and with unacceptably low sequencing quality (generally due to poor MS2 data quality).

Abbreviations

ACN, acetonitrile; COMU, (1-Cyano-2-ethoxy-2-oxoethylidenaminooxy)dimethylamino-morpholino-carbenium hexafluorophosphate; DBU, 1,8-Diazabicyclo[5.4.0]undec-7-ene; DCM, dichloromethane; DMF, N,N-dimethylformamide; DIPEA, diisopropylethylamine; DMSO, dimethylsulfoxide; Fmoc, 9-fluorenylmethoxycarbonyl; HATU, 1-[Bis(dimethylamino)methylene]-1H-1,2,3-triazolo[4,5-b]pyridinium 3-oxide hexafluorophosphate; LCMS, liquid chromatography mass spectrometry; MeOH, methanol; N2, nitrogen; PTFE, Polytetrafluoroethylene; RP, reverse phase; SPPS, solid phase peptide synthesis; TFA, trifluoroacetic acid.

PAMPA Permeability of Resynthesized Compounds

A set of hexapeptomers were resynthesized and the parallel artificial membrane permeability assay was performed to determine the permeability values. Each peptomer sequence with determined permeability (Pe) value is shown in Table 3.

TABLE 3

| Compound No. | Peptomer Sequence | Bulk Permeability Value (× 10⁻⁶ cm/s) | Pure Permeability Value (× 10⁻⁶ cm/s) |
|---|---|---|---|
| 1 | a, L, L, p, 1, F | 0.58 | 2.51 |
| 2 | BHF, ML, L, p, M1, F | 0.74 | 3.27 |
| 3 | BHF, 1, BHF, p, 1, F | 4.08 | 7.43 |
| 4 | Ma, 1, L, p, 1, F | 2.94 | 11.34 |
| 5 | A, L, L, P, M1, F | 2.65 | 5.1 |
| 6 | a, 1, 1, p, ML, F | 0.17 | 1.91 |
| 7 | Ma, L, BHF, p, 1, F | 0.16 | 6.65 |
| 8 | A, L, BHF, P, ML, F | 4.53 | >22 |
| 9 | BHF, L, 1, P, L, F | 12.76 | >22 |
| 10 | BHF, 1, L, p, 1, F | 2.52 | 8.02 |
| 11 | BHF, L, 1, p, 1, F | 4.94 | 7.48 |
| 12 | BHF, L, L, P, 1, F | 1.43 | 6.92 |

Aspects, including embodiments, of the subject matter described herein may be beneficial alone or in combination, with one or more other aspects or embodiments. Without limiting the description, certain non-limiting aspects of the disclosure numbered 1-68 are provided below. As will be apparent to those of skill in the art upon reading this disclosure, each of the individually numbered aspects may be used or combined with any of the preceding of following individually numbered aspects. This is intended to provide support for all such combinations of aspects and is not limited to combinations of aspects explicitly provided below:

1. A compound of Formula I:

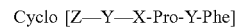

wherein:

X is

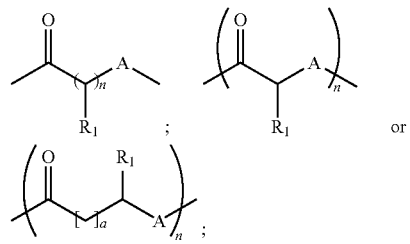

Y is

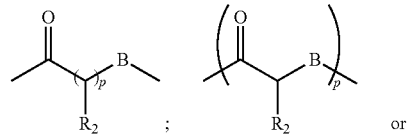

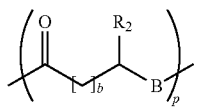

Z is

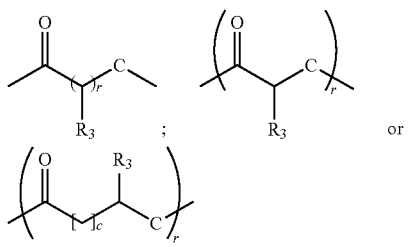

each R₁ is independently selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl, or optionally, R₁ together with the atoms to which it is bonded form a cycloheteroalkyl or substituted cycloheteroalkyl ring;

each R₂ is independently selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl, or optionally, R₁ together with the atoms to which it is bonded form a cycloheteroalkyl or substituted cycloheteroalkyl ring;

each R₃ is independently selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl, or optionally, R₁ together with the atoms to which it is bonded form a cycloheteroalkyl or substituted cycloheteroalkyl ring;

A is selected from —NR$_a$—, —O— or —S—;
B is selected from —NR$_b$—, —O— or —S—;
C is selected from —NR$_c$—, —O— or —S—;
each R$_a$, R$_b$, R$_c$ is independently selected from hydrogen, alkyl, substituted alkyl, aryl and substituted aryl, or
R₁ and R$_a$ together with the atoms to which they are bonded form a cycloheteroalkyl or substituted cycloheteroalkyl ring;
R₂ and R$_b$ together with the atoms to which they are bonded form a cycloheteroalkyl or substituted cycloheteroalkyl ring;
R₃ and R$_c$ together with the atoms to which they are bonded form a cycloheteroalkyl or substituted cycloheteroalkyl ring;
n is an integer from one to 5 and a is an integer from one to 5;
p is an integer from one to 5 and b is an integer from one to 5; and
r is an integer from one to 5 and c is an integer from one to 5;
or a pharmaceutical acceptable salt, solvate or hydrate thereof.

2. The compound according to 1, wherein each R₁ is independently selected from a side chain of an amino acid selected from the group consisting of alanine, arginine, asparagine, aspartic acid, cysteine, glycine, glutamine, glutamic acid, histidine, isoleucine, leucine, lysine, methionine, phenylalanine, proline, serine, threonine, tryptophan, tyrosine and valine.

3. The compound according to 2, wherein each R₁ is independently selected from a side chain of glycine, leucine or phenylalanine.

4. The compound according to any one of 1-3, wherein each R₂ is independently selected from a side chain of an amino acid selected from the group consisting of alanine, arginine, asparagine, aspartic acid, cysteine, glycine, glutamine, glutamic acid, histidine, isoleucine, leucine, lysine, methionine, phenylalanine, proline, serine, threonine, tryptophan, tyrosine and valine.

5. The compound according to any one of 1-3, wherein:
X is

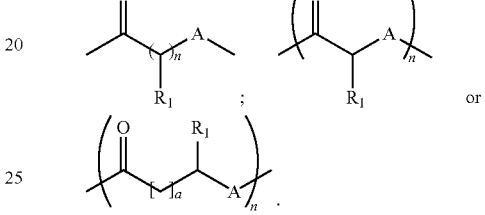

6. The compound according to any one of 1-3, wherein:
Y is

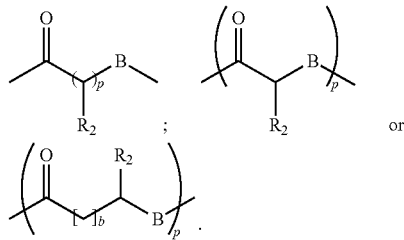

7. The compound according to 6, wherein each R₂ is independently selected from a side chain of leucine or glycine.

8. The compound according to any one of 1-7, wherein each R₃ is independently selected from a side chain of an amino acid selected from the group consisting of alanine, arginine, asparagine, aspartic acid, cysteine, glycine, glutamine, glutamic acid, histidine, isoleucine, leucine, lysine, methionine, phenylalanine, proline, serine, threonine, tryptophan, tyrosine and valine.

9. The compound according to 8, wherein each R₃ is independently selected from a side chain of glycine, alanine or phenylalanine.

10. The compound according to any one of 1-9, wherein n is 2 and each R₁ is selected from a side chain of glycine or phenylalanine.

11. The compound according to any one of 1-10, wherein r is 2 and each R₃ is selected from a side chain of glycine or phenylalanine.

12. The compound according to any one of 1-11, wherein p is 1 and R₂ is glycine or leucine.

13. The compound according to any one of 1-12, wherein A is NR$_a$.

14. The compound according to 13, wherein R$_a$ is selected from hydrogen, alkyl or aryl.

15. The compound according to 14, wherein the alkyl is methyl or propyl.

16. The compound according to 14, wherein the aryl is benzyl.

17. The compound according to any one of 1-16, wherein B is $NR_b$.

18. The compound according to 17, wherein $R_b$ is selected from hydrogen, alkyl or aryl.

19. The compound according to 18, wherein the alkyl is methyl.

20. The compound according to 18, wherein the aryl is benzyl.

21. The compound according to any one of 1-20, wherein C is $NR_c$.

22. The compound according to 21, wherein $R_c$ is selected from hydrogen, alkyl or aryl.

23. The compound according to 22, wherein the alkyl is methyl.

24. The compound according to 22, wherein the aryl is benzyl.

25. The compound according to any one of 1-24, wherein X is a residue of a D-amino acid or L-amino acid selected from alanine, arginine, asparagine, aspartic acid, cysteine, glycine, glutamine, glutamic acid, histidine, isoleucine, leucine, lysine, methionine, phenylalanine, β-homophenylalanine, proline, serine, threonine, tryptophan, tyrosine and valine or an N-alkyl derivative thereof.

26. The compound according to 25, wherein X is a D-amino acid selected from alanine, arginine, asparagine, aspartic acid, cysteine, glycine, glutamine, glutamic acid, histidine, isoleucine, leucine, lysine, methionine, phenylalanine, β-homophenylalanine, proline, serine, threonine, tryptophan, tyrosine and valine or an N-alkyl derivative thereof.

27. The compound according to 26, wherein X is D-leucine or an N-alkyl derivative thereof.

28. The compound according to 27, wherein X is D-leucine.

29. The compound according to 27, wherein X is N-methyl D-leucine.

30. The compound according to 25, wherein X is an L-amino acid selected from alanine, arginine, asparagine, aspartic acid, cysteine, glycine, glutamine, glutamic acid, histidine, isoleucine, leucine, lysine, methionine, phenylalanine, β-homophenylalanine, proline, serine, threonine, tryptophan, tyrosine and valine or an N-alkyl derivative thereof.

31. The compound according to 30, wherein X is L-leucine or an N-alkyl derivative thereof.

32. The compound according to 27, wherein X is L-leucine.

33. The compound according to 27, wherein X is N-methyl L-leucine.

34. The compound according to 30, wherein X is L-β-homophenylalanine or an alkyl derivative thereof.

35. The compound according to 30, wherein X is L-β-homophenylalanine.

36. The compound according to 25, wherein X is glycine or an N-alkyl derivative thereof.

37. The compound according to 36, wherein X is N-benzyl glycine.

38. The compound according to any one of 1-37, wherein Y is a residue of a D-amino acid or L-amino acid selected from alanine, arginine, asparagine, aspartic acid, cysteine, glycine, glutamine, glutamic acid, histidine, isoleucine, leucine, lysine, methionine, phenylalanine, β-homophenylalanine, proline, serine, threonine, tryptophan, tyrosine and valine or an N-alkyl derivative thereof.

39. The compound according to 38, wherein Y is a D-amino acid selected from alanine, arginine, asparagine, aspartic acid, cysteine, glycine, glutamine, glutamic acid, histidine, isoleucine, leucine, lysine, methionine, phenylalanine, β-homophenylalanine, proline, serine, threonine, tryptophan, tyrosine and valine or an N-alkyl derivative thereof.

40. The compound according to 39, wherein Y is D-leucine or an N-alkyl derivative thereof.

41. The compound according to 40, wherein Y is D-leucine.

42. The compound according to 40, wherein Y is N-methyl D-leucine.

43. The compound according to 38, wherein Y is an L-amino acid selected from alanine, arginine, asparagine, aspartic acid, cysteine, glycine, glutamine, glutamic acid, histidine, isoleucine, leucine, lysine, methionine, phenylalanine, β-homophenylalanine, proline, serine, threonine, tryptophan, tyrosine and valine or an N-alkyl derivative thereof.

44. The compound according to 43, wherein Y is L-leucine or an N-alkyl derivative thereof.

45. The compound according to 44, wherein Y is L-leucine.

46. The compound according to 44, wherein Y is N-methyl L-leucine.

47. The compound according to 38, wherein Y is glycine or an N-alkyl derivative thereof.

48. The compound according to 47, wherein Y is N-benzyl glycine.

49. The compound according to any one of 1-48, wherein Z is a residue of a D-amino acid or L-amino acid selected from alanine, arginine, asparagine, aspartic acid, cysteine, glycine, glutamine, glutamic acid, histidine, isoleucine, leucine, lysine, methionine, phenylalanine, β-homophenylalanine, proline, serine, threonine, tryptophan, tyrosine and valine or an N-alkyl derivative thereof.

50. The compound according to 49, wherein Z is a D-amino acid selected from alanine, arginine, asparagine, aspartic acid, cysteine, glycine, glutamine, glutamic acid, histidine, isoleucine, leucine, lysine, methionine, phenylalanine, β-homophenylalanine, proline, serine, threonine, tryptophan, tyrosine and valine or an N-alkyl derivative thereof.

51. The compound according to 50, wherein Z is D-alanine or an N-alkyl derivative thereof.

52. The compound according to 51, wherein Z is D-alanine.

53. The compound according to 51, wherein Z is N-methyl D-leucine.

54. The compound according to 49, wherein Z is an L-amino acid selected from alanine, arginine, asparagine, aspartic acid, cysteine, glycine, glutamine, glutamic acid, histidine, isoleucine, leucine, lysine, methionine, phenylalanine, β-homophenylalanine, proline, serine, threonine, tryptophan, tyrosine and valine or an N-alkyl derivative thereof.

55. The compound according to 54, wherein Z is L-alanine or an N-alkyl derivative thereof.

56. The compound according to 55, wherein Z is L-alanine.

57. The compound according to 55, wherein Z is N-methyl L-alanine.

58. The compound according to 49, wherein Z is L-β-homophenylalanine or an alkyl derivative thereof.

59. The compound according to 30, wherein Z is L-β-homophenylalanine.

60. The compound according to 49, wherein Z is glycine or an N-alkyl derivative thereof.

61. The compound according to 36, wherein Z is N-propyl glycine.

62. A compound of Formula 1:

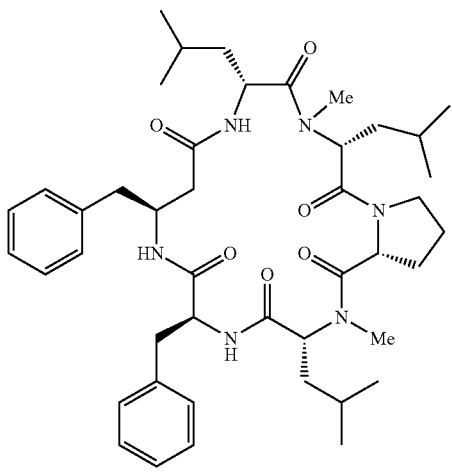

Formula 1 or a pharmaceutical acceptable salt, solvate or hydrate thereof.

63. A compound of Formula 2:

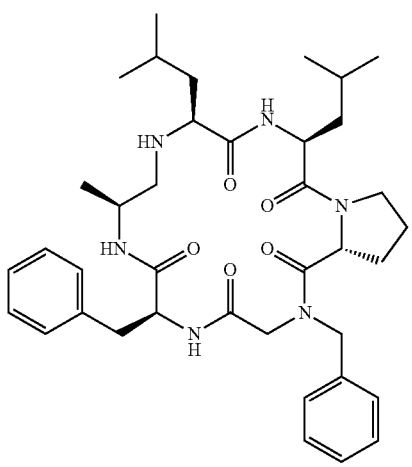

Formula 2 or a pharmaceutical acceptable salt, solvate or hydrate thereof.

64. A composition comprising:
a compound or pharmaceutically acceptable salt, solvate or hydrate thereof according to any one of 1-63; and
a pharmaceutically acceptable vehicle.

65. The composition according to 64, wherein the composition comprises:
a compound according to any one of 1-63; and
a pharmaceutically acceptable vehicle.

66. A method comprising administering a compound or pharmaceutically acceptable salt, solvate or hydrate thereof according to any one of 1-63 to a subject.

67. A method comprising administering a composition according to any one of 64-65 to a subject.

68. A library comprising 50 or more cyclic peptides, each cyclic peptide independently having a Formula I:

Cyclo [Z—Y—X-Pro-Y-Phe]    Formula I wherein:
X is

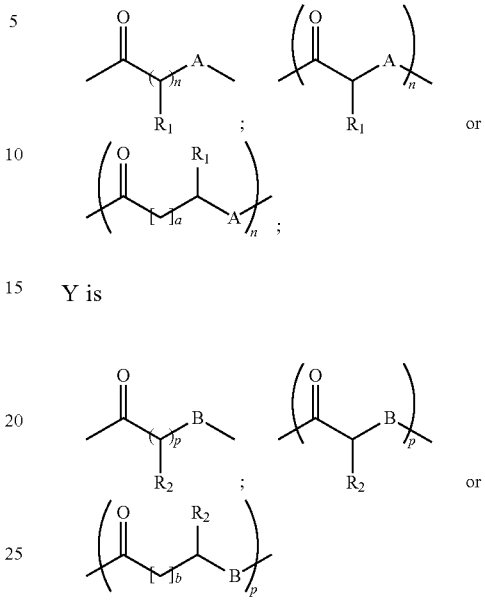

Y is

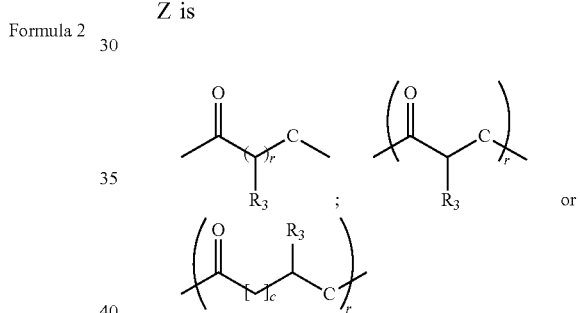

Z is each $R_1$ is independently selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl, or optionally, $R_1$ together with the atoms to which it is bonded form a cycloheteroalkyl or substituted cycloheteroalkyl ring;

each $R_2$ is independently selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl, or optionally, $R_1$ together with the atoms to which it is bonded form a cycloheteroalkyl or substituted cycloheteroalkyl ring;

each $R_3$ is independently selected from hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, and substituted heteroarylalkyl, or optionally, $R_1$ together with the atoms to which it is bonded form a cycloheteroalkyl or substituted cycloheteroalkyl ring;

A is selected from —$NR_a$—, —O— or —S—;
B is selected from —$NR_b$—, —O— or —S—;
C is selected from —$NR_c$—, —O— or —S—;

each $R_a$, $R_b$, $R_c$ is independently selected from hydrogen, alkyl, substituted alkyl, aryl and substituted aryl, or R$_1$ and R$_a$ together with the atoms to which they are bonded form a cycloheteroalkyl or substituted cycloheteroalkyl ring;

R$_2$ and R$_b$ together with the atoms to which they are bonded form a cycloheteroalkyl or substituted cycloheteroalkyl ring;

R$_3$ and R$_c$ together with the atoms to which they are bonded form a cycloheteroalkyl or substituted cycloheteroalkyl ring;

n is an integer from one to 5 and a is an integer from one to 5;

p is an integer from one to 5 and b is an integer from one to 5; and r is an integer from one to 5 and c is an integer from one to 5;

or a pharmaceutical acceptable salt, solvate or hydrate thereof.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims. It is also to be understood that the terminology used herein is for the purpose of describing particular embodiments only, and is not intended to be limiting, since the scope of the present invention will be limited only by the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A compound of Formula I:

Cyclo [Z—Y$_1$—X-Pro-Y$_2$-Phe]    Formula I wherein:
    X is selected from L-leucine, N-methyl L-leucine, D-leucine, N-methyl D-leucine, L-alanine, D-alanine, N-methyl L-alanine, N-methyl D-alanine, L-β-homophenylalanine, propyl peptoid and benzylpeptoid;
    Y$_1$ is selected from L-leucine, N-methyl L-leucine, D-leucine, N-methyl D-leucine, L-alanine, D-alanine, N-methyl L-alanine, N-methyl D-alanine, L-β-homophenylalanine, propyl peptoid and benzylpeptoid;
    Y$_2$ selected from L-leucine, N-methyl L-leucine, D-leucine, N-methyl D-leucine, L-alanine, D-alanine, N-methyl L-alanine, N-methyl D-alanine, L-β-homophenylalanine, propyl peptoid and benzylpeptoid; and
    Z is selected from L-leucine, N-methyl L-leucine, D-leucine, N-methyl D-leucine, L-alanine, D-alanine, N-methyl L-alanine, N-methyl D-alanine, L-β-homophenylalanine, propyl peptoid and benzylpeptoid.

2. The compound according to claim 1, wherein X is selected from L-leucine, N-methyl L-leucine, D-leucine, N-methyl D-leucine, L-β-homophenylalanine and benzylpeptoid.

3. The compound according to claim 1, wherein Y$_1$ is selected from L-leucine, N-methyl L-leucine, D-leucine, N-methyl D-leucine and benzylpeptoid.

4. The compound according to claim 1, wherein Z is selected from L-alanine, N-methyl L-alanine, N-methyl D-alanine, propyl peptoid and L-β-homophenylalanine.

5. A compound of Formula 1:
    X is selected from L-leucine, N-methyl L-leucine, D-leucine, N-methyl D-leucine, L-β-homophenylalanine and benzylpeptoid;
    Y$_1$ is selected from L-leucine, N-methyl L-leucine, D-leucine, N-methyl D-leucine and benzylpeptoid;
    Y$_2$ is selected from L-leucine, N-methyl L-leucine, D-leucine, N-methyl D-leucine and benzylpeptoid; and
    Z is selected from L-alanine, N-methyl L-alanine, N-methyl D-alanine, propyl peptoid and L-β-homophenylalanine.

6. A compound having the formula:

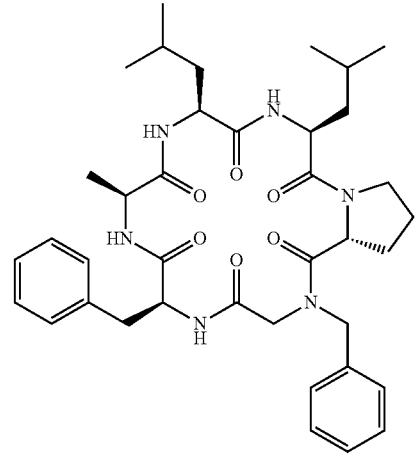 [SMILES: CC(C)C[C@@H]1NC(=O)[C@H](C)NC(=O)[C@H](Cc2ccccc2)NC(=O)CN(Cc2ccccc2)C(=O)[C@H]2CCCN2C(=O)[C@H](CC(C)C)NC1=O]

or a pharmaceutical acceptable salt, solvate or hydrate thereof.

7. The compound according to claim 1, wherein the Y$_2$ is selected from L-leucine, N-methyl L-leucine, D-leucine, N-methyl D-leucine and benzylpeptoid.

8. The compound according to claim 1, wherein:
    X is selected from L-leucine, N-methyl L-leucine, D-leucine, N-methyl D-leucine, L-β-homophenylalanine and benzylpeptoid;
    Y$_1$ is selected from L-leucine, N-methyl L-leucine, D-leucine, N-methyl D-leucine, and benzylpeptoid;
    Y$_2$ is selected from L-leucine, N-methyl L-leucine, D-leucine, N-methyl D-leucine, and benzylpeptoid; and
    Z is selected from L-alanine, N-methyl L-alanine, N-methyl D-alanine, propyl peptoid and L-β-homophenylalanine.

9. The compound according to claim 1, wherein:

X is leucine;

$Y_1$ is selected from L-leucine, N-methyl L-leucine, D-leucine, N-methyl D-leucine and benzylpeptoid;

$Y_2$ is selected from L-leucine, N-methyl L-leucine, D-leucine, N-methyl D-leucine and benzylpeptoid; and Z is selected from L-alanine, N-methyl L-alanine, N-methyl D-alanine, propyl peptoid and L-β-homophenylalanine.

10. The compound according to claim 9, wherein X is L-leucine.

11. The compound according to claim 9, wherein X is D-leucine.

12. The compound according to claim 1, wherein:

X is L-β-homophenylalanine;

$Y_1$ is selected from L-leucine, N-methyl L-leucine, D-leucine, N-methyl D-leucine and benzylpeptoid;

$Y_2$ is selected from L-leucine, N-methyl L-leucine, D-leucine, N-methyl D-leucine and benzylpeptoid; and Z is selected from L-alanine, N-methyl L-alanine, N-methyl D-alanine, propyl peptoid and L-β-homophenylalanine;

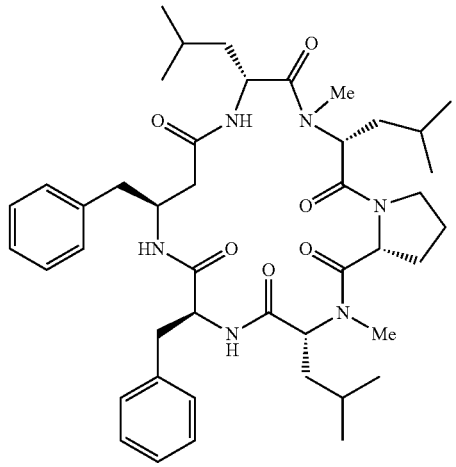

Formula 1 or a pharmaceutical acceptable salt, solvate or hydrate thereof.

* * * * *

UNITED STATES PATENT AND TRADEMARK OFFICE
CERTIFICATE OF CORRECTION

PATENT NO. : 11,001,609 B2  
APPLICATION NO. : 16/604482  
DATED : May 11, 2021  
INVENTOR(S) : Scott Lokey Page 1 of 2

It is certified that error appears in the above-identified patent and that said Letters Patent is hereby corrected as shown below:

In the Specification

In Column 6, Line 37, please replace "7E" with --- $\pi$ ---.

In the Claims

In Column 66, please delete Claim 5 and replace it with
--- 5. A compound of Formula 1:

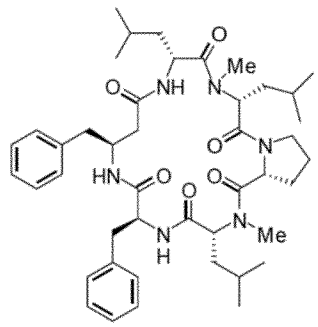

Formula 1
or a pharmaceutical acceptable salt, solvate or hydrate thereof. ---.

Signed and Sealed this  
Twenty-second Day of March, 2022

Drew Hirshfeld  
*Performing the Functions and Duties of the*  
*Under Secretary of Commerce for Intellectual Property and*  
*Director of the United States Patent and Trademark Office*

CERTIFICATE OF CORRECTION (continued)
U.S. Pat. No. 11,001,609 B2

In Column 67, Claim 12, please delete

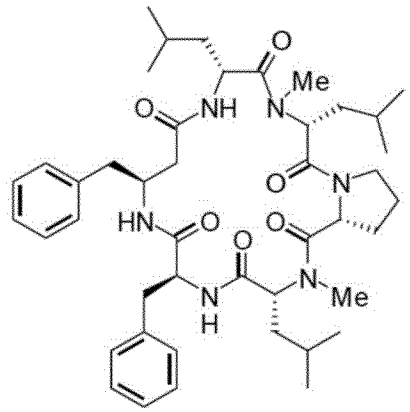

Formula 1

";
or a pharmaceutical acceptable salt, solvate or hydrate thereof." and replace it with
--- . ---.